(12) United States Patent
Van Den Hazel et al.

(10) Patent No.: US 7,524,931 B2
(45) Date of Patent: Apr. 28, 2009

(54) FULL-LENGTH INTERFERON GAMMA POLYPEPTIDE VARIANTS

(75) Inventors: Bart Van Den Hazel, Copenhagen (DK); Anne Dam Jensen, Copenhagen (DK); Frank Bechnygaard, Humlebaek (DK); Kim Vilbour Andersen, Bronshoj (DK)

(73) Assignee: Maxygen Holdings Ltd., Grand Cayman (KY)

(*) Notice: Subject to any disclaimer, the term of this patent is extended or adjusted under 35 U.S.C. 154(b) by 285 days.

(21) Appl. No.: 10/521,008

(22) PCT Filed: Jun. 23, 2003

(86) PCT No.: PCT/DK03/00426

§ 371 (c)(1),
(2), (4) Date: Oct. 27, 2005

(87) PCT Pub. No.: WO2004/005341

PCT Pub. Date: Jan. 15, 2004

(65) Prior Publication Data

US 2006/0099175 A1     May 11, 2006

Related U.S. Application Data

(60) Provisional application No. 60/394,120, filed on Jul. 3, 2002, provisional application No. 60/415,214, filed on Sep. 30, 2002, provisional application No. 60/417,399, filed on Oct. 9, 2002.

(51) Int. Cl.
*C07K 14/52* (2006.01)
*C07K 14/00* (2006.01)
*C12N 15/00* (2006.01)
*C12N 15/21* (2006.01)
*C12P 21/00* (2006.01)
*C07H 21/04* (2006.01)
*A61K 38/19* (2006.01)

(52) U.S. Cl. .................... 530/351; 530/350; 435/69.51; 435/70.1; 435/320.1; 536/23.1; 536/23.52; 424/85.1

(58) Field of Classification Search .............. None
See application file for complete search history.

(56) References Cited

U.S. PATENT DOCUMENTS

| | | | |
|---|---|---|---|
| 4,457,867 A | 7/1984 | Ishida | |
| 4,588,585 A | 5/1986 | Mark et al. | |
| 4,604,284 A | 8/1986 | Kung et al. | |
| 4,695,623 A | 9/1987 | Stabinsky | |
| 4,727,138 A | 2/1988 | Goeddel et al. | |
| 4,758,656 A | 7/1988 | Itoh et al. | |
| 4,762,791 A | 8/1988 | Goeddel et al. | |
| 4,832,959 A | 5/1989 | Engels et al. | |
| 4,835,256 A | 5/1989 | Taniguchi et al. | |
| 4,845,196 A | 7/1989 | Cowling | |
| 4,855,238 A | 8/1989 | Gray et al. | |
| 4,897,471 A | 1/1990 | Stabinsky | |
| 4,898,931 A | 2/1990 | Itoh et al. | |
| 4,904,584 A | 2/1990 | Shaw | |
| 4,921,698 A | 5/1990 | Shirai et al. | |
| 4,925,793 A | 5/1990 | Goeddel et al. | |
| 4,929,554 A | 5/1990 | Goeddel et al. | |
| 4,944,941 A | 7/1990 | Ammann | |
| 4,966,843 A | 10/1990 | McCormick et al. | |
| 4,980,455 A | 12/1990 | Sakaguchi et al. | |
| 5,004,689 A | 4/1991 | Fiers et al. | |
| 5,041,376 A | 8/1991 | Gething et al. | |
| 5,096,705 A | 3/1992 | Goeddel et al. | |
| 5,109,120 A | 4/1992 | Ueno et al. | |
| 5,157,004 A | 10/1992 | Sakaguchi et al. | |
| 5,362,490 A | 11/1994 | Kurimoto et al. | |
| 5,376,567 A | 12/1994 | McCormick et al. | |
| 5,382,657 A | 1/1995 | Karasiewicz et al. | |
| 5,518,899 A | 5/1996 | Kurimoto et al. | |
| 5,541,293 A | 7/1996 | Stabinsky | |
| 5,554,515 A | 9/1996 | Kurimoto et al. | |
| 5,574,137 A | 11/1996 | Gray et al. | |
| 5,582,824 A | 12/1996 | Goeddel et al. | |
| 5,595,888 A | 1/1997 | Gray et al. | |
| 5,661,009 A | 8/1997 | Stabinsky | |

(Continued)

FOREIGN PATENT DOCUMENTS

CA    2 096 532    5/1992

(Continued)

OTHER PUBLICATIONS

Phillips, A. the Cahllenge of gene therapy and DNA delivery (2001), J. Pharm. and Pharmacology 53, pp. 1169-1174.*

(Continued)

*Primary Examiner*—Christine J Saoud
*Assistant Examiner*—Jegatheesan Seharaseyon
(74) *Attorney, Agent, or Firm*—Sharon M. Fujita; Donald J. Pochopien; Norman J. Kruse

(57) ABSTRACT

The present invention relates to novel full-length interferon gamma (IFNG) polypeptide variants having interferon gamma activity. The full-length interferon gamma polypeptide variants of the invention are obtained by performing selected modifications in the C-terminal part of the molecule. The full-length interferon gamma polypeptide variants of the invention are useful in therapy, in particular for the treatment of interstitial pulmonary diseases, such as idiopathic pulmonary fibrosis.

48 Claims, 13 Drawing Sheets

U.S. PATENT DOCUMENTS

Figure 1:
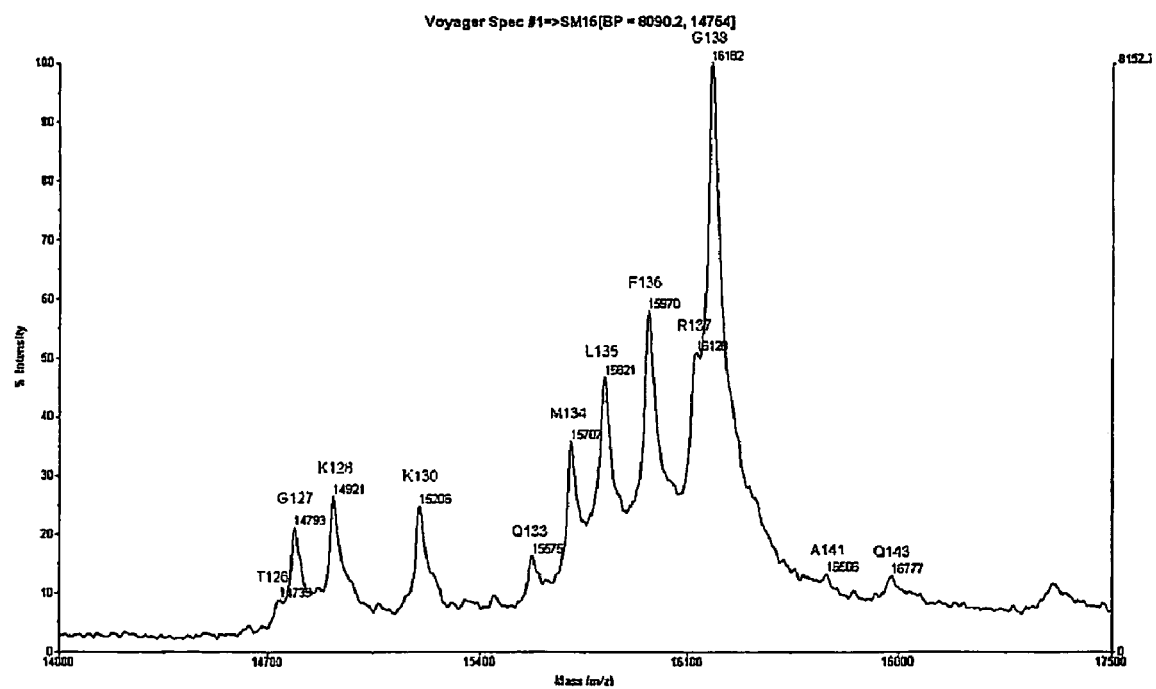

| | | | |
|---|---|---|---|
| 5,672,692 | A | 9/1997 | Kurimoto et al. |
| 5,690,925 | A | 11/1997 | Gray et al. |
| 5,711,944 | A | 1/1998 | Gilbert et al. |
| 5,723,121 | A | 3/1998 | Takenaga et al. |
| 5,738,846 | A | 4/1998 | Greenwald et al. |
| 5,747,646 | A | 5/1998 | Hakimi et al. |
| 5,770,191 | A | 6/1998 | Johnson et al. |
| 5,792,834 | A | 8/1998 | Hakimi et al. |
| 6,042,822 | A | 3/2000 | Gilbert et al. |
| 6,046,034 | A | 4/2000 | Waschutza et al. |
| 6,120,762 | A | 9/2000 | Johnson et al. |
| 6,497,871 | B1 | 12/2002 | Gray et al. |

FOREIGN PATENT DOCUMENTS

| | | |
|---|---|---|
| EP | 077 670 B1 | 4/1983 |
| EP | 088 540 A2 | 9/1983 |
| EP | 089 676 A2 | 9/1983 |
| EP | 098 110 A2 | 1/1984 |
| EP | 110 044 A1 | 6/1984 |
| EP | 146 354 A2 | 6/1985 |
| EP | 158 198 A1 | 10/1985 |
| EP | 170 917 B1 | 2/1986 |
| EP | 219 781 A2 | 4/1987 |
| EP | 229 108 B1 | 7/1987 |
| EP | 256 424 B1 | 8/1987 |
| EP | 236 987 B1 | 9/1987 |
| EP | 237 019 A2 | 9/1987 |
| EP | 306 870 A2 | 3/1989 |
| EP | 121 157 B1 | 6/1989 |
| EP | 145 174 B1 | 9/1989 |
| EP | 370 205 A2 | 5/1990 |
| EP | 446 582 B1 | 9/1991 |
| EP | 546 099 B1 | 10/1994 |
| EP | 795 332 A2 | 9/1997 |
| EP | 593 868 B1 | 4/1998 |
| EP | 860 442 A1 | 8/1998 |
| WO | 92/08737 A1 | 11/1991 |
| WO | 92/22310 A1 | 6/1992 |
| WO | 99/03887 A1 | 7/1998 |
| WO | 99/67291 A2 | 6/1999 |
| WO | 01/23006 A1 | 9/2000 |
| WO | 01/36001 A2 | 11/2000 |

OTHER PUBLICATIONS

Arakawa, et al., *Role of Polycationic c-terminal Portion in the Structure and Activity of Recombinant Human Interferon-γ*, The Journal of Biological Chemistry, 261(18), Jun. 25, pp. 8534-8539 (1986).

Arakawa, et al., *Structure and Activity of Glycosylated Human Interferon-γ*, Journal of Interferon Research, 6:687-695 (1986).

Bulleid, et al., *Source of heterogeneity in secreted interferon-γ*, Biochem. J. 268:777-781 (1990).

Cantell, et al., *Differential Inactivation of Interferon by a Protease from Human Granulocytes*, Journal of Interferon Research 12:177-183 (1992).

Castro, et al., *The macroheterogeneity of recombinant human interferon-γ produced by Chinese-hamster ovary cells is affected by the protein and lipid content of the culture medium*, Biotechnol. Appl. Biochem., 21:87-100 (1995).

Curling, et al., *Recombinant human interferon-γ, Differences in glycosylation and proteolytic processing lead to heterogeneity in batch culture*, Biochem. J., 272:333-337 (1990).

Devos, et al., *Molecular cloning of human immune interferon cDNA and its expression in eukaryotic cells*, Nucleic Acids Research, 10(8), 2487-2501, Nov. 8, 1982.

Ealick, et al., *Three-Dimensional Structure of Recombinant Human Interferon-γ*, Science, 252:698-702 (1991).

Farrar, et al., *The Molecular Cell Biology of Interferon-γ and its Receptor*, Annu. Rev. Immunol. 11:572-611 (1993).

Gray, et al., *Structure of the human immune interferon gene*, Nature, 298:859-863 (Aug. 1992).

Griggs, et al., *The N-terminus and C-Terminus of IFN-γ Are Binding Domains for Cloned Soluble IFN-γ Receptor*, The Journal of Immunology, 149(2) 517-520 (Jul. 15, 1992).

Gu, et al., *Improvement of Interferon-γ Sialylation in Chinese Hamster Ovary Cell culture by Feeding of N-Acetylmannosamine*, Biotechnology & Bioengineering, 58(6) 642-648 (1998).

Haelewn, et al., *Interaction of truncated human interferon γ variants with the interferon γ receptor: crucial importance of Arg-129*, Biochem. J., 324, 591-595 (1997).

Harmon, et al., *Rapid Monitoring of Site-Specific Glycosylation Microheterogeneity of Recombinant Human Interferon-γ*, Anal. Chem., 68(9) 1465-1473 (1996).

Hogrefe, et al., *Amino Terminus Is Essential to the Structural Integrity of Recombinant Human Interferon-γ*, The Journal of Biological Chemistry, 264(21) 12179-86 (1989).

Hooker, et al., *Constraints on the Transport and Glycosylation of Recombinant IFN-γ in Chinese Hamster Ovary and Insect Cells*, Biotechnology & Bioengineering, 63(5) 559-572 (1999).

Hsu, et al., *Structure and activity of Recombinant Human Interferon-γ Analogs*, Journal of Interferon Research, 6:663-670 (1986).

James, et al., *N-Glycosylation of Recombinant Human Interferon-γ Produced in Different Animal Expression Systems*, Bio/Technology, 13:592-96 (Jun. 13, 1995).

Kita, et al., *Characterization of a Polyethylene Glycol Conjugate of Recombinant Human Interferon-γ*, Drug Design and Delivery, 6:157-167 (1990).

Kontsek, et al., *Engineered Acid-Stable Human Interferon Gamma*, Cytokine, 12(6) 708-710 (Jun. 2000).

Landar, et al., *Design, Characterization, and Structure of a Biologically Active Single-chain Mutant of Human IFN-γ*, J. Mol. Biol., 299:169-179 (2000).

Leinikki, et al., *Reduced Receptor Binding by a Human Interferon-γ Fragment Lacking 11 Carboxyl-Terminal Amino Acids*, Journal of Immunology, 139(10) 3360-3366 (1987).

Littman, et al., *Binding of Unglycosylated and Glycosylated Human Recombinant Interferon-γ to Cellular Receptors*, Journal of Interferon Research, 5: 471-476 (1985).

Lord, et al., *Functional Domains of Human Interferon Gamma Probed With Antipeptide Antibodies*, Molecular Immunology, 26(7) 637-640 (1989).

Luk, et al., *Structure-Function Analysis of the Human Interferon γ*, The Journal of Biological Chemistry, 265 (22) 13314-13319 (1990).

Lundell, et al., *Importance of the Loop connecting A and B Helices of Human Interferon-γ in Recognition by Interferon-γ Receptor*, The Journal of Biological Chemistry, 269(23) 16159-16162.

Lundell, et al., *Structural Elements Required for Receptor Recognition of Human Interferon-Gamma*, Pharmac. Ther. 64:1-21 (1994).

Lundell, et al., *The carboxyl-terminal region of human interferon γ is important for biological activity: mutagenic and NMR analysis*, Protein Engineering, 4(3) 335-341 (1991).

Lunn, et al., *A point mutation of human interferon γ abolishes receptor recognition*, Protein Engineering, 5(3) 253-257 (1992).

Lunn, et al., *A point mutation that decreases the thermal stability of human interferon γ*, Protein Engineering, 5(3) 249-252 (1992).

Mortz, et al., *Mass spectrometric characterization of glycosylated interferon-γ variants separated by gel electrophoresis*, Electrophoresis, 17:926-931 (1996).

Nishi, et al., *Cloning and Expression of a Novel Variant of Human Interferon-γ cDNA*, J. Biochem, 97 (1) 153-159 (1985).

Nyberg, et al., *Metabolic Effects on Recombinant Interferon-γ Glycosylation in Continuous Culture of Chinese Hamster Ovary Cells*, Biotechnology & Bioengineering, 62(3) 336-347 (1999).

Oliver, et al., *The use of electrospray ionization MS to determine the structure of glycans in intact glycoproteins*, Biochem. Mass Spectro., 24:917-927 (1996).

Pan, et al., *Structural characterization of human interferon γ*, FEBS 145-149 (1987).

Rinderknecht, et al., *Natural Human Interferon-γ*, Journal of Biological Chemistry, 259(11) 6790-6797 (1984).

Riske, et al., *Characterization of Human Interferon-γ and Human Interleukin-2 from Recombinant Mammalian Cell Lines and Peripheral Blood Lymphocytes*, Lymphokine and Cytokine Research, 10(3) 213-218, (1991).

Sakaguchi, et al., *Human interferon-γ lacking 23 COOH-terminal amino acids is biologically active*, FEBS Letters, 230(1,2) 201-204 (Mar. 1988).

Sano, et al., *Structural Characterization of Recombinant Human Interferon-Gammas Derived from Two Different Mammalian Cells*, Microbiol. Immunol., 32 (5) 499-510 (1988).

Sareneva, et al., *Biosynthesis and N-glycosylation of human interferon-γ Asn25 and Asn97 differ markedly in how efficiently they are glycosylated and in their oligosaccharide composition*, Eur. J. Biochem., 242:191-200 (1996).

Sareneva, et al., *N-glycosylation of human interferon-γ: glycans at Asn-25 are critical for protease resistance*, Biochem. J. 308:9-14 (1995).

Sareneva, et al., *Role of N-glycosylation in the synthesis, dimerization and secretion of human interferon-γ*, Biochem. J., 303:831-840 (1994).

Sareneva, et al., *Effect of Carbohydrates on the Pharmacokinetics of Human Interferon-γ*, Journal of Interferon Research, 13:267-269 (1993).

Seelig, et al., *Evidence for a Polypeptide Segment at the Carboxyl Terminus of Recombinant Human γ Interferon Involved in Expression of Biological Activity*, Biochemistry, 27(6) 1981-1987 (1988).

Slodowski, et al., *Carboxy-terminal truncated rhuIFN-γ with a substitution of Gln133 o Ser132 to leucine leads to higher biological activity than in the wild type*, Euro. J. Biochem, 202:1133-1140 (1991).

Subramaniam, et al., *The Carboxyl Terminus of Interferon-γ Contains a Functional Polybasic Nuclear Localization Sequence*, Journal of Biological Chemistry, 274(1) 403-407 (1999).

Tang, et al., *Studies on the PEGylation of Protein at a Specific Site: Sulfhydryl-PEGylation of 97 Cys-IFN-γ*, Acta Biochimica et Biophysica Sinica, 28(3) 1-5 (May 1996).

Taya, et al., *Cloning and structure of the human immune interferon-γ chromosomal gene*, The EMBO Journal, 1(8) 953-958 (1982).

Trousdale, et al., *Human Alpha and Gamma Interferon Analogs in Rabbits with Herpetic Keratitis*, Invest. Ophth. & Vis. Sci., 26(9) 1244-1251 (1985).

Waschütza, et al., *Interferon-γ variants with deletions in the AB surface loop*, Eur. J. Biochem., 256:303-309 (1998).

Wetzel, et al., *Mutations in Human Interferon Gamma Affecting Inclusion Body Formation Identified by a General Immunochemical Screen*, Bio/Technology, 9:731-737 (1991).

Zhang, et al., *Quantitative analysis and process monitoring of site-specific glycosylation microheterogeneity in recombinant human interferon-γ from Chinese hamster ovary cell culture by hydrophilic interaction chromatography*, Journal of Chromatogr. B, 712:73-82 (1998).

Ziesche, et al., *A Preliminary Study of Long-Term Treatment with Interferon Gamma-1b and Low-Dose Prednisolone in Patients with Idiopathic Pulmonary Fibrosis*, The New England Journal of Medicine, 341(7) 1264-1269 (1999).

Wetzel, et al., *Mutational Analysis of the C-terminus of Hyman Interferon-γ*, Protein Engineering, 3:(7) pp. 611-623 (1990).

Alberts, et al., *Molecular Biology of the Cell*, 1989.

* cited by examiner

FULL-LENGTH INTERFERON GAMMA POLYPEPTIDE VARIANTS

CROSS REFERENCE TO RELATED APPLICATIONS

This application is a 371 of PCT/DK 03/00426, filed Jun. 23, 2003, which claims priority under 35 U.S.C. § 120 to U.S. provisional application Ser. No. 60/417,399, filed Oct. 9, 2002, and to U.S. provisional application Ser. No. 60/415,214, filed Sep. 30, 2002, and to U.S. provisional application Ser. No. 60/394,120, filed Jul. 3, 2002.

FIELD OF THE INVENTION

The present invention relates to novel full-length interferon gamma polypeptide variants having interferon gamma (IFNG) activity, methods for their preparation, pharmaceutical compositions comprising the variants and their use in the treatment of diseases, in particular for the treatment of interstitial pulmonary diseases, such as idiopathic pulmonary fibrosis.

BACKGROUND OF THE INVENTION

Interferon gamma (IFNG) is a cytokine produced by T-lymphocytes and natural killer cells and exists as a homodimer of two noncovalently bound polypeptide subunits. The mature form of each monomer comprises 143 amino acid residues (shown in SEQ ID NO:1) and the precursor form thereof, including the signal sequence, comprises 166 amino acid residues (shown in SEQ ID NO:2).

Each subunit has two potential N-glycosylation sites (Aggarwal et al., Human Cytokines, Blackwell Scientific Publications, 1992) at positions 25 and 97. Depending on the degree of glycosylation the molecular weight of IFNG in dimer form is 34-50 kDa (Farrar et al., Ann. Rev. Immunol, 1993, 11:571-611).

The primary sequence of wild-type human IFNG (huIFNG) was reported by Gray et al. (Nature 298:859-863, 1982), Taya et al. (EMBO J. 1:953-958, 1982), Devos et al. (Nucleic Acids Res. 10:2487-2501, 1982) and Rinderknecht et al. (J. Biol. Chem. 259:6790-6797, 1984), and in EP 77670, EP 89676 and EP 110044.

Experimental 3D structures of huIFNG determined by X-ray crystallography have been reported by Ealick et al. Science 252:698-702 (1991) who reported the C-alpha trace of an IFNG homodimer. Walter et al. Nature 376:230-235 (1995) disclosed the structure of an IFNG homodimer in complex with two molecules of a soluble form of the IFNG receptor. The coordinates of this structure, however, have never been made publicly available. Thiel et al. Structure 8:927-936 (2000) showed the structure of an IFNG homodimer in complex with two molecules of a soluble form of the IFNG receptor having a third molecule of the receptor in the structure not making interactions with the IFNG homodimer.

Various naturally-occurring or mutated forms of the IFNG subunit polypeptides have been reported, including one comprising a Cys-Tyr-Cys N-terminal amino acid sequence (positions (−3)-(−1) relative to SEQ ID NO:1), one comprising an N-terminal methionine (position −1 relative to SEQ ID NO:1), and various C-terminally truncated forms comprising 127-134 amino acid residues. It is known that 1-15 amino acid residues may be deleted from the C-terminus without abolishing IFNG activity of the molecule. Furthermore, heterogeneity of the huIFNG C-terminus was described by Pan et al. (Eur. J. Biochem. 166:145-149, 1987).

Glycosylation variation in huIFNG has been reported by Curling et al. (Biochem. J. 272:333-337, 1990) and Hooker et al., (J. of Interferon and Cytokine Research, 1998, 18: 287-295).

Polymer-modification of huIFNG was reported by Kita et al. (Drug Des. Deliv. 6:157-167, 1990), and in EP 236987 and U.S. Pat. No. 5,109,120.

WO 99/03887 discloses PEGylated variants of polypeptides belonging to the growth hormone superfamily, wherein a non-essential amino acid residue located in a specified region of the polypeptide has been replaced by a cysteine residue. IFNG is mentioned as one example of a member of the growth hormone super family, but modification thereof is not discussed in any detail.

WO 01/36001 discloses novel IFNG conjugates comprising a non-polypeptide moiety attached to an IFNG polypeptide which have been modified by introduction and/or deletion of attachment sites for such non-polypeptide moieties, e.g. PEG and glycosylation sites. These molecules have improved properties, such as improved half-life and/or increased bioavailablity.

IFNG has been suggested for treatment of interstitial lung diseases (also known as Interstitial Pulmonary Fibrosis (IPF)) (Ziesche et al. (N. Engl. J. Med. 341:1264-1269, 1999 and Chest 110:Suppl:25S, 1996) and EP 0 795 332) for which purpose IFNG can be used in combination with prednisolone. In addition to IPF, granulomatous diseases (Bolinger et al, Clinical Pharmacy, 1992, 11:834-850), certain mycobacterial infections (N. Engl. J. Med. 330:1348-1355, 1994), kidney cancer (J. Urol. 152:841-845, 1994), osteopetrosis (N. Engl. J. Med. 332:1594-1599, 1995), scleroderma (J. Rheumatol. 23:654-658, 1996), hepatitis B (Hepatogastroenterology 45:2282-2294, 1998), hepatitis C (Int. Hepatol. Communic. 6:264-273, 1997), septic shock (Nature Medicine 3:678-681, 1997), and rheumatoid arthritis may be treated with IFNG. Furthermore, IFNG is presently being clinically evaluated for treatment of ovarian cancer, liver fibrosis, asthma and lymphoma.

As a pharmaceutical compound huIFNG is used with a certain success, above all, against some viral infections and tumors. huIFNG is usually applicable via parenteral, preferably via subcutaneous, injection. Maximum serum concentrations have been found after seven hours. It has been reported that the half-life in plasma is 30 minutes after intravenous administration. For this reason efficient treatment with huIFNG involves frequent injections.

The main adverse effects consist of fever, chills, sweating, headache, myalgia and drowsiness. These effects are associated with injecting huIFNG and are observed within the first hours after injection. Rare side effects are local pain and erythema, elevation of liver enzymes, reversible granulo- and thrombopenia and cardiotoxicity.

It is known that when IFNG is produced in mammalian cell lines a heterogenous population of IFNG polypeptides is obtained due to C-terminal truncation of the IFNG polypeptide (reviewed in Lundell et al. *Pharmac. Ther.* 64, 1-21, 1994). Clearly, this constitutes a severe problem in that valuable polypeptide material is lost and, further, it is necessary to carry out time-consuming and cumbersome purification in order to obtain a homogenous population of IFNG polypeptides having the desired length. Most likely, this truncation is effected by endo- and/or exoprotease activity present in the cell. The present inventors have solved the above-mentioned problem by performing selected modifications in the C-terminal part of the IFNG polypeptide. By performing such modifications C-terminal truncation is avoided and, consequently, the truncation can be controlled and homogenous populations of full-length IFNG polypeptides can be obtained.

Thus, it is an object of the present invention to provide novel full-length IFNG polypeptides, which are not prone to C-terminal truncation during production or storage.

BRIEF DISCLOSURE OF THE INVENTION

In a first aspect the present invention relates to a full-length interferon gamma (IFNG) polypeptide variant exhibiting IFNG activity, wherein said variant comprises
(a) at least one amino acid substitution in a position selected from the group consisting of S132 and S142; and
(b) at least one amino acid substitution in a position selected from the group consisting of R137, R139 and R140.

In a second aspect the present invention relates to a full-length interferon gamma (IFNG) polypeptide variant exhibiting IFNG activity, wherein said variant comprises an amino acid substitution in position R137 and an amino acid substitution in position R140.

In further aspects the invention relates to means and methods for preparing an IFNG polypeptide variant of the invention, including nucleotide sequences and expression vectors encoding the variant as well as host cells comprising the vector or nucleotide sequence of the invention.

In even further aspects the present invention relates to a pharmaceutical composition comprising the variant of the invention and a pharmaceutically acceptable diluent, carrier or adjuvant; to a variant of the invention for use as a medicament; to use of a variant of the invention for the manufacture of a medicament for the treatment of interstitial pulmonary diseases as well as to a method for treating or preventing interstitial pulmonary diseases, said method comprising administering to a mammal, in particular a human being, in need thereof an effective amount of a variant of the invention.

In still another aspect the present invention relates to a method for producing a full-length IFNG polypeptide, said method comprising i) cultivating a host cell according to the invention under conditions suitable for production of the IFNG polypeptide, and ii) recovering the IFNG polypeptide.

Other aspects of the invention will become apparent from the below disclosure.

BREIF DESCRIPTION OF THE DRAWINGS

FIG. 1 shows a MALDI-TOF mass spectra of [E38N+S40T+S99T]huIFNG purified from culture media by diafiltration followed by cation exchange, immunoprecipitation and de-glycosylation with PNGase F. See Example 8 for further details.

FIG. 2 shows a MALDI-TOF mass spectra of [E38N+S40T+S99T+R137P]huIFNG purified from culture media by diafiltration followed by cation exchange, immmunoprecipitation and de-glycosylation with PNGase F. See Example 8 for further details.

FIG. 3 shows a MALDI-TOF mass spectra of [E38N+S40T+S99T+R139P]huIFNG purified from culture media by diafiltration followed by cation exchange, immunoprecipitation and de-glycosylation with PNGase F. See Example 8 for further details.

FIG. 4 shows a MALDI-TOF mass spectra of [E38N+S40T+S99T+S142P]huIFNG purified from culture media by diafiltration followed by cation exchange, immunoprecipitation and de-glycosylation with PNGase F. See Example 8 for further details.

FIG. 5 shows a MALDI-TOF mass spectra of [E38N+S40T+S99T+Q143P]huIFNG purified from culture media by diafiltration followed by cation exchange, immunoprecipitation and de-glycosylation with PNGase F. See Example 8 for further details.

FIG. 6 shows a MALDI-TOP mass spectra of [E38N+S40T+S99T+R137P+R139P]huIFNG purified from culture media by diafiltration followed by cation exchange, immunoprecipitation and de-glycosylation with PNGase F. See Example 8 for further details.

FIG. 7 shows a MALDI-TOF mass spectra of [E38N+S40T+S99T+R137P+R139P+Q143P]huIFNG purified from culture media by diafiltration followed by cation exchange, immunoprecipitation and de-glycosylation with PNGase F. See Example 8 for further details.

FIG. 8 shows a MALDI-TOF mass spectra of [E38N+S40T+S99T+R137P+R139P+S142P]huIFNG purified from culture media by diafiltration followed by cation exchange, immunoprecipitation and de-glycosylation with PNGase F. See Example 8 for further details.

FIG. 9 shows a MALDI-TOF mass spectra of [E38N+S40T+S99T+R137P+S142P]huIFNG purified from culture media by diafiltration followed by cation exchange, immunoprecipitation and de-glycosylation with PNGase F. See Example 8 for further details.

FIG. 10 shows a MALDI-TOF mass spectra of [E38N+S40T+S99T+S132P+R137P+R140P]huIFNG purified from culture media by diafiltration followed by cation exchange, immunoprecipitation and de-glycosylation with PNGase F. See Example 8 for further details.

FIG. 11 shows a MALDI-TOF mass spectra of [E38N+S40T+S99T+S132P+R140P]huIFNG purified from culture media by diafiltration followed by cation exchange, immunoprecipitation and de-glycosylation with PNGase F. See Example 8 for further details.

FIG. 12 shows a MALDI-TOF mass spectra of [E38N+S40T+S99T+R140P]huIFNG purified from culture media by diafiltration followed by cation exchange, immunoprecipitation and de-glycosylation with PNGase F. See Example 8 for further details.

FIG. 13 shows a MALDI-TOF mass spectra of [E38N+S40T+S99T+R137P+R140P]huIFNG purified from culture media by diafiltration followed by cation exchange, immunoprecipitation and de-glycosylation with PNGase F. See Example 8 for further details.

DETAILED DESCRIPTION OF THE INVENTION

Definitions

In the context of the present application and invention the following definitions apply:

The term "conjugate" (or interchangeably "conjugated polypeptide") is intended to indicate a heterogeneous (in the sense of composite or chimeric) molecule formed by the covalent attachment of one or more polypeptide variant(s) to one or more non-polypeptide moieties. The term covalent attachment means that the polypeptide variant and the non-polypeptide moiety are either directly covalently joined to one another, or else are indirectly covalently joined to one another through an intervening moiety or moieties, such as a bridge, spacer, or linkage moiety or moieties. Preferably, a conjugated polypeptide variant is soluble at relevant concentrations and conditions, i.e. soluble in physiological fluids such as blood. Examples of conjugated polypeptide variants of the invention include glycosylated and/or PEGylated polypeptides. The term "non-conjugated polypeptide" may be used about the polypeptide part of the conjugated polypeptide variant.

tion site" are used interchangeably herein. An "O-glycosylation site" is the OH-group of a serine or threonine residue.

The term "attachment group" is intended to indicate an amino acid residue group capable of coupling to the relevant non-polypeptide moiety such as a polymer molecule or a sugar moiety. Useful attachment groups and their matching non-polypeptide moieties are apparent from the table below.

| Attachment group | Amino acid | Examples of non-polypeptide moiety | Conjugation method/activated PEG | Reference |
|---|---|---|---|---|
| —NH$_2$ | N-terminal, Lys | Polymer, e.g. PEG | mPEG-SPA Tresylated mPEG | Shearwater Inc. Delgado et al, critical reviews in Therapeutic Drug Carrier Systems 9(3, 4): 249-304 (1992) |
| —COOH | C-term, Asp, Glu | Polymer, e.g. PEG Sugar moiety | mPEG-Hz In vitro coupling | Shearwater Inc |
| —SH | Cys | Polymer, e.g. PEG, Sugar moiety | PEG-vinylsulphone PEG-maleimide In vitro coupling | Shearwater Inc Delgado et al, critical reviews in Therapeutic Drug Carrier Systems 9(3, 4): 249-304 (1992) |
| —OH | Ser, Thr, OH—, Lys | Sugar moiety | In vivo O-linked glycosylation | |
| —CONH$_2$ | Asn as part of an N-glycosylation site | Sugar moiety | In vivo glycosylation | |
| Aromatic residue | Phe, Tyr, Trp | Sugar moiety | In vitro coupling | |
| —CONH$_2$ | Gln | Sugar moiety | In vitro coupling | Yan and Wold, Biochemistry, 1984, Jul 31; 23(16): 3759-65 |
| Aldehyde Ketone | Oxidized carbohydrate | Polymer, e.g. PEG, PEG-hydrazide | PEGylation | Andresz et al., 1978, Makromol. Chem. 179: 301; WO 92/16555, WO 00/23114 |
| Guanidino | Arg | Sugar moiety | In vitro coupling | Lundblad and Noyes, Chemical Reagents for Protein Modification, CRC Press Inc. Boca Raton, FL |
| Imidazole ring | His | Sugar moiety | In vitro coupling | As for guanidine |

The term "non-polypeptide moiety" is intended to indicate a molecule that is capable of conjugating to an attachment group of the IFNG variant. Examples of such molecules include polymer molecules, lipophilic compounds, sugar moieties or organic derivatizing agents. Prefererred examples include polymer molecules, such as PEG, and sugar moieties. It will be understood that the non-polypeptide moiety is linked to the variant through an attachment group of the variant. Except where the number of non-polypeptide moieties, such as polymer molecule(s), attached to the IFNG variant is expressly indicated every reference to "a non-polypeptide moiety" attached to the IFNG variant or otherwise used in the present invention shall be a reference to one or more non-polypeptide moieties attached to the IFNG variant.

The term "polymer molecule" is defined as a molecule formed by covalent linkage of two or more monomers, wherein none of the monomers is an amino acid residue. The term "polymer" may be used interchangeably with the term "polymer molecule".

The term "sugar moiety" is intended to indicate a carbohydrate molecule attached by in vivo or in vitro glycosylation, such as N- or O-glycosylation.

An "N-glycosylation site" has the sequence N-X-S/T/C", wherein X is any amino acid residue except proline, N is asparagine and S/T/C is either serine, threonine or cysteine, preferably serine or threonine, and most preferably threonine. The terms "N-glycosylation site" and "in vivo N-glycosyla- For in vivo N-glycosylation, the term "attachment group" is used in an unconventional way to indicate the amino acid residues constituting an N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the IFNG polypeptide is to be understood as one, two or all of the amino acid residues constituting an N-glycosylation site is/are to be altered in such a manner that either a functional N-glycosylation site is introduced into the amino acid sequence, removed from said sequence or a functional N-glycosylation site is retained in the amino acid sequence (e.g. by substituting a serine residue, which already constitutes part of an N-glycosylation site, with a threonine residue and vice versa).

In the present application, amino acid names and atom names (e.g. CA, CB, CD, CG, SG, NZ, N, O, C, etc) are used as defined by the Protein DataBank (PDB) which are based on the IUPAC nomenclature (IUPAC Nomenclature and Symbolism for Amino Acids and Peptides (residue names, atom names etc.),*Eur. J. Biochem.*, 138, 9-37 (1984) together with their corrections in *Eur. J Biochem.*, 152, 1(1985). CA is sometimes referred to as Cα, CB as Cβ. The term "amino acid residue" is intended to indicate an amino acid residue contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

Numbering of amino acid residues in this document is from the N-terminus of wild-type human IFNG (huIFNG) without signal peptide (SEQ ID NO:1).

The terminology used for identifying amino acid positions/substitutions is illustrated as follows: G18 indicates that position 18 is occupied by a glycine residue. G18N indicates that the Gly residue of position 18 has been replaced with an Asn residue. Multiple substitutions are indicated with a "+", e.g. G18N+S20T means an amino acid sequence which comprises a substitution of the Gly residue in position 18 with an Asn residue and a substitution of the Ser residue in position 20 with a Thr residue. Alternative substitutions are indicated with a "/". For example, G18S/T covers the following individual substitutions: G18S and G18T. Deletions are indicated by an asterix. For example, G18* indicates that the Gly residue in position 18 has been deleted. Insertions are indicated the following way: Insertion of an additional Pro residue after the Gln residue located at position 143 is indicated as Q143QP. Combined substitutions and insertions are indicated in the following way: substitution of the Gln residue at position 143 with a Cys residue and insertion of a Pro residue after the position 143 amino acid residue is indicated as Q143CP.

The term "nucleotide sequence" is intended to indicate a consecutive stretch of two or more nucleotide molecules. The nucleotide sequence may be of genomic, cDNA, RNA, semi-synthetic, synthetic origin, or any combinations thereof.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

"Cell", "host cell", "cell line" and "cell culture" are used interchangeably herein and all such terms should be understood to include progeny resulting from growth or culturing of a cell.

"Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "modification", as used herein, covers amino acid substitutions, amino acid insertions and amino acid deletions.

The terms "mutation" and "substitution" are used interchangeably herein.

The term "introduce" is primarily intended to mean substitution of an existing amino acid residue, but may also mean insertion of an additional amino acid residue.

The term "remove" is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "one difference" or "differs from" as used in connection with specific modifications is intended to allow for additional differences being present apart from the specified amino acid modification. Thus, in addition to the substitutions performed in the C-terminal part of the IFNG polypeptide aiming at controlling the C-terminal truncation of the IFNG polypeptide, the IFNG variant may, if desired, comprise other modifications that are not related to this property. Such other modifications may, for example, include introduction and/or removal of amino acid residues comprising an attachment group for a non-polypeptide moiety, addition of one or more extra residues at the N-terminus, e.g. addition of a Met residue at the N-terminus or addition of the amino acid sequence Cys-Tyr-Cys at the N-terminus, as well as "conservative amino acid substitutions", i.e. substitutions performed within groups of amino acids with similar characteristics, e.g. small amino acids, acidic amino acids, polar amino acids, basic amino acids, hydrophobic amino acids and aromatic amino acids. Examples of conservative substitutions in the present invention may, in particular, be selected from the groups listed in the table below.

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

The term "at least one" as used about a non-polypeptide moiety, an amino acid residue, a substitution, etc. is intended to mean one or more.

The term "$AUC_{sc}$" or "Area Under the Curve when administered subcutaneously" is used in its normal meaning, i.e. as the area under the IFNG activity in serum-time curve, where the IFNG variant has been administered subcutaneously, in particular when administered subcutaneously in rats or non-human primates, such as monkeys. Once the experimental IFNG activity-time points have been determined, the $AUC_{sc}$ may conveniently be calculated by a computer program, such as GraphPad Prism 3.01.

The term "functional in vivo half-life" is used in its normal meaning, i.e. the time at which 50% of the biological activity of the polypeptide is still present in the body/target organ, or the time at which the activity of the polypeptide is 50% of the initial value. The functional in vivo half-life may by determined in rats, cf. the Materials and Method section herein, but is preferably determined in non-human primates, such as monkeys. It is important to note that the term "functional in vivo half-life", when used herein, for a given IFNG variant must be determined for a sample that has been administered intravenously (iv).

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The serum half-life may be determined in rats, cf. the Materials and Method section herein, but is preferably determined in non-human primates, such as monkeys. It is important to note that the term "serum half-life", when used herein, for a given IFNG variant must be determined for a sample that has been administered intravenously (iv).

If not further specified, the terms "half-life" or "in vivo half-life" may refer to both functional in vivo half-life and serum half-life.

The term "serum" is used in its normal meaning, i.e. the term covers blood plasma without fibrinogen and other clotting factors.

The polypeptide is normally cleared by the action of one or more of the reticuloendothelial systems (RES), kidney, spleen or liver, or by specific or unspecific proteolysis. The term "renal clearance" is used in its normal meaning to indicate any clearance taking place by the kidneys, e.g. by glomerular filtration, tubular excretion or tubular elimination. Normally, renal clearance depends on physical characteristics of the polypeptide, including molecular weight, size (relative to the cutoff for glomerular filtration), symmetry, shape/rigidity, charge and attached carbohydrate chains. A molecular weight of about 67 kDa is normally considered to be a cut-off-value for renal clearance. Renal clearance may be measured by any suitable assay, e.g. an established in vivo assay. For instance, renal clearance may be determined by administering a labelled (e.g. radiolabelled or fluorescence labelled) conjugated polypeptide to a patient and measuring the label activity in urine collected from the patient. Reduced renal clearance is determined relative to the reference molecule, such as glycosylated huIFNG, glycosylated [S99T]huIFNG or ACTIMMUNE® interferon gamma. The functionality to be retained is normally selected from antiviral, antiproliferative or immunomodulatory activity.

The term "increased" as used about the functional in vivo half-life or serum half-life is used to indicate that the relevant half-life of the IFNG variant is statistically significantly increased relative to that of a reference molecule, such as glycosylated huIFNG, glycosylated [S99T]huIFNG or Actimmune® determined under comparable conditions. Thus, interesting IFNG variants are such variants, which has an increased functional in vivo half-life or an increased serum half-life as compared to any of the reference molecules mentioned above, when administered intravenously.

The term "reduced immunogenicity" is intended to indicate that the IFNG variant gives rise to a measurably lower immune response than a reference molecule, e.g. glycosylated huIFNG or Actimmune®, as determined under comparable conditions. The immune response may be a cell or antibody mediated response (see, e.g., Roitt: Essential Immunology (8th Edition, Blackwell) for further definition of immunogenicity). Normally, reduced antibody reactivity is an indication of reduced immunogenicity. Reduced immunogenicity may be determined by use of any suitable method known in the art, e.g. in vivo or in vitro.

In the present context the term "increased degree of in vivo N-glycosylation" or "increased degree of N-glycosylation" is intended to indicate increased levels of attached carbohydrate molecules, normally obtained as a consequence of increased (or better) utilization of glycosylation site(s). It is well-known (Hooker et al., 1998, J. Interferon and Cytokine Res. 18, 287-295 and Sarenva et al., 1995, Biochem J., 308, 9-14) that when huIFNG is expressed in CHO cells only about 50% of the IFNG molecules utilizes both glycosylation sites, about 40% utilizes one glycosylation site (1N), and about 10% is not glycosylated (0N). The increased degree of in vivo N-glycosylation may be determined by any suitable method known in the art, e.g. by SDS-PAGE. One convenient assay for determining increased glycosylation is the method described in the section entitled "Determination of Increased Glycosylation" in the Materials and Methods section herein.

The term "exhibiting IFNG activity" is intended to indicate that the variant has one or more of the functions of native glycosylated huIFNG or ACTIMMUNE® interferon gamma, including the capability to bind to an IFNG receptor and cause transduction of the signal transduced upon huIFNG-binding of its receptor as determined in vitro or in vivo (i.e. in vitro or in vivo bioactivity). The IFNG receptor has been described by Aguet et al. (Cell 55:273-280, 1988) and Calderon et al. (Proc. Natl. Acad. Sci. USA 85:4837-4841, 1988). A suitable assay for testing IFNG activity is the assay entitled "Primary Assay" disclosed herein. When using the "Primary Assay" described herein, polypeptide variants "exhibiting IFNG activity" have a specific activity of at least 5% as compared to glycosylated huIFNG, glycosylated [S99T]huIFNG or ACTIMMUNE® interferon gamma. It will be understood that depending on which specific modifications are performed, for example whether the variant is PEGylated or not, this may lead to activities over a wide range. Thus, examples of specific activities may range from as low as 5% to as high as 150% as compared to glycosylated huIFNG, glycosylated [S99T]huIFNG or ACTIMMUNE® interferon gamma. For example, the specific activity may be at least 10% (e.g. 10-125%), such as at least 15% (e.g. 15-125%), e.g. at least 20% (such as 20-125%), at least 25% (e.g. 25-125%), at least 30% (e.g. 30-125%), at least 35% (e.g. 35-125%), at least 40% (e.g. 40-125%), at least 45% (e.g. 45-125%), at least 50% (e.g. 50-125%), at least 55% (e.g. 55-125%), at least 60% (e.g. 60-125%), at least 65% (e.g. 65-125%), at least 70% (e.g. 70-125%), at least 75% (e.g. 75-125%), at least 80% (e.g. 80-125%) or at least 90% (e.g. 90-110%) as compared to the specific activity of glycosylated huIFNG, glycosylated [S99T]huIFNG or ACTIMMUNE® interferon gamma.

It may be beneficial that the variant has a decreased receptor-binding affinity and hence a decreased IFNG activity as compared to glycosylated huIFNG, glycosylated [S99T] huIFNG or ACTIMMUNE® interferon gamma in order to decrease receptor-mediated clearence. For example, the variant may exhibit 1-75% (e.g. 5-75%), such as 1-50% (e.g. 5-50%), e.g. 1-40% (e.g. 5-40%), 1-30% (e.g. 5-30%), 1-20% (e.g. 5-20%) or 1-10% (e.g. 5-10%) of the IFNG activity of glycosylated huIFNG, glycosylated [S99T]huIFNG or ACTIMMUNE® interferon gamma when tested in the "Primary Assay" described herein.

An "IFNG polypeptide" is a polypeptide exhibiting IFNG activity, and is used herein about the polypeptide in monomer or dimeric form, as appropriate. For instance, when specific substitutions are indicated these are normally indicated relative to the IFNG polypeptide monomer. When reference is made to the IFNG polypeptide of the invention this is normally in dimeric form (and thus, e.g., comprises two IFNG polypeptide monomers modified as described). The dimeric form of the IFNG polypeptides may be provided by the normal association of two monomers or be in the form of a single chain dimeric IFNG polypeptide. It will be understood that the IFNG polypeptides of the invention may, in addition to the specified modifications, also contain other modifications, e.g. modifications, which increases the $AUC_{sc}$ and/or the functional in vivo half-life of the IFNG polypeptide. Thus, the term "IFNG polypeptide" also encompasses variant forms of the modified IFNG polypeptides disclosed herein. Specific examples of such variants, which, in addition to substitutions in the C-terminal part of the IFNG polypeptide, comprise further modifications include modifications such as S99T and E38N+S40T. More examples of suitable modifications are given below.

Normally, the variant forms of the IFNG polypeptide differs in 1-15 or 2-15 amino acid residues (such as in 1, 2, 3, 4, 5, 6, 7, 8, 9, 10, 11, 12, 13, 14 or 15 amino acid residues), e.g. in 1-10 or 2-10 amino acid residues, in 1-8 or 2-8 amino acid residues, in 1-5 or 2-5 amino acid residues, or in 1-3 or 2-3 amino acid residues compared to huIFNG shown in SEQ ID NO:1.

The term "functional site" is intended to indicate one or more amino acid residues which is/are essential for, or otherwise involved in, the function or performance of IFNG. Such amino acid residues are "located at" the functional site. The functional site may be determined by methods known in the art and is preferably identified by analysis of a structure of the polypeptide complexed to a relevant receptor, such as the IFNG receptor.

The term "huIFNG" is intended to mean the mature form of wild-type human IFNG having the amino sequence shown in SEQ ID NO:1, including huIFNG produced by recombinant means. If not further specified, the term "huIFNG" may refer to wild-type human IFNG in its glycosylated form (i.e. glycosylated at positions 25 and 97) or in its un-glycosylated form.

When used herein the term "glycosylated" indicates that the IFNG polypeptide is produced in a cell capable of glycosylating the polypeptide and, therefore, the IFNG polypeptide is glycosylated at its native N-glycosylation sites (position 25 and 97 of SEQ ID NO:1).

When used herein the term "un-glycosylated" indicates that the IFNG polypeptide is not glycosylated at its native N-glycosylation sites (position 25 and 97 of SEQ ID NO:1). Such "un-glycosylated" IFNG polypeptides may be obtained by producing the polypeptide in a prokaryotic host cell, such as *E. coli,* not capable of glycosylation.

It will be understood that when the terms "glycosylated" and "un-glycosylated" are used about the variant IFNG polypeptides of the invention, these terms indicate, independently of whether additional glycosylation sites have been introduced and/or removed, whether potential glycosylation sites of the IFNG polypeptide variants are utilized or not.

In the present context the term "full-length" is intended to mean that the variant is not truncated as compared to the parent polypeptide, which is modified according to the invention. Preferably, the parent protein to be modified as described herein is huIFNG. In this case the term "full-length" means that the variant contains 143 amino acid residues. Analogously, if the parent protein to be modified is Met-huIFNG, the term "full-length" mean that the variant contains 144 amino acid residues.

When used herein, the term "C-terminal part" covers the last 12 amino acid residues (calculated from the C-terminus) in huIFNG, i.e. amino acid residues S132-Q143.

When used herein the term "ACTIMMUNE®" refers to the 140 amino acid form of IFNG (disclosed in SEQ ID NO:3) achieved by fermentation of a genetically engineered *E.coli* bacterium. ACTIMMUNE® interferon gamma is un-glycosylated.

In the present context the term "non-positively charged amino acid residue" covers the following amino acid residues: A, V, L, I, M, F, W, P, G, S, T, C, Y, N, Q, D and E.

Interferon Gamma Variants of the Invention

Full-Length IFNG Variants

As indicated above, it has now been found that a substitution in either position S132 or position S142 in combination with at least substitution in a position selected from the group consisting of R137, R139 and R140, impedes the proteolytic processing of the polypeptide and hence results in a more homogenous product.

Thus, in a first aspect the present invention relates to a full-length IFNG polypeptide variant exhibiting IFNG activity, wherein said variant comprises (a) at least one substitution in a position selected from the group consisting of S132 and S142; and (b) at least one amino acid substitution in a position selected from the group consisting of R137, R139 and R140.

Furthermore, the present invention also relates to a substantially homogenous population of a full-length IFNG variant, wherein said full-length IFNG variant exhibits IFNG activity and wherein said full-length IFNG variant comprises (a) at least one substitution in a position selected from the group consisting of S132 and S142; and (b) at least one amino acid substitution in a position selected from the group consisting of R137, R139 and R140.

Moreover, the present invention also relates to a composition comprising a substantially homogenous population of a full-length IFNG variant, wherein said full-length IFNG variant exhibits IFNG activity and wherein said full-length IFNG variant comprises (a) at least one substitution in a position selected from the group consisting of S132 and S142; and (b) at least one amino acid substitution in a position selected from the group consisting of R137, R139 and R140.

When used herein, the term "substantially homogenous population" is defined as a population giving rise to a mass spectroscopic profile characterized by a single, dominant peak having an area under the curve (AUC) that is at least 3-fold higher than the AUC of any other peak appearing in the profile. Preferably, the AUC of the dominant peak is at least 4-fold higher, such as at least 5-fold higher than the AUC of any other peak appearing in the profile.

For example, the population of IFNG variants may contain at least 75% of the full-length IFNG variant of the invention (as compared to the total amount of IFNG variants in the population), preferably at least 80%, such as at least 85%, e.g. at least 90%, more preferably at least 95%, such as at least 96%, e.g. at least 97%, even more preferably at least 98%, such as at least 99%.

As will be understood the purpose of performing substitutions in one or more of the positions R137, R139 or R140 is to change the furin protease cleavage site and thereby avoiding proteolytic degradation of the polypeptide. Many furin proteases recognise the sequence R/K-X-R/K-R-↓-X, wherein X is any amino acid residue. Accordingly, R140 may be substituted with any amino acid residue, including lysine, and R137 and R139 may be substituted with any amino acid residue, except lysine. Preferably, the amino acid residue to be introduced in one or more of the positions R137, R139 and/or R140 is a non-positively charged amino acid residue.

Amino acid residue to be introduced in one or more of the positions R137, R139 and/or R140 may be selected from the group consisting of small amino acid residues, such as Ala, Gly, Ser, Cys and Thr; acidic amino acid residues, such as Asp and Glu; hydrophobic amino acid residues, such as Ile, Leu, Met, Pro and Val; aromatic amino acid residues, such as Phe, Trp and Tyr; and polar amino acid residues, such as Asn and Gln. In a highly preferred embodiment of the invention the amino acid residue to be introduced in one or more of the positions R137, R139 and/or R140 is a proline residue.

Amino acid residue to be introduced in position S132 or S142 may be selected from the group consisting of small amino acid residues, such as Ala, Gly, Ser, Cys and Thr; acidic amino acid residues, such as Asp and Glu: hydrophobic amino acid residues, such as Ile, Leu, Met, Pro and Val; aromatic amino acid residues, such as Phe, Trp and Tyr; and polar amino acid residues, such as Asn and Gln. In a highly preferred embodiment of the invention the amino acid residue to be introduced in position S132 or S142 is Pro. Accordingly, in a preferred embodiment of the invention, the variant comprises a substitution selected from the group consisting of S132P, S142P and S132P+S142P, in particular S132P or S142P.

As explained above, the C-terminal part of the IFNG variant should, in addition to a substitution in position S132 and/or S142, contain at least one further substitution in a position selected from the group consisiting of R137, R139, R140 and combinations thereof. Thus, in addition to a substitution in position S132 and/or S142, the C-terminal part of the variant shall contain a substitution in a position selected from the group consisting of R137, R139, R140, R137+R139, R137+R140, R139+R140 and R137+R139+R140.

Specific examples of substitutions in posititon R137 include R137A, R137V, R137L, R137I, R137M, R137F, R137W, R137P, R137G, R137S, R137T, R137C, R137Y, R137N, R137Q, R137D and R137E, preferably R137P.

Specific examples of substitutions in posititon R139 include R139A, R139V, R139L, R139I, R139M, R139F, R139W, R139P, R139G, R139S, R139T, R139C, R139Y, R139N, R139Q, R139D and R139E, preferably R139P.

Specific examples of substitutions in posititon R140 include R140A, R140V, R140L, R140I, R140M, R140F, R140W, R140P, R140G, R140S, R140T, R140C, R140Y, R140N, R140Q, R140D, R140E and R140K, preferably R140P.

Preferably, the C-terminal part of the variant contains a substitution in a position selected from the group consisting of R137P, R139P, R140P, R137P+R139P, R137P+R140P, R139P+R140P and R137P+R139P+R140P.

Specific examples of full-length IFNG variants comprising a substitution in position S132 include variants selected from the group consisting of S132P+R137P, S132P+R139P, S132P+R140P, S132P+R137P+R139P, S132P+R137P+R140P, S132P+R139P+R140and S132P+R137P+R139P+R140P, preferably selected from the group consisting of S132P+R137P+R140P and S132P+R140P, most preferably S132P+R137P+R140P.

Specific examples of full-length IFNG variants comprising a substitution in position S142 include variants selected from the group consisting of R137P+S142P, R139P+S142P, R140P+S142P, R137P+R139P+S142P, R137P+R140P+S142P, R139P+R140P+S142P and R137P+R139P+R140P+S142P, preferably selected from the group consisting of R137P+S142P and R137P+R139P+S142P.

As also indicated above, it has also now been found that a substitution in positions R137 and R140 impairs the proteolytic processing of the polypeptide and hence results in a more homogenous product.

Thus, in a second aspect the present invention relates to a full-length IFNG polypeptide variant exhibiting IFNG activity, wherein said variant comprises an amino acid substitution in position R137 and an amino acid substitution in position R140.

Furthermore, the present invention also relates to a substantially homogenous population of a full-length IFNG variant, wherein said full-length IFNG variant exhibits IFNG activity and wherein said full-length IFNG variant comprises an amino acid substitution in position 137 and an amino acid substitution in position R140.

Moreover, the present invention also relates to a composition comprising a substantially homogenous population of a full-length IFNG variant, wherein said full-length IFNG variant exhibits IFNG activity and wherein said full-length IFNG variant comprises an amino acid substitution in position R137 and an amino acid substitution in position R140.

When used herein, the term "substantially homogenous population" is defined as a population giving rise to a mass spectroscopic profile characterized by a single, dominant peak having an area under the curve (AUC) that is at least 3-fold higher than the AUC of any other peak appearing in the profile. Preferably, the AUC of the dominant peak is at least 4-fold higher, such as at least 5-fold higher than the AUC of any other peak appearing in the profile.

For example, the population of IFNG variants may contain at least 75% of the full-length IFNG variant of the invention (as compared to the total amount of IFNG variants in the population), preferably at least 80%, such as at least 85%, e.g. at least 90%, more preferably at least 95%, such as at least 96%, e.g. at least 97%, even more preferably at least 98%, such as at least 99%.

Amino acid residue to be introduced in the positions R137 and R140 may independently be selected from the group consisting of small amino acid residues, such as Ala, Gly, Ser, Cys and Thr; acidic amino acid residues, such as Asp and Glu; hydrophobic amino acid residues, such as Ile, Leu, Met, Pro and Val; aromatic amino acid residues, such as Phe, Trp and Tyr; and polar amino acid residues, such as Asn and Gln.

In a preferred embodiment of the invention at least one of the amino acid residues to be introduced in the positions R137 and R140 is Pro.

Thus, in a preferred embodiment of the invention, the variant comprises the substitutions R137X+R140P, wherein X is any amino acid residue, except arginine and lysine.

In another preferred embodiment of the invention, the variant comprises the substitutions R137P+R140X, wherein X is any amino acid residue except arginine.

In a highly preferred embodiment of the invention the amino acid residue to be introduced in both of positions R137 and R140 is Pro, i.e. in a highly preferred embodiment of the invention, the variant comprises the substitutions R137P+R140P.

Further Modifications in the C-Terminal Part

The above-mentioned modifications may be the only modifications in the C-terminal part of the variant. However, in another embodiment of the invention the variant comprises at least one further modification in the C-terminal part of the variant from amino acid residue S132 to amino acid Q143. For example, as will be acknowledged by the skilled person, introduction of a non-naturally occurring residue in a human polypeptide may give rise to an epitope capable of inducing a response from the human immune system.

This problem may be effectively solved by "shielding" the introduced residues, e.g. by introducing an in vivo N-glycosylation site or other non-polypeptide moieties, such as PEG, in the vicinity of the introduced residues. For example, an amino acid residue comprising an attachment group for a non-polypeptide moiety (which is capable of screening the potential epitope) may be introduced in the vicinity of the introduced residues. One particular preferred amino acid residue comprising an attachment group for a non-polypeptide moiety, such as PEG, is cysteine. Apart from shielding the introduced residues, the introduced cyeteine residue may, when covalently attached to a non-polypeptide moiety, such as PEG, confer additional advantageous properties to the IFNG polypeptide, such as increased functional in vivo half-life and/or increased $AUC_{sc}$.

Although introduction of N-glycosylation sites in the C-terminal part of the IFNG polypeptide is also contemplated according to the present invention, this approach is not particularly preferred since full utilization of N-glycosylation sites in the C-terminal part of IFNG may prove difficult.

Thus, in another embodiment of the invention the variant further comprises at least one cysteine residue in the C-terminal part of the variant from amino acid residue S132 to amino acid Q143. Specific examples of substitutions which introduce a cysteine residue in the C-terminal part of the IFNG variant include substitutions selected from the group consisting of S132C, Q133C, M134C, L135C, F136C, R137C, G138C, R139C, R140C, A141C, S142 and Q143. It will be understood that cysteine residues should not be introduced in positions which are essential for obtaining the full-length IFNG gamma variant.

Although two or more cysteine residues may be introduced in the C-terminal part of the IFNG variant it is preferred that only a single cysteine residue is introduced in this region of the molecule.

As will be understood, the introduced cysteine residue is preferably covalently attached (conjugated) to a non-polypeptide moiety, such as a polymer molecule, preferably PEG or more preferably mPEG having a molecular weight from 1-20 kDa, such as 1 kDa, 2 kDa, 5 kDa, 10 kDa, 12 kDa or 20 kDa. The conjugation between the cysteine-containing IFNG polypeptide and the polymer molecule may be achieved in any suitable manner, e.g. as described in the section entitled "Conjugation to a polymer molecule", e.g. in using a one step method or in the stepwise manner referred to in said section. The preferred method for PEGylating the IFNG polypeptide is to covalently attach PEG to cysteine residues using cysteine-reactive PEGs. A number of highly specific, cysteine-reactive PEGs with different groups (e.g. maleimide, vinylsulfone and orthopyridyl-disulfide) and different size PEGs (2-20 kDa) are commercially available, e.g. from Shearwater Polymers Inc., Huntsville, Ala., USA.

Modifications in the Amino Acid Sequence from Residue No. 1 to Residue No. 131

As far as the amino acid sequence from residue no. 1 to residue no. 131 is concerned, this part of the sequence may be identical to residue no. 1 to residue no. 131 of huIFNG and may be glycosylated (e.g. by producing the variant in a glycosylation host cell) or un-glycosylated (e.g. by producing the variant in a prokaryotic host cell, such as E. coli).

However, in a preferred embodiment of the invention, the variant comprises an amino acid sequence from residue no. 1 to residue no. 131, which further comprises 1-10, such as 1-7, e.g. 1-5 or 1-3 modifications, preferably substitutions, compared to amino acid residue no. 1 to residue no. 131 of huIFNG. One example includes the substitution S99T (leading to a more efficient utilization of the position 97 N-glycosylation site). Other interesting substitutions include E38N+ S40T (leading to an increased $AUC_{sc}$), in particular E38N+ S40+S99T.

Such variants may be glycosylated or un-glycosylated. Preferably, such variants are glycosylated.

Other interesting modifications are discussed in the below sections entitled "IFNG variants with optimised N-glycosylation sites", "IFNG variants with increased $AUC_{sc}$ and/or increased half-life", "IFNG variants wherein the non-polypeptide moiety is a sugar moiety", "IFNG variants wherein the non-polypeptide moiety is a molecule, which has cysteine as an attachment group" and "IFNG variants wherein the first non-polypeptide moiety is a sugar moiety and the second non-polypeptide moiety is a molecule, which has cysteine as an attachment group".

IFNG Variants with Optimised N-Glycosylation Sites

As mentioned above, the amino acid sequence from residue no. 1 to residue no. 131 preferably comprises 1-10, such as 1-7, e.g. 1-5 or 1-3, modifications, preferably substitutions, compared to amino acid residue no. 1 to residue no. 131 of huIFNG.

One class of interesting modifications that may be introduced into this part of the sequence include modifications, which serve to optimise the glycosylation of a given glycosylation site.

It has been found (see WO 02/081507) that glycosylation of the naturally occurring N-glycosylation site located in position 97 of huIFNG may be increased, i.e. an increased fraction of fully, or substantially fully, glycosylated IFNG polypeptides may be obtained, by substituting the serine residue located in position 99 of huIFNG with a threonine residue. For example, by performing the S99T substitution it has been found that about 90% of the polypeptides present in the harvested medium utilize both N-glycosylation sites, whereas only about 60% of the huIFNG polypeptides present in the harvested medium were fully glycosylated.

Accordingly, in a very interesting embodiment of the invention, the IFNG variant of the invention comprises the substitution S99T.

In addition to the already mentioned S99T mutation required for optimisation of the in vivo N-glycosylation site at position 97, other in vivo glycosylation sites, which may have been introduced into the sequence (see the section entitled "IFNG variants wherein the non-polypeptide moiety is a sugar moiety") may be optimised. Normally, the in vivo glycosylation site is an Nglycosylation site, but also an O-glycosylation site is contemplated as relevant for the present invention. This optimisation may be achieved by performing a modification, preferably a substitution, in a position, which is located close to a glycosylation site, in particular close to an in vivo N-glycosylation site. Specific examples of suitable positions where in vivo N-glycosylation sites may be introduced, are disclosed in WO 01/36001, WO 02/081507 and in the section entitled "IFNG variants wherein the non-polypeptide moiety is a sugar moiety".

An amino acid residue "located close to" a glycosylation site is usually located in position −4, −3, −2, −1, +1, +2, +3 or +4 relative to the amino acid residue of the glycosylation site to which the carbohydrate is attached, preferably in position −1, +1, or +3, in particular in position +1 or +3. Thus, the amino acid residue located close to an in vivo N-glycosylation site (having the sequence N-X-S/T/C) may be located in position −4, −3, −2, −1, +1, +2, +3 or +4 relative to the N-residue.

When position +2 relative to the N-residue is modified it will be understood that only a limited number of modifications are possible since in order to maintain/introduce an in vivo N-glycosylation site, the amino acid residue in said position must be either Ser, Thr or Cys. In a particular preferred embodiment of the invention, the modification of the amino acid residue in position +2 relative to the in vivo N-glycosylation site is a substitution where the amino acid residue in question is replaced with a Thr residue. If, on the other hand, said amino acid residue is already a Thr residue it is normally not preferred or necessary to perform any substitutions in that position. When X is modified, X should not be Pro and preferably not Trp, Asp, Glu and Leu. If X is modified, the amino acid residue to be introduced is preferably selected form the group consisting of Phe, Asn, Gln, Tyr, Val, Ala, Met, Ile, Lys, Gly, Arg, Thr, His, Cys and Ser, more preferably Ala, Met, Ile, Lys, Gly, Arg, Thr, His, Cys and Ser, in particular Ala or Ser. When position +3 relative to the N-residue is modified, the amino acid residue to be introduced is preferably selected from the group consisting of His, Asp, Ala, Met, Asn, Thr, Arg, Ser and Cys, more preferably Thr, Arg, Ser and Cys. Such modifications are particular relevant if the X residue is a Ser residue.

Thus, with respect to the naturally present in vivo N-glycosylation, it is contemplated that the N-glycosylation site at position 97 may be further optimised by performing a modification, such as a substitution, in a position selected from the group consisting of E93, K94, L95, T96, Y98, V100 and T101 (i.e. at position −4, −3, −2, −1, +1, +3 or +4 relative to N97). Specific examples of substitutions performed in position 98 include Y98F, Y98N, Y98Q, Y98V, Y98A, Y98M, Y98I, Y98K, Y98G, Y98R, Y98T, Y98H, Y98C and Y98S, preferably Y98A, Y98M, Y98I, Y98K, Y98G, Y98R, Y98T, Y98H, Y98C and Y98S, in particular Y98S. Specific examples of substitutions performed in position 100 include V100H, V100D, V100A, V100M, V100N, V100T, V100R, V100S, or V100C, in particular V100T, V100R, V100S or V100C.

In a similar way, with respect to the in vivo N-glycosylation site at position 25 it is contemplated that this site may be further optimised by performing a modification, such as a substitution, in a position selected from the group consisting of D21, V22, A23, D24, G26, L28 and F29 (i.e. at position −4, −3, −2, −1, +1, +3 or +4 relative to N25). Specific examples of substitutions performed in position 26 include G26F, G26N, G26Y, G26Q, G26V, G26A, G26M, G26I, G26K, G26R, G26T, G26H, G26C and G26S, preferably G26A, G26M, G26I, G26K, G26R, G26T, G26H, G26C and G26S, more preferably G26A and G26S, in particular G26A. Specific examples of substitutions performed in position 28 include G28H, G28D, G28A, G28M, G28N, G28T, G28R, G28S, or G28S, in particular G28A, G28T, G28R, G28S or G28C.

Obviously, any of the modifications mentioned in connection with optimisation of glycosylation at position 97 may be combined with any of the mentioned in connection with optimisation of glycosylation at position 25.

IFNG Variants with Increased $AUC_{sc}$ and/or Increased Half-Life

Another class of interesting modifications that may be introduced into the amino acid sequence from residue no. 1 to residue no. 131 include modifications, in particular substitutions, which serve to increase the $AUC_{sc}$ and/or the serum half-life/functional in vivo half-life when administered intravenously.

In a particular interesting embodiment of the invention the IFNG variant comprises, in the amino acid sequence from residue no. 1 to residue no. 131, at least one introduced and/or at least one removed amino acid residue comprising an attachment group for a non-polypeptide moiety. Preferably, the amino acid sequence from residue no. 1 to residue no. 131 comprises at least one introduced amino acid residue comprising an attachment group for a non-polypeptide moiety.

Such variants typically exhibit an increased functional in vivo half-life and/or an increased $AUC_{sc}$.

Thus, interesting IFNG variants are such variants where the ratio between the serum half-life (or functional in vivo half-life) of said variant and the serum half-life (or functional in vivo half-life) of glycosylated huIFNG or glycosylated [S99T]huIFNG is at least 1.25, more preferably at least 1.50, such as at least 1.75, e.g. at least 2, even more preferably at least 3, such as at least 4, e.g. at least 5, when administered intravenously, in particular when administered intraveniously in non-human primates, such as monkeys.

Other examples of interesting IFNG variants are such variants where the ratio between the serum half-life (or functional in vivo half-life) of said variant and the serum half-life (or functional in vivo half-life) of Actimmune® is at least 2 more preferably at least 3, such as at least 4, e.g. at least 5, even more preferably at least 6, such as at least 7, e.g. at least 8, most preferably at least 9, such as at least 10, when administered intravenously, in particular when administered intraveniously into rats or non-human primates, such as monkeys.

The term "increased" as used about the $AUC_{sc}$ is used to indicate that the Area Under the Curve for an IFNG variant of the invention, when administered subcutaneously, is statistically significantly increased relative to that of a reference molecule, such as glycosylated huIFNG, glycosylated [S99T]huIFNG or Actimmune®, determined under comparable conditions. Thus, preferred IFNG variants are such variants, which have an increased $AUC_{sc}$, as compared to any of the reference molecules mentioned above. Evidently, the same amount of IFNG activity should be administered for the IFNG variant of the invention and the reference molecule.

Particular preferred IFNG variants are such variants where the ratio between the $AUC_{sc}$ of said variant and the $AUC_{sc}$ of glycosylated huIFNG or glycosylated [S99T]huIFNG is at least 1.25, such as at least 1.5, e.g. at least 2, more preferably at least 3, such as at least 4, e.g. at least 5 or at least 6, even more preferably at least 7, such as at least 8, e.g. at least 9 or at least 10, most preferably at least 12, such as at least 14, e.g. at least 16, at least 18 or at least 20, in particular when administered (subcutaneously) in rats.

Other examples of particular preferred IFNG variants are such variants where the ratio between the $AUC_{sc}$ of said variant and the $AUC_{sc}$ of Actimmune® is at least 100, more preferably at least 150, such as at least 200, e.g. at least 250, even more preferably at least 300, such as at least 400 e.g. at least 500, most preferably at least 750, such as at least 1000, e.g. at least 1500 or at least 2000, in particular when administered (subcutaneously) in rats.

In order to avoid too much disruption of the structure and function of the IFNG polypeptide the total number of amino acid residues to be modified in accordance with this embodiment of the invention (i.e. in the region from residue no. 1 to residue no. 131) typically does not exceed 10. Usually the amino acid sequence from residue no. 1 to residue no. 131 comprises 1-10, such as 1-7, e.g. 1-5 or 1-3 modifications compared to residue no. 1 to residue no. 131 of huIFNG. Thus, normally the IFNG variant comprises an amino acid sequence (from residue no. 1 to residue no. 131) which differs from the amino acid sequence of huIFNG (from residue no. 1 to residue no. 131) in 1, 2, 3, 4, 5, 6, 7, 8, 9 or 10 amino acid residues. Preferably, the modification(s) is/are a substitution(s).

By removing or introducing an amino acid residue comprising an attachment group for the non-polypeptide moiety it is possible to specifically adapt the polypeptide so as to make the molecule more susceptible to conjugation to the non-polypeptide moiety of choice, to optimise the conjugation pattern (e.g. to ensure an optimal distribution of non-polypeptide moieties on the surface of the IFNG polypeptide) and thereby obtain a new conjugate molecule, which exhibits IFNG activity and in addition one or more improved properties as compared to the huIFNG based molecules available today. For instance, by introduction of attachment groups, the IFNG polypeptide is boosted or otherwise altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g. to an amino acid residue located at or near a functional site of the polypeptide (since conjugation at such a site may result in inactivation of the resulting conjugated polypeptide due to impaired receptor recognition). Further, it may be advantageous to remove an attachment group located closely to another attachment group in order to avoid heterogeneous conjugation to such groups. In an interesting embodiment more than one amino acid residue of the IFNG polypeptide is altered, e.g. the alteration embraces removal as well as introduction of amino acid residues comprising attachment sites for the non-polypeptide moiety of choice. This embodiment is considered of particular interest in that it is possible to specifically design the IFNG polypeptide so as to obtain an optimal conjugation to the non-polypeptide moiety.

In addition to the removal and/or introduction of amino acid residues, the polypeptide may comprise other modifications, e.g. substitutions, that are not related to introduction and/or removal of amino acid residues comprising an attachment group for the non-polypeptide moiety. Examples of such modifications include conservative amino acid substitutions and/or introduction of Cys-Tyr-Cys or Met at the N-terminus.

The exact number of attachment groups available for conjugation and present in the IFNG polypeptide in dimeric form is dependent on the effect desired to be achieved by the conjugation. The effect to be obtained is, e.g., dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.).

It will be understood that the amino acid residue comprising an attachment group for a non-polypeptide moiety, either it be removed or introduced, is selected on the basis of the nature of the non-polypeptide moiety part of choice and, in most instances, on the basis of the conjugation method to be used. For instance, when the non-polypeptide moiety is a polymer molecule such as a polyethylene glycol- or polyalkylene oxide-derived molecule, amino acid residues capable of functioning as an attachment group may be selected from the group consisting of cysteine, lysine, aspartic acid, glutamic acid and arginine. In particular, cysteine is preferred. When the non-polypeptide moiety is a sugar moiety the attachment group is, e.g., an in vivo glycosylation site, preferably an N-glycosylation site.

Whenever an attachment group for a non-polypeptide moiety is to be introduced into or removed from the IFNG polypeptide, the position of the polypeptide to be modified is conveniently selected as follows:

The position is preferably located at the surface of the IFNG polypeptide, and more preferably occupied by an amino acid residue that has more than 25% of its side chain exposed to the surface, in particular more than 50% of its side chain exposed to the surface, as determined on the basis of a 3D structure or model of IFNG in its dimeric form, the structure or model optionally further comprising one or two IFNG receptor molecules. Such positions are listed in Example 1 herein.

In addition, it may be of interest to modify one or more amino acid residues located in the loop regions of IFNG since most amino acid residues within these loop regions are exposed to the surface and located sufficiently far away from functional sites so that non-polypeptide moieties, such as polymer molecules, in particular PEG molecules, and/or N-glycosylation sites, may be introduced without impairing the function of the molecule. Such loops regions may be identified by inspection of the three-dimensional structure of huIFNG, optinally in complex with its receptor(s). The amino acid residues constituting said loop regions are residues N16-K37 (the "A-B loop"), F60-S65 (the "B-C loop"), N83-S84 (the "C-D loop") and Y98-L103 (the "D-E loop").

Furthermore, in the IFNG variants of the invention, attachment groups located at the receptor-binding site of IFNG may be removed, preferably by substitution of the amino acid residue comprising such group. The amino acid residues constituting the IFNG receptor-binding site are Q1, D2, Y4, V5, E9, K12, G18, H19, S20, D21, V22, A23, D24, N25, G26, T27, L30, K34, K37, K108, H111, E112, I114, Q115, A118 and E119 (see also Example 2 herein).

In the case of a single chain IFNG polypeptide it may be sufficient to remove attachment groups in the receptor-binding site of only one of the monomers and thereby obtain a single chain IFNG polypeptide conjugate with one active and one inactive receptor-binding site.

In order to determine an optimal distribution of attachment groups, the distance between amino acid residues located at the surface of the IFNG polypeptide is calculated on the basis of a 3D structure of the IFNG dimeric polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group are determined. In case of glycine, CA is used instead of CB. In the IFNG polypeptide part of the invention any of said distances is preferably more than 8 Å, in particular more than 10 Å in order to avoid or reduce heterogeneous conjugation.

Also, the amino acid sequence of the IFNG polypeptide variant may differ from the huIFNG amino acid sequence in that one or more amino acid residues constituting part of an epitope has been removed, preferably by substitution to an amino acid residue comprising an attachment group for the non-polypeptide moiety, so as to destroy or inactivate the epitope. Epitopes of huIFNG may be identified by use of methods known in the art, also known as epitope mapping, see, e.g. Romagnoli et al., Biol Chem, 1999, 380(5):553-9, DeLisser H M, Methods Mol Biol, 1999, 96:11-20, Van de Water et al., Clin Immunol Immunopathol, 1997, 85(3):229-35, Saint-Remy J M, Toxicology, 1997, 119(1):77-81, and Lane D P and Stephen C W, Curr Opin Immunol, 1993, 5(2):268-71. One method is to establish a phage display library expressing random oligopeptides of e.g. 9 amino acid residues. IgG1 antibodies from specific antisera towards huIFNG are purified by immunoprecipitation and the reactive phages are identified by immunoblotting. By sequencing the DNA of the purified reactive phages, the sequence of the oligopeptide can be determined followed by localization of the sequence on the 3D-structure of the IFNG. The thereby identified region on the structure constitutes an epitope that then can be selected as a target region for introduction of an attachment group for the non-polypeptide moiety.

Functional in vivo half-life and serum half-life is inter alia dependent on the molecular weight of the polypeptide and the number of attachment groups needed for providing increased half-life thus depends on the molecular weight of the non-polypeptide moiety in question. In one embodiment, the IFNG polypeptide of the invention has a molecular weight of at least 67 kDa, in particular at least 70 kDa as measured by SDS-PAGE according to Laemmli, U. K., Nature Vol. 227 (1970), p. 680-85. IFNG has a MW in the range of about 34-50 kDa, and therefore additional about 20-40 kDa is required to obtain the desired effect. This may, e.g., be provided by 2-4 10 kDa PEG molecules or by a combination of additional in vivo glycosylation sites and additional PEG molecules, or as otherwise described herein.

Preferably, a conjugated IFNG polypeptide according to the invention comprises 1-10 (additional) non-polypeptide moieties, such as 1-8, 2-8, 1-5 or 2-5 (additional) non-polypeptide moieties. Typically, the polypeptide will comprise 1-3 (additional) non-polypeptide moieties, such as 1, 2 or 3 (additional) non-polypeptide moieties.

As mentioned above, under physiological conditions IFNG exists as a dimeric polypeptide. The polypeptide is normally in homodimeric form (e.g. prepared by association of two IFNG polypeptide molecules prepared as described herein). However, if desired the IFNG polypeptide may be provided in single chain form, wherein two IFNG polypeptide monomers are linked via a peptide bond or a peptide linker. Providing the IFNG polypeptide in single chain form has the advantage that the two constituent IFNG polypeptides may be different which can be advantageous, e.g., to enable asymmetric mutagenesis of the polypeptides. For instance, PEGylation sites can be removed from the receptor-binding site from one of the monomers, but retained in the other. Thereby, after PEGylation one monomer has an intact receptor-binding site, whereas the other may be fully PEGylated (and thus provide significantly increased molecular weight).

IFNG Variants Wherein the Non-Polypeptide Moiety is a Sugar Moiety

In a particular preferred embodiment of the invention, the IFNG variant comprises, in the amino acid sequence from residue no. 1 to residue no. 131, at least one introduced and/or at least one removed glycosylation site, i.e. the non-polypeptide moiety is a sugar moiety. Preferably, the glycosylation site is an in vivo glycosylation site, e.g. an O-linked or N-linked sugar moiety, preferably an N-linked sugar moiety.

Thus, in one interesting embodiment of the invention said IFNG variant comprises, in the amino acid sequence from residue no. 1 to residue no. 131, at least one introduced glycosylation site, in particular an introduced in vivo N-glycosylation site. Preferably, the introduced glycosylation site is introduced by a substitution.

For instance, an in vivo N-glycosylation site may be introduced into a position (from residue no. 1 to residue no. 131) of the IFNG variant comprising an amino acid residue exposed to the surface. Preferably said surface-exposed amino acid residue has at least 25% of the side chain exposed to the surface, in particular at least 50% of its side chain exposed to the surface. Details regarding determination of such positions can be found in Example 1 herein.

The N-glycosylation site is introduced in such a way that the N-residue of said site is located in said position. Analogously, an O-glycosylation site is introduced so that the S or T residue making up such site is located in said position.

It should be understood that when the term "at least 25% (or 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached and these positions, where the serine or threonine residues are introduced, are allowed to be buried, i.e. to have less than 25% (or 50%) of their side chains exposed to the surface of the molecule.

Furthermore, in order to ensure efficient glycosylation it is preferred that the in vivo glycosylation site, in particular the N residue of the N-glycosylation site or the S or T residue of the O-glycosylation site, is located within the 118 N-terminal amino acid residues of the IFNG polypeptide, more preferably within the 97 N-terminal amino acid residues. Still more preferably, the in vivo glycosylation site is introduced into a position wherein only one mutation is required to create the site (i.e. where any other amino acid residues required for creating a functional glycosylation site is already present in the molecule).

For instance, substitutions that lead to introduction of an additional N-glycosylation site at positions exposed at the surface of the IFNG polypeptide and occupied by amino acid residues having at least 25% of the side chain exposed to the surface (in a structure with receptor molecule) include:

Q1N+P3S/T, P3N+V5S/T, K6N+A8S/T, E9N+L11S/T, K12S/T, K13N+F15S/T, Y14N+N16S/T, G18S/T, G18N, G18N+S20T, H19N+D21S/T, D21N+A23S/T, G26N+L28S/T, G31N+L33S/T, K34N+W36S/T, K37S/T, K37N+E39S/T, E38N, E38N+S40T, E39N+D41S/T, S40N+R42S/T, K55N+F57S/T, K58N+F60S/T, K61S/T, K61N+D63S/T, D62N+Q64S/T, D63N, D63N+S65T, Q64N+I66S/T, S65N+Q67S/T, Q67N, Q67N+S69T, K68N+V70S/T, E71N+I73S/T, T72N+K74S/T, K74N+D76S/T, E75N+M77S/T, K80S/T, V79N+F81S/T, K80N+F82S/T, N85S/T, S84N+K86S/T, K87S/T, K86N+K88S/T, K87N+R89S/T, D90N+F92S/T, E93N+L95S/T, K94N, K94N+T96S, T101N+L103S/T, D102N+N104S/T, L103N+V105S/T, Q106S/T, E119N, E119N+S121T, P122N+A124S/T, A123N+K125S/T, A124N, A124N+T126S, K125N+G127S/T, T126N+K128S/T, G127N+R129S/T, K128N+K130S/T, R129N+R131S/T and K130N. S/T indicates a substitution to a serine or threonine residue, preferably a threonine residue.

Substitutions that lead to introduction of an additional N-glycosylation site at positions exposed at the surface of the IFNG polypeptide having at least 50% of the side chain exposed to the surface (in a structure with receptor molecule) include:

P3N+V5S/T, K6N+A8S/T, K12S/T, K13N+F15S/T, G18S/T, D21N+A23S/T, G26N+L28S/T, G31N+L33S/T, K34N+W36S/T, K37N+E39S/T, E38N, E38N+S40S/T, E39N+D41S/T, K55N+F57S/T, K58N+F60S/T, K61S/T, D62N+Q64S/T, Q64N+I66S/T, S65N+Q67S/T, K68N+V70S/T, E71N+I73S/T, E75N+M77S/T, N85S/T, S84N+K86S/T, K86N+K88S/T, K87N+R89S/T, K94N, K94N+T96S, T101N+L103S/T, D102N+N104S/T, L103N+V105S/T,

Q106S/T, P122N+A124S/T, A123N+K125S/T, A124N, A124N+T126S, K125N+G127S/T, T126N+K128S/T, G127N+R129S/T, K128N+K130S/T, R129N+R131S/T, K130N and K130N+S132T. S/T indicates a substitution to a serine or threonine residue, preferably a threonine residue.

Substitutions where only one amino acid substitution is required to introduce an N-glycosylation site include K12S/T, G18S/T, G18N, K37S/T, E38N, M45N, I49N, K61S/T, D63N, Q67N, V70N, K80S/T, F82N, N85S/T, K87S/T, K94N, Q106S/T, E119N, A124N, K130N and R140N, in particular G18N, G18S/T, K37S/T, E38N, K61S/T, D63N, Q67N, K80S/T, N85S/T, K94N, Q106S/T, A124N and K130N (positions with more than 25% of its site chain exposed to the surface in a structure without receptor molecule), or more preferably G18N, E38N, D63N, Q67N, K94N, A124N and K130N (positions with more than 50% of its side chain exposed to the surface in a structure without receptor molecule).

Usually, it is not preferred to introduce N-glycosylation sites in the region constituting the receptor binding site (except in special cases, cf. the section entitled "Variants with a reduced receptor affinity"). Accordingly, the mutations Q1N+P3S/T, E9N+L11S/T, G18N, G18N+S20T, H19N+D21S/T, D21N+A23S/T, G26N+L28S/T, K34N+W36S/T, K37N+E39S/T, E119N and E119N+S121T should normally not be performed, unless a reduced receptor affinity is desired. In addition, the positive cluster K128, R129, K130 and R131 is required for activity and should normally not be modified.

Particular preferred IFNG variants of invention include at least one further substitution selected from the group consisting of G18S, G18T, E38N, E38N+S40T, K61S, K61T, S65N+Q67S, S65N+Q67T, N85S, N85T, K94N, Q106S and Q106T, more preferably selected from the group consisting of G18T, E38N+S40T, K61T, S65N+Q67T, N85T, K94N and Q106T, even more preferably selected from the group consisting of G18T, E38N+S40T, K61T, S65N+Q67T and N85T, in particular E38N+S40T.

Thus, specific examples of interesting full-length variants of the invention include variants selected from the group consisting of
[E38N+S40T+S99T+S132P+R137P]huIFNG,
[E38N+S40T+S99T+S132P+R139P]huIFNG,
[E38N+S40T+S99T+S132P+R140P]huIFNG,
[E38N+S40T+S99T+S132P+R137P+R139P]huIFNG,
[E38N+S40T+S99T+S132P+R137P+R140P]huIFNG,
[E38N+S40T+S99T+S132P+R139P+R140P]huIFNG,
[E38N+S40T+S99T+S132P+R137P+R139P+R140P] huIFNG,
[E38N+S40T+S99T+R137P+S142P]huIFNG,
[E38N+S40T+S99T+R139P+S142P]huIFNG,
[E38N+S40T+S99T+R140P+S142P]huIFNG,
[E38N+S40T+S99T+R137P+R139P+S142P]huIFNG,
[E38N+S40T+S99T+R137P+R140P+S142P]huIFNG,
[E38N+S40T+S99T+R139P+R140P+S142P]huIFNG and
[E38N+S40T+S99T+R137P+R139P+R140P+S142P] huIFNG, more preferably selected from the group consisting of
[E38N+S40T+S99T+S132P+R137P+R140P]huIFNG,
[E38N+S40T+S99T+S132P+R140P]huIFNG,
[E38N+S40T+S99T+R137P+R139P+S142P]huIFNG and
[E38N+S40T+S99T+R137P+S142P]huIFNG, most preferably selected from the group consisting of
[E38N+S40T+S99T+S132P+R137P+R140P]huIFNG and
[E38N+S40T+S99T+R137P+R139P+S142P]huIFNG.

Other specific examples of interesting full-length variants of the invention include variants selected from the group consisting of
[G18T+R137P+R140P]huIFNG,
[G18T+S99T+R137P+R140P]huIFNG,
[E38N+S40T+R137P+R140P]huIFNG,
[E38N+S40T+S99T+R137P+R140P]huIFNG,
[K61T+R137P+R140P]huIFNG,
[K61T+S99T+R137P+R140P]huIFNG,
[S65N+Q67T+R137P+R140P]huIFNG,
[S65N+Q67T+S99T+R137P+R140P]huIFNG,
[N85T+R137P+R140P]huIFNG and
[N85T+S99T+R137P+R140P]huIFNG, more preferably selected from the group consisting of
[G18T+S99T+R137P+R140P]huIFNG,
[E38N+S40T+S99T+R137P+R140P]huIFNG,
[K61T+S99T+R137P+R140P]huIFNG,
[S65N+Q67T+S99T+R137P+R140P]huIFNG, and
[N85T+S99T+R137P+R140P]huIFNG, most preferably [E38N+S40T+S99T+R137P+R140P] huIFNG.

The IFNG polypeptide variant of the invention preferably contains a single additional in vivo glycosylation site in the amino acid sequence from residue no. 1 to residue no. 131. However, in order to become of a sufficient size to increase the functional in vivo half-life or the serum half-life it may be desirable that the polypeptide variant comprises more than one additional in vivo N-glycosylation site, in particular 2-7 or 2-5 additional in vivo N-glycosylation sites, such as 2, 3, 4, 5, 6 or 7 in vivo N-glycosylation sites. Such in vivo N-glycosylation sites are preferably introduced by one or more substitutions described in any of the above lists.

Thus, in another interesting embodiment of the invention, the IFNG polypeptide comprises at least two introduced glycosylation sites, in particular at least two introduced N-glycosylation sites in the amino acid sequence from residue no. 1 to residue no. 131.

The at least two modifications, in particular substitutions, leading to the introduction of the at least two introduced N-glycosylation sites may preferably be selected from the group consisting of G18S, G18T, E38N, E38N+S40T, K61S, K61T, S65N+Q67S, S65N+Q67T, N85S, N85T, K94N, Q106S and Q106T, more preferably selected from the group consisting of G18T, E38N+S40T, K61T, S65N+Q67T, N85T, K94N and Q106T, even more preferably selected from the group consisting of G18T, E38N+S40T, K61T, S65N+Q67T and N85T.

Specific examples of such substitutions giving rise to an IFNG variant comprising at least two additional N-glycosylation sites in the amino acid sequence from residue no. 1 to residue no. 131 include: G18T+E38N+S40T, G18T+K61T, G18T+S65N+Q67T, G18T+N85T, E38N+S40T+K61T, E38N+S40T+S65N+Q67T, E38N+S40T+N85T, K61T+S65N+Q67T, K61T+N85T and S65N+Q67T+N85T.

Preferably, any of the above-mentioned modified IFNG variants further comprises the substitution S99T.

Furthermore, the naturally occurring N-glycosylation site located at position 25 may be removed. This may be done by removing the N25 residue and/or by removing the T27 residue, preferably by substitution. Preferably, the N-glycosylation site located at position 25 may be removed by the substitution N25G+T27P.

It will be understood that any of the above-mentioned modifications may be combined with any of the modifications disclosed in the section entitled "IFNG variants with optimised in vivo glycosylation sites", in particular with the substitution S99T and/or with any of the modifications disclosed in the section entitled "IFNG variants wherein the non-polypeptide moiety is a molecule, which has cysteine as an attachment group".

IFNG Variants Wherein the Non-Polypeptide Moiety is a Molecule, Which has Cysteine as an Attachment Group In another particular preferred embodiment of the invention the IFNG variant comprises, in the amino acid sequence from residue no. 1 to residue no. 131, at least one introduced cysteine residue. Preferably, the cysteine residue is introduced by substitution.

For instance, a cysteine residue may be introduced into a position of the IFNG polypeptide (from residue no. 1 to residue no. 131), which comprises an amino acid residue exposed to the surface. Preferably said surface-exposed amino acid residue has at least 25% of the side chain exposed to the surface, in particular at least 50% of its side chain exposed to the surface. Details regarding determination of such positions can be found in Example 1 herein.

For instance, substitutions that lead to introduction of a cysteine residue at positions exposed at the surface of the IFNG polypeptide and occupied by amino acid residue having at least 25% of the side chain exposed to the surface (in a structure with receptor molecule) include: Q1C, D2C, P3C, K6C, E9C, N10C, K13C, Y14C, N16C, G18C, H19C, D21C, N25C, G26C, G31C, K34C, N35C, K37C, E38C, E39C, S40C, K55C, K58C, N59C, K61C, D62C, D63C, Q64C, S65C, Q67C, K68C, E71C, T72C, K74C, E75C, N78C, V79C, K80C, N83C, S84C, N85C, K86C, K87C, D90C, E93C, K94C, T101C, D102C, L103C, N104C and E119C.

Substitutions that lead to introduction of a cysteine residue at positions exposed at the surface of the IFNG polypeptide and occupied by amino acid residue having at least 50% of the side chain exposed to the surface (in a structure with receptor molecule) include: P3C, K6C, N10C, K13C, N16C, D21C, N25C, G26C, G31C, K34C, K37C, E38C, E39C, K55C, K58C, N59C, D62C, Q64C, S65C, K68C, E71C, E75C, N83C, S84C, K86C, K87C, K94C, T101C, D102C, L103C and N104C.

Usually, it is not preferred to introduce cysteine residue (and subsequently attaching these cysteine residue to a non-polypeptide moiety) in the region constituting the receptor binding site (except in special cases, cf. the section entitled "Variants with a reduced receptor affinity"). Accordingly, the mutations Q1C, E9C, G18C, H19C, D21C, G26C, K34C, K37C and E119C should normally not be performed, unless a reduced receptor affinity is desired. In addition, the positive cluster K128, R129, K130 and R131 is required for activity and should normally not be modified.

Most preferably, said cysteine residue is introduced by a substitution selected from the group consisting of N10C, N16C, E38C, N59C, S65C, N83C, K94C, N104C and A124C, such as N16C, N59C and N16C+N59C. In a highly preferred embodiment of the invention said cysteine residue is introduced by the substitution N16C or N59C.

Thus, specific examples of interesting full-length variants of the invention include variants selected from the group consisting of
[N16C+S99T+S132P+R137P]huIFNG,
[N16C+S99T+S132P+R139P]huIFNG,
[N16C+S99T+S132P+R140P]huIFNG,
[N16C+S99T+S132P+R137P+R139P]huIFNG,
[N16C+S99T+S132P+R137P+R140P]huIFNG,
[N16C+S99T+S132P+R139P+R140P]huIFNG,
[N16C+S99T+S132P+R137P+R139P+R140P]huIFNG,
[N59C+S99T+S132P+R137P]huIFNG,
[N59C+S99T+S132P+R139P]huIFNG,
[N59C+S99T+S132P+R140P]huIFNG,
[N59C+S99T+S132P+R137P+R139P]huIFNG,
[N59C+S99T+S132P+R137P+R140P]huIFNG,
[N59C+S99T+S132P+R139P+R140P]huIFNG,
[N59C+S99T+S132P+R137P+R139P+R140P]huIFNG,
[N16C+S99T+R137P+S142P]huIFNG,
[N16C+S99T+R139P+S142P]huIFNG,
[N16C+S99T+R140P+S142P]huIFNG,
[N16C+S99T+R137P+R139P+S142P]huIFNG,
[N16C+S99T+R137P+R140P+S142P]huIFNG,
[N16C+S99T+R139P+R140P+S142P]huIFNG,
[N16C+S99T+R137P+R139P+R140P+S142P]huIFNG,
[N59C+S99T+R137P+S142P]huIFNG,
[N59C+S99T+R139P+S142P]huIFNG,
[N59C+S99T+R140P+S142P]huIFNG,
[N59C+S99T+R137P+R139P+S142P]huIFNG,
[N59C+S99T+R137P+R140P+S142P]huIFNG,
[N59C+S99T+R139P+R140P+S142P]huIFNG and
[N59C+S99T+R137P+R139P+R140P+S142P]huIFNG, more preferably selected from the group consisting of
[N16C+S99T+S132P+R137P+R140P]huIFNG,
[N16C+S99T+S132P+R140P]huIFNG,
[N59C+S99T+S132P+R137P+R140P]huIFNG,
[N59C+S99T+S132P+R140P]huIFNG,
[N16C+S99T+R137P+R139P+S142P]huIFNG,
[N16C+S99T+R137P+S142P]huIFNG,
[N59C+S99T+R137P+R139P+S142P]huIFNG and
[N59C+S99T+R137P+S142P]huIFNG, most preferably selected from the group consisting of
[N16C+S99T+S132P+R137P+R140P]huIFNG,
[N59C+S99T+S132P+R137P+R140P]huIFNG,
[N16C+S99T+R137P+R139P+S142P]huIFNG and
[N59C+S99T+R137P+R139P+S142P]huIFNG.

Other specific examples of interesting full-length variants of the invention include variants selected from the group consisting of
[N10C+R137P+R140P]huIFNG,
[N10C+R137P+R140P]Met-huIFNG,
[N10C+S99T+R137P+R140P]huIFNG,
[N16C+R137P+R140P]huIFNG,
[N16C+R137P+R140P]Met-huIFNG,
[N16C+S99T+R137P+R140P]huIFNG,
[E38C+R137P+R140P]huIFNG,
[E38C+R137P+R140P]Met-huIFNG,
[E38C+S99T+R137P+R140P]huIFNG,
[N59C+R137P+R140P]huIFNG,
[N59C+R137P+R140P]Met-huIFNG,
[N59C+S99T+R137P+R140P]huIFNG,
[S65C+R137P+R140P]huIFNG,
[S65C+R137P+R140P]Met-huIFNG,
[S65C+S99T+R137P+R140P]huIFNG,
[N83C+R137P+R140P]huIFNG,
[N83C+R137P+R140P]Met-huIFNG,
[N83C+S99T+R137P+R140P]huIFNG,
[K94C+R137P+R140P]huIFNG,
[K94C+R137P+R140P]Met-huIFNG,
[K94C+S99T+R137P+R140P]huIFNG,
[N104C+R137P+R140P]huIFNG,
[N104C+R137P+R140P]Met-huIFNG,
[N104C+S99T+R137P+R140P]huIFNG,
[A124C+R137P+R140P]huIFNG,
[A124C+R137P+R140P]Met-huIFNG and
[A124C+S99T+R137P+R140P]huIFNG, more preferably selected from the group consisting of
[N16C+R137P+R140P]huIFNG,
[N16C+R137P+R140P]Met-huIFNG,
[N16C+S99T+R137P+R140P]huIFNG,
[N59C+R137P+R140P]huIFNG,
[N59C+R137P+R140P]Met-huIFNG and
[N59C+S99T+R137P+R140P]huIFNG, even more preferably selected from the group consisting of
[N16C+R137P+R140P]huIFNG,
[N16C+S99T+R137P+R140P]huIFNG,
[N59C+R137P+R140P]huIFNG and
[N59C+S99T+R137P+R140P]huIFNG, most preferably selected from the group consisting of
[N16C+S99T+R137P+R140P]huIFNG and
[N59C+S99T+R137P+R140P]huIFNG.

The IFNG variant of the invention preferably contains a single cysteine residue in the amino acid sequence from residue no. 1 to residue no. 131. However, in order to become of a sufficient size to increase the functional in vivo half-life or the serum half-life it may be desirable that the polypeptide comprises more than one cysteine, in particular 2-7 or 2-5 cysteine residues, such as 2, 3, 4, 5, 6 or 7 cysteine residues. Such cysteine residues are preferably introduced by one or more substitutions described in any of the above lists.

Thus, in another embodiment of the invention, the IFNG variant comprises at least two introduced cysteine residues in the amino acid sequence from residue no. 1 to residue no. 131.

The at least two modifications, in particular substitutions, leading to the introduction of the at least two cysteine residues may preferably be selected from the group consisting of N10C, N16C, E38C, N59C, S65C, N83C, K94C, N104C and A124C. Specific examples of such substitutions giving rise to an IFNG polypeptide comprising at least two cysteine residues (in the amino acid sequence from residue no.1 to residue no. 131) include: N10C+N16C, N10C+E38C, N10C+N59C, N10C+S65C, N10C+N83C, N10C+K94C, N10C+N104C, N10C+A124C, N16C+E38C, N16C+N59C, N16C+S65C, N16C+N83C, N16C+K94C, N16C+N104C, N16C+A124C, E38C+N59C, E38C+S65C, E38C+N83C, E38C+K94C, E38C+N104C, E38C+A124C, N59C+S65C, N59C+N83C, N59C+K94C, N59C+N104C, N59C+A124C, S65C+N83C, S65C+K94C, S65C+N104C, S65C+A124C, N83C+K94C, N83C+N104C, N83C+A124C, K94C+N104C, K94C+A124C and N104C+A124C, in particular N16C+N59C.

Preferably, any of the above-mentioned modified IFNG polypeptides further comprises the substitution S99T.

Furthermore, the naturally occurring N-glycosylation site located at position 25 may be removed. This may be done by removing the N25 residue and/or by removing the T27 residue, preferably by substitution. Preferably, the N-glycosylation site located at position 25 may be removed by the substitution N25G+T27P.

As will be understood the introduced cysteine residue(s) may preferably be conjugated to a non-polypeptide moiety, such as PEG or more preferably mPEG. The conjugation between the cysteine-containing polypeptide and the polymer molecule may be achieved in any suitable manner, e.g. as described in the section entitled "Conjugation to a polymer molecule", e.g. in using a one step method or in the stepwise manner referred to in said section. The preferred method for PEGylating the IFNG polypeptide is to covalently attach PEG to cysteine residues using cysteine-reactive PEGs. A number of highly specific, cysteine-reactive PEGs with different groups (e.g. maleimide, vinylsulfone and orthopyridyl-disulfide) and different size PEGs (2-20 kDa, such as 5 kDa, 10 kDa, 12 kDa or 15 kDa) are commercially available, e.g. from Shearwater Polymers Inc., Huntsville, Ala., USA).

It will be understood that any of the above-mentioned modifications may be combined with any of the modifications disclosed in the section entitled "IFNG variants with optimised in vivo glycosylation sites", in particular with the substitution S99T and/or with any of the modifications disclosed in the section entitled "IFNG variants wherein the non-polypeptide moiety is a sugar moiety".

IFNG Variants Wherein a First Non-Polypeptide Moiety is a Sugar Moiety and a Second Non-Polypeptide Moiety is a Molecule, Which has Cysteine as an Attachment Group In a further embodiment of the invention the IFNG variant comprises, in the amino acid sequence from residue no. 1 to residue no. 131, at least one introduced N-glycosylation site and at least one introduced cysteine residue. Preferably, the cysteine residue and the N-glycosylation site is introduced by substitution. Such polypeptides may be prepared by selecting the residues described in the two preceding sections describing suitable positions for introducing N-glycosylation sites and cysteine residues, respectively. However, in a preferred embodiment of the invention said IFNG variants comprises substitutions selected from the group consisting of G18T+N10C, G18T+E38C, G18T+N59C, G18T+S65C, G18T+N83C, G18T+K94C, G18T+N104C, G18T+A124C, E38N+S40T+N10C, E38N+S40T+K94C, E38N+S40T+N59C, E38N+S40T+S65C, E38N+S40T+N83C, E38N+S40T+K94C, E38N+S40T+N104C, E38N+S40T+A124C, K61T+N10C, K61T+N16C, K61T+E38C, K61T+S65C, K61T+N83C, K61T+K94C, K61T+N104C, K61T+A124C, N85T+N10C, S65N+Q67T+N10C, S65N+Q67T+N16C, S65N+Q67T+E38C, S65N+Q67T+N59C, S65N+Q67T+N83C, S65N+Q67T+K94C, S65N+Q67T+N104C, S65N+Q67T+A124C, N85T+N10C, N85T+N16C, N85T+E38C, N85T+N59C, N85T+S65C, N85T+K94C, N85T+N104C, N95T+A124C, K94N+N10C, K94N+N16C, K94N+E38C, K94N+N59C, K94N+S65C, K94N+N83C, K94N+N104C, K94N+A124C, Q106T+N10C, Q106T+N16C, Q106T+E38C, Q106T+N59C, Q106T+S65T, Q106T+N83C, Q106T+K94C and Q106T+A124C, more preferably selected from the group consisting of E38N+S40T+N10C, E38N+S40T+N16C, E38N+S40T+N59C, E38N+S40T+S65C, E38N+S40T+N83C, E38N+S40T+K94C, E38N+S40T+N104C and E38N+S40T+A124C, most preferably selected from the group consisting of E38N+S40T+N16C and E38N+S40T+N59C.

Preferably, any of the above-mentioned modified IFNG polypeptides further comprises the substitution S99T.

In a still further interesting embodiment of the invention the IFNG variant comprises, in the amino acid sequence from residue no. 1 to residue no. 131, at least one removed N-glycosylation site and at least one introduced cysteine residue. Preferably, the cysteine residue is introduced by substitution and the N-glycosylation site is removed by substitution.

In particular, the removed N-glycosylation site is the N-glycosylation site located at position 25. This may be done by removing the N25 residue and/or by removing the T27 residue, preferably by the substitution N25G+T27P.

It will be understood that any of the above-mentioned modifications may be combined with any of the modifications disclosed in the section entitled "IFNG variants with optimised in vivo glycosylation sites", in particular with the substitution S99T.

IFNG Variants with a Reduced Receptor Affinity

One way to increase the serum half-life or the functional in vivo half-life of an IFNG polypeptide would be to decrease the receptor-mediated internalisation and thereby decrease the receptor-mediated clearance. The receptor-mediated internalisation is dependent upon the affinity of the IFNG dimer for the IFNG receptor complex and, accordingly, an IFNG polypeptide with a decreased affinity to the IFNG receptor complex is expected to be internalised, and hence cleared, to a lesser extent.

The affinity of the IFNG dimer to its receptor complex may be decreased by performing one or more modifications, in particular substitutions, in the recpetor binding region of the IFNG polypeptide. The amino acid residues which constitute the receptor binding region is defined in Example 2 herein. One class of substitutions that may be performed is conservative amino acid substitutions. In another embodiment, the modification performed gives rise to the introduction of an N-glycosylation site.

Thus, in a further interesting embodiment of the invention the IFNG polypeptide comprises, in the amino acid sequence from residue no. 1 to residue no. 131, at least one modification in the receptor binding site (as defined herein). More particularly, the IFNG polypeptide comprises at least one substitution, preferably a substitution, which creates an in vivo N-glycosylation site, in said receptor binding region. For instance, such substitutions may be selected from the group consisting of Q1N+P3S/T, D2N+Y4S/T, Y4N+K6S/T, V5N+E7S/T, E9N+L11S/T, K12N+Y14S/T, G18N, G18N+S20T, H19N+D21S/T, S20N+V22S/T, D21N+A23S/T, V22N+D24S/T, D24N+G26S/T, G26N+L28S/T, L30N+I32S/T, K34N+W36S/T, K37N+E39S/T, K108N+I110S/T, H111N+L113S/T, E112N+I114S/T, I114N+V116S/T, Q115N+M117S/T, A118N+L120S/T, E119N and E119N+S121T, preferably from the group consisting of Q1N+P3S/T, D2N+Y4S/T, E9N+L11S/T, K12N+Y14S/T, G18N, G18N+S20T, H19N+D21S/T, S20N+V22S/T, D21N+A23S/T, K34N+W36S/T, K37N+E39S/T, H111N+L113S/T, Q115N+M117S/T, A118N+L120S/T, E119N and E119N+S121T (introduction of N-glycosylation sites in positions comprising an amino acid residue having at least 25% of its side chain exposed to the surface), more preferably from the group consisting of Q1N+P3S/T, D2N+Y4S/T, E9N+L11S/T, G18N, G18N+S20T, H19N+D21S/T, S20N+V22S/T, D21N+A23S/T, K34N+W36S/T, K37N+E39S/T, Q115N+M117S/T, A118N+L120S/T, E119N and E119N+S121T (introduction of N-glycosylation sites in positions comprising an amino acid residue having at least 50% of its side chain exposed to the surface), even more preferably from the group consisting of Q1N+P3T, D2N+Y4T, E9N+L11T, G18N+S20T, H19N+D21T, S20N+V22T, D21N+A23T, K34N+W36T, K37N+E39T, Q115N+M117T, A118N+L120T and E119N+S121T, most preferably from the group consisting of G18N+S20T, H19N+D21T, D21N+A23T and E119N+S121T, in particular D21N+A23T.

Such variants are contemplated to exhibit a reduced receptor affinity as compared to glycosylated huIFNG, glycosylated [S99T]huIFNG or Actimmune®. The receptor affinity may be measured by any suitable assay and will be known to the person skilled in the art. One example of a suitable assay for determining the receptor binding affinity is the BIAcore® assay described in Michiels et al. Int. J. Biochem. Cell Biol. 30:505-516 (1998). Using the above-identified assay, IFNG polypeptides considered useful for the purposes described herein are such IFNG polypeptides, wherein the binding affinity ($K_d$) is 1-95% of the $K_d$-value of glycosylated huIFNG, glycosylated [S99T]huIFNG or Actimmune®. For example the $K_d$-value of the IFNG polypeptide may be 1-75% or 1-50%, such as 1-25%, e.g. 1-20% or even as low as 1-15%, 1-10% or 1-5% of the $K_d$-value of glycosylated huIFNG, glycosylated [S99T]huIFNG or Actmmune®.

Typically, such IFNG polypeptides having reduced receptor affinity will exhibit a reduced IFNG activity, e.g. when tested in the "Primary Assay" described herein. For example, the IFNG polypeptide may exhibit 1-95% (e.g. 5-95%) of the IFNG activity of glycosylated huIFNG, glycosylated [S99T] huIFNG or Actimmune®, e.g. 1-75% (e.g. 5-75%), such as 1-50% (e.g. 5-50%), e.g. 1-20% (e.g. 5-20%) or 1-10% (e.g. 5-10%) of the IFNG ativity of glycosylated huIFNG, glycosylated [S99T]huIFNG or Actimmune®.

As mentioned above, such IFNG polypeptides are contemplated to possess an increased half-life due to the reduced receptor-mediated clearance. Therefore, the IFNG polypeptides according to this aspect of the invention are contemplated to fulfil the requirements with respect to increased half-life described previously herein in connection with the definition of increased half-life.

Furthermore, it is contemplated that at least some of the cysteine variant, wherein said cysteine is covalently attached to a non-polypeptide moiety, such as PEG, also exhibit a reduced receptor-binding affinity and hence a lowered IFNG activity when tested in the "Primary Assay" described herein. It is envisaged that this property may be achieved independently of whether the cysteine (and hence the non-polypeptide moiety) is introduced in the receptor binding site since the non-polypeptide moiety is normally of such size that it may interact/partially impair binding to the IFNG polypeptide to its receptor independently of whether said moiety is introduced in the receptor binding site or not.

Evidently, any of the above-mentioned modifications giving rise to a reduced receptor binding affinity may be combined with any of the other modifications disclosed herein, in particular the modifications mentioned in the sections entitled "IFNG variants with optimised N-glycosylation sites", "IFNG variants wherein the non-polypeptide moiety is a sugar moiety", "IFNG variants wherein the non-polypeptide moiety is a molecule, which has cysteine as an attachment group" and "IFNG variants wherein the first non-polypeptide moiety is a sugar moiety and the second non-polypeptide moiety is a molecule, which has cysteine as an attachment group", such as the modifications selected from the group consisiting of E38N+S40T, S99T and combinations thereof.

Analysis of Truncation of IFNG Variants

Determination of C-terminal truncation of purified samples of IFNG polypeptides can be carried out in a number of ways.

One way of elucidating C-terminal truncations of IFNG polypeptides relies on accurate mass determinations by mass spectrometry. Unfortunately, the glycosylation of IFNG is heterogeneous thus making it extremely difficult to determine an accurate mass directly on the glycoprotein. Therefore, different levels of enzymatic deglycosylation are typically used in combination with mass spectrometry.

In one method, the entire glycan part of the IFNG polypeptide is cleaved of using the endo-glycosidase PNGase F followed by accurate mass determination using either ESI mass spectrometry or MALDI-TOF mass spectrometry. Comparing the experimental masses to the known amino acid sequence of IFNG makes it possible to determine the sites of C-terminal truncation.

In another related method, only the sialic acid of the glycan part of the IFNG polypeptide is cleaved off instead of the entire glycan. In some cases this is sufficient to reduce the heterogeneity of the sample to a level where the sites of C-terminal truncations can be deduced following accurate mass determination using either ESI mass spectrometry or MALDI-TOF mass spectrometry.

A more traditional way of elucidating C-terminal truncations of IFNG polypeptides employs peptide mapping in combination with mass spectrometry and chemical amino acid sequencing. In brief, the IFNG polypeptide is degraded with a protease of known specificity (e.g. Asp-N protease) followed by peptide separation using RP-HPLC. Fractions can then by mass analysed either on-line using ESI mass spectrometry or off-line using MALDI-TOF mass spectrometry. Comparing the masses obtained for peptides with the known amino acid sequence of IFNG makes it possible to determine the likely sites of C-terminal truncation. Verification can then be obtained through amino acid sequencing.

Conjugation Methods

The Non-Polypeptide Moiety

As indicated further above the non-polypeptide moiety is preferably selected from the group consisting of a sugar moiety (e.g. by way of in vivo N-glycosylation), a polymer molecule, a lipophilic compound and an organic derivatizing agent. All of these agents may confer desirable properties to the IFNG polypeptide, in particular increased $AUC_{sc}$, increased serum half-life, increased functional in vivo half-life when administered intravenously, reduced immunogenicity and/or increased bioavailability. The polypeptide is normally conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivating agent and a sugar moiety, to a lipophilic group and a polymer molecule, etc. When conjugated to two different types of non-polypeptide moieties these are preferably a sugar moiety and a polymer moiety. The conjugation to two or more different non-polypeptide moieties may be done simultaneous or sequentially. In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described.

Conjugation to a Lipophilic Compound

The polypeptide and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamine, a carotenoide or steroide, or a synthetic compound such as a carbon acid, an alcohol, an amine and sulphonic acid with one or more alkyl-, aryl-, alkenyl- or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide may be any suitable polymer molecule, such as a natural or synthetic homo-polymer or heteropolymer, typically with a molecular weight in the range of 300-100,000 Da or 1000-50,000 Da, such as in the range of 2000-40,000 Da or 2000-30,000 Da, e.g. in the range of 2000-20,000 Da, 2000-10,000 Da or 1000-5000 Da. More specifically, the polymer molecule, such as PEG, in particular mPEG, will typically have a molecular weight of about 2, 5, 10, 12, 15, 20, 30, 40 or 50 kDa.

Examples of homo-polymers include a polyol (i.e. poly-OH), a polyamine (i.e. poly-$NH_2$) and a polycarboxylic acid (i.e. poly-COOH). A hetero-polymer is a polymer, which comprises one or more different coupling groups, such as, e.g., a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), poly-carboxylate, poly-(vinylpyrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life and/or increasing the $AUC_{sc}$. Another example of a polymer molecule is human albumin or another abundant plasma protein. Generally, polyalkylene glycol-derived polymers are biocompatible, non-toxic, non-antigenic, non-immunogenic, have various water solubility properties, and are easily secreted from living organisms.

PEG is the preferred polymer molecule to be used, since it has only few reactive groups capable of cross-linking compared, e.g., to polysaccharides such as dextran, and the like. In particular, monofunctional PEG, e.g., monomethoxypolyethylene glycol (mPEG), is of interest since its coupling chemistry is relatively simple (only one reactive group is available for conjugating with attachment groups on the polypeptide). Consequently, the risk of cross-linking is eliminated, the resulting conjugated polypeptides are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidy carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g. from Shearwater Polymers, Inc., Huntsville, Ala., USA. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogue (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, AID-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which references are incorporated herein by reference. Furthermore, the following publications, incorporated herein by reference, disclose useful polymer molecules and/or PEGylation chemistries: U.S. Pat. Nos. 5,824,778, 5,476,653, WO 97/32607, EP 229,108, EP 402,378, U.S. Pat. Nos. 4,902,502, 5,281,698, 5,122,614, 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516, 673, EP 605 963, U.S. Pat. No. 5,382,657, EP 510 356, EP 400 472, EP 183 503 and EP 154 316.

The conjugation of the polypeptide variant and the activated polymer molecules is conducted by use of any conventional method, e.g. as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.).

The skilled person will be aware that the activation method and/or conjugation chemistry to be used depends on the attachment group(s) of the variant polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEGylation may be directed towards conjugation to all available attachment groups on the variant polypeptide (i.e. such attachment groups that are exposed at the surface of the polypeptide) or may be directed towards one or more specific attachment groups, e.g. the N-terminal amino group as described in U.S. Pat. No. 5,985,265 or to cysteine residues. Furthermore, the conjugation may be achieved in one step or in a stepwise manner (e.g. as described in WO 99/55377).

In a particular interesting embodiment PEGylation is achieved by conjugatin the PEG group(s) to introduced cysteine residues. Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 5 kDa, about 10 kD, about 12 kDa or about 20 kDa.

For PEGylation to cysteine residues the IFNG variant is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood, that the PEGylation is designed so as to produce the optimal molecule with respect to the number of PEG molecules attached, the size and form (e.g. whether they are linear or branched) of such molecules, and where in the polypeptide such molecules are attached. For instance, the molecular weight of the polymer to be used may be chosen on the basis of the desired effect to be achieved. For instance, if the primary purpose of the conjugation is to achieve a conjugate having a high molecular weight (e.g. to reduce renal clearance) it may be desirable to conjugate as few high Mw polymer molecules as possible to obtain the desired molecular weight. When a high degree of epitope shielding is desirable this may be obtained by use of a sufficiently high number of low molecular weight polymer (e.g. with a molecular weight of about 5,000 Da) to effectively shield all or most epitopes of the polypeptide. For instance, 2-8, such as 3-6 such polymers may be used.

In connection with conjugation to only a single attachment group on the protein (as described in U.S. Pat. No. 5,985, 265), it may be advantageous that the polymer molecule, which may be linear or branched, has a high molecular weight, e.g. about 20 kDa.

Normally, the polymer conjugation is performed under conditions aiming at reacting all available polymer attachment groups with polymer molecules. Typically, the molar ratio of activated polymer molecules to polypeptide is 1000-1, in particular 200-1, preferably 100-1, such as 10-1 or 5-1 in order to obtain optimal reaction. However, also equimolar ratios may be used.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378.

Subsequent to the conjugation residual activated polymer molecules are blocked according to methods known in the art, e.g. by addition of primary amine to the reaction mixture, and the resulting inactivated polymer molecules removed by a suitable method.

Coupling to a Sugar Moiety

The coupling of a sugar moiety may take place in vivo or in vitro. In order to achieve in vivo glycosylation of a polypeptide with IFNG activity, which have been modified so as to introduce one or more in vivo glycosylation sites (see the section "IFNG variants wherein the non-polypeptide moiety is a sugar moiety), the nucleotide sequence encoding the polypeptide variant must be inserted in a glycosylating, eukaryotic expression host. The expression host cell may be selected from fungal (filamentous fungal or yeast), insect or animal cells or from transgenic plant cells. Furthermore, the glycosylation may be achieved in the human body when using a nucleotide sequence encoding the polypeptide of the invention in gene therapy. In one embodiment the host cell is a mammalian cell, such as a CHO cell, a BHK cell or a HEK cell, e.g. a HEK293 cell, or an insect cell, such as an SF9 cell, or a yeast cell, e.g. *Saccharomyces cerevisiae, Pichia pastoris* or any other suitable glycosylating host, e.g. as described further below. Optionally, sugar moieties attached to the IFNG polypeptide by in vivo glycosylation are further modified by use of glycosyltransferases, e.g. using the glycoAdvance™ technology marketed by Neose, Horsham, Pa., USA. Thereby, it is possible to, e.g., increase the sialyation of the glycosylated IFNG polypeptide following expression and in vivo glycosylation by CHO cells.

Covalent in vitro coupling of glycosides to amino acid residues of IFNG may be used to modify or increase the number or profile of carbohydrate substituents. Depending on the coupling mode used, the sugar(s) may be attached to a) arginine and histidine, b) free carboxyl groups, c) free sulfhydryl groups such as those of cysteine, d) free hydroxyl groups such as those of serine, threonine, tyrosine or hydroxyproline, e) aromatic residues such as those of phenylalanine or tryptophan or f) the amide group of glutamine. These amino acid residues constitute examples of attachment groups for a sugar moiety, which may be introduced and/or removed in the IFNG polypeptide. Suitable methods of in vitro coupling are described, for example, in WO 87105330 and in Aplin et al., CRC Crit Rev. Biochem., pp. 259-306, 1981. The in vitro coupling of sugar moieties or PEG to protein- and peptide-bound Gln-residues can also be carried out by transglutaminases (TGases), e.g. as described by Sato et al., 1996 Biochemistry 35, 13072-13080 or in EP 725145.

Coupling to an Organic Derivatizing Agent

Covalent modification of the IFNG polypeptide may be performed by reacting (an) attachment group(s) of the polypeptide with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonateat pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Blocking of Functional Site

It has been reported that excessive polymer conjugation can lead to a loss of activity of the polypeptide to which the polymer is conjugated. This problem can be eliminated, e.g., by removal of attachment groups located at the functional site or by blocking the functional site prior to conjugation. These latter strategies constitute further embodiments of the invention, the first strategy being exemplified further above, e.g. by removal of lysine residues which may be located close to the functional site and/or by introducing cysteine residues and/or in vivo glycosylation sites at positions not interfering with functional sites.

More specifically, according to the latter strategy the conjugation between the polypeptide and the non-polypeptide moiety is conducted under conditions where the functional site of the IFNG polypeptide is blocked by a helper molecule capable of binding to the functional site of the polypeptide. Preferably, the helper molecule is one, which specifically recognizes a functional site of the polypeptide, such as a receptor. Alternatively, the helper molecule may be an antibody, in particular a monoclonal antibody recognizing the polypeptide exhibiting IFNG activity. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such, as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, a sugar moiety, an organic derivatizing agent or any other compound is conducted in the normal way, e.g. as described in the sections above entitled "Conjugation to . . . " and "Coupling to . . . ".

In a further embodiment the helper molecule is first covalently linked to a solid phase such as column packing materials, for instance Sephadex or agarose beads, or a surface, e.g. reaction vessel. Subsequently, the polypeptide is loaded onto the column material carrying the helper molecule and conjugation carried out according to methods known in the art, e.g. as described in the sections above entitled "Conjugation to . . . " and "Coupling to . . . ". This procedure allows the conjugated polypeptide to be separated from the helper molecule by elution. The conjugated polypeptide is eluted by conventional techniques under physico-chemical conditions that do not lead to a substantive degradation of the conjugated polypeptide. The fluid phase containing the conjugated polypeptide is separated from the solid phase to which the helper molecule remains covalently linked. The separation can be achieved in other ways: For instance, the helper molecule may be derivatized with a second molecule (e.g. biotin) that can be recognized by a specific binder (e.g. streptavidin). The specific binder may be linked to a solid phase thereby allowing the separation of the conjugated polypeptide from the helper molecule-second molecule complex through passage over a second helper-solid phase column which will retain, upon subsequent elution, the helper molecule-second molecule complex, but not the polypeptide conjugate. The conjugated polypeptide may be released from the helper molecule in any appropriate fashion. De-protection may be achieved by providing conditions in which the helper molecule dissociates from the functional site of the IFNG to which it is bound. For instance, a complex between an antibody to which a polymer is conjugated and an anti-idiotypic antibody can be dissociated by adjusting the pH to an acid or alkaline pH.

Methods of Preparing Interferon Gamma Variants of the Invention

The IFNG polypeptide variant, preferably in glycosylated form, may be produced by any suitable method known in the art. Such methods include constructing a nucleotide sequence encoding the polypeptide and expressing the sequence in a suitable transformed or transfected host. However, polypeptides of the invention may be produced, albeit less efficiently, by chemical synthesis or a combination of chemical synthesis or a combination of chemical synthesis and recombinant DNA technology.

The nucleotide sequence of the invention encoding an IFNG polypeptide (in monomer or single chain form) may be constructed by isolating or synthesizing a nucleotide sequence encoding the parent IFNG, such as huIFNG with the amino acid sequence SEQ ID NO:1, and then changing the nucleotide sequence so as to effect introduction (i.e. insertion or substitution) or deletion (i.e. removal or substitution) of the relevant amino acid residue(s).

The nucleotide sequence is conveniently modified by site-directed mutagenesis in accordance with well-known methods, see, e.g., Mark et al., "Site-specific Mutagenesis of the Human Fibroblast Interferon Gene", Proc. Natl. Acad. Sci. USA, 81, pp. 5662-66 (1984); and U.S. Pat. No. 4,588,585.

Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction (LCR). The individual oligonucleotides typically contain 5' or 3' overhangs for complementary assembly.

Once assembled (by synthesis, site-directed mutagenesis or another method), the nucleotide sequence encoding the polypeptide is inserted into a recombinant vector and operably linked to control sequences necessary for expression of the IFNG in the desired transformed host cell.

It should of course be understood that not all vectors and expression control sequences unction equally well to express the nucleotide sequence encoding an IFNG polypeptide described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also e considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector may be an autonomously replicating vector, i.e. a vector which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the IFNG polypeptide is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pCDNA3.1(+)Hyg (Invitrogen, Carlsbad, Calif., USA) and pCI-neo (Stratagene, La Jola, Calif., USA). Useful expression vectors for bacterial hosts include known bacterial plasmids, such as plasmids from *E. coli,* including pBR322, pET3a and pET12a (both from Novagen Inc., WI, USA), wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2µ plasmid and derivatives thereof, the POT1 vector (U.S. Pat. No. 4,931,373), the pJSO37 vector described in (Okkels, Ann. New York Acad. Sci. 782, 202-207, 1996) and pPICZ A, B or C Invitrogen). Useful vectors for insect cells include pVL941, pBG311 (Cate et al., "isolation of the Bovine and Human Genes for Mullerian Inhibiting Substance And Expression of the Human Gene In Animal Cells", Cell, 45, pp. 685-98 (1986), pBluebac 4.5 and pMelbac (both available from Invitrogen) as well as PVL1392 (available from Pharmingen).

Other vectors for use in this invention include those that allow the nucleotide sequence encoding the IFNG polypeptide to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304-19 (1982)) and glutamine synthetase ("GS") amplification (see, e.g., U.S. Pat. No. 5,122,464 and EP 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2µ replication genes REP 1-3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g. ampicillin, kanamycin, tetracyclin, chloramphenicol, neomycin, hygromycin or methotrexate. For filamentous fungi, selectable markers include amdS pyrG, arcB, niaD, sC.

The term "control sequences" is defined herein to include all components, which are necessary or advantageous for the expression of the IFNG polypeptide. Each control sequence may be native or foreign to the nucleic acid sequence encoding the polypeptide. Such control sequences include, but are not limited to, a leader, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus Elb region polyadenylation signals and the Kozak consensus sequence (Kozak, M. *J Mol Biol* Aug. 20, 1987; 196(4):947-50).

In order to improve expression in mammalian cells a synthetic intron may be inserted in the 5' untranslated region of the nucleotide sequence encoding the IFNG polypeptide. An example of a synthetic intron is the synthetic intron from the plasmid pCI-Neo (available from Promega Corporation, WI, USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator.

Examples of suitable control sequences for use in bacterial host cells include promoters of the lac system, the trp system, the TAC or TRC system and the major promoter regions of phage lambda.

The nucleotide sequence of the invention, whether prepared by site-directed mutagenesis, synthesis or other methods, may or may not also include a nucleotide sequence that encode a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with huIFNG) or heterologous (i.e. originating from another source than huIFNG) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as *E. coli*, or eukaryotic, e.g. derived from a mammalian, or insect or yeast cell.

The presence or absence of a signal peptide will, e.g., depend on the expression host cell used for the production of the polypeptide, the protein to be expressed (whether it is an intracellular or intracellular protein) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (cf. WO 90/05783), such as the lepidopteran *Manduca sexta* adipokinetic hormone precursor, (cf. U.S. Pat. No. 5,023,328), the honeybee melittin (Invitrogen), ecdysteroid UDPglucosyl- transferase (egt) (Murphy et al., Protein Expression and Purification 4, 349-357 (1993) or human pancreatic lipase (hpl) (Methods in Enzymology 284, pp. 262-272, 1997).

A preferred signal peptide for use in mammalian cells is that of huIFNG or the murine Ig kappa light chain signal peptide (Coloma, M (1992) J. Imm. Methods 152:89-104). For use in yeast cells suitable signal peptides have been found to be the α-factor signal peptide from *S. cereviciae*. (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), and the yeast aspartic protease 3 (YAP3) signal peptide (cf. M. Egel-Mitani et al., Yeast 6, 1990, pp. 127-137).

Any suitable host may be used to produce the IFNG polypeptide, including bacteria, fungi (including yeasts), plant, insect, mammal, or other appropriate animal cells or cell lines, as well as transgenic animals or plants. Examples of bacterial host cells include grampositive bacteria such as strains of *Bacillus*, e.g. *B. brevis* or *B. subtilis*, *Pseudomonas* or *Streptomyces*, or gramnegative bacteria, such as strains of *E. coli*. The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Examples of suitable yeast host cells include strains of *Saccharomyces*, e.g. *S. cerevisiae*, *Schizosaccharomyces*, *Kluyveromyces*, *Pichia*, such as *P. pastoris* or *P. methlanolica*, *Hansenula*, such as *H. Polymorpha* or *Yarrowia*. Methods for transforming yeast cells with heterologous DNA and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., FEMS Microbiology Letters 99 (1992) 193-198, Manivasakam and Schiestl, Nucleic Acids Research, 1993, Vol. 21, No. 18, pp. 4414-4415 and Ganeva et al., FEMS Microbiology Letters 121 (1994) 159-164.

Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214).

Transformation of insect cells and production of heterologous polypeptides therein may be performed as described by Invitrogen.

Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the IFNG polypeptide.

Methods for introducing exogenous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g. described by Ausbel et al. (eds.), 1996, Current Protocols in Molecular Biology, John Wiley & Sons, New York, USA. The cultivation of mammalian cells are conducted according to established methods, e.g. as disclosed in (Animal Cell Biotechnology, Methods and Protocols, Edited by Nigel Jenkins, 1999, Human Press Inc, Totowa, N.J., USA and Harrison M A and Rae I F, General Techniques of Cell Culture, Cambridge University Press 1997).

In order to produce a glycosylated polypeptide a eukaryotic host cell, e.g. of the type mentioned above, is preferably used.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known n the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered by methods known in the art. For example, the polypeptide may be recovered from the nutrient medium by conventional procedures including, but not limited to, centrifugation, filtration, extraction, spray drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989). Specific methods for purifying polypeptides exhibiting IFNG activity are disclosed in EP 110044 and unexamined Japanese patent application No. 186995/84.

The biological activity of the IFNG polypeptide can be assayed by any suitable method known in the art. Such assays include antibody neutralization of antiviral activity, induction of protein kinase, oligoadenylate 2,5-A synthetase or phosphodiesterase activities, as described in EP 0 041 313 B1. Such assays also include immunomodulatory assays (see, e.g., U.S. Pat. No. 4,753,795), growth inhibition assays, and measurement of binding to cells that express interferon receptors. A specific assay (entitled "primary Assay") is described in the Materials and Methods section herein.

Pharmaceutical Compositions and Uses Thereof

Furthermore, the present invention relates to improved methods of treating, in particular, inflammatory diseases, e.g. interstitial lung diseases, such as idiopathic pulmonary fibrosis, but also granulomatous diseases; cancer, in particular ovarian cancer; infections such as pulmonary atypical mycobacterial infections; bone disorders (e.g. a bone metabolism disorder so as malignant osteopetrosis); autoimmune diseases such as rheumatoid arthritis; as well as other diseases such as multiresistent tuberculosis; cryptococcal meningitis; cystic fibrosis and liver fibrosis, in particular liver fibrosis secondary to hepatitis C; asthma; lymphoma; the key advantages being less frequent and/or less intrusive administration of more efficient therapy, and optionally a lower risk of immune reactions with the therapeutically active compound(s).

The molecule of the invention is preferably administered in a composition including a pharmaceutically acceptable carrier or excipient. "Pharmaceutically acceptable" means a carrier or excipient that does not cause any untoward effects in patients to whom it is administered. Such pharmaceutically acceptable carriers and excipients are well known in the art (Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The molecules of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The polypeptide of the invention is administered at a dose approximately paralleling that employed in therapy with known commercial preparations of IFNG, such as Actimmune®, or as specified in EP 0 795 332. The exact dose to be administered depends on the circumstances. Normally, the dose should be capable of preventing or lessening the severity or spread of the condition or indication being treated. It will be apparent to those of skill in the art that an effective amount of the IFNG polypeptide or composition of the invention depends, inter alia, upon the disease, the dose, the administration schedule, whether the polypeptide or composition is administered alone or in conjunction with other therapeutic agents, the serum half-life/functional in vivo half-life of the compositions, and the general health of the patient.

The present invention also relates to an IFNG polypeptide according to the present invention or a pharmaceutical composition according to the present invention for use as a medicament.

Furthermore, the invention also relates to the use of i) an IFNG variant according to the present invention, or ii) a pharmaceutical composition of the invention, for the manufacture of a medicament, a pharmaceutical composition or a kit-of-parts for the treatment of diseases selected from the group consisting of inflammatory diseases, such as interstitial lung diseases, in particular idiopathic pulmonary fibrosis; cancer, in particular ovarian cancer; infections, such as pulmonary atypical mycobacterial infections; bone disorders (e.g. a bone metabolism disorder so as malignant osteopetrosis); granulomatous diseases; autoimmune diseases such as rheumatoid arthritis; multiresistent tuberculosis; cryptococcal meningitis; cystic fibrosis and liver fibrosis, in particular liver fibrosis secondary to hepatitis C; asthma and lymphoma. Most preferably the disease is an interstitial lung disease, in particular idiopathic pulmonary fibrosis.

A glucocorticoid such as prednisolone may also be included. The preferred dosing is 1-4, more preferably 2-3, µg/kg patient weight of the polypeptide component per dose. The preferred dosing is 100-350, more preferably 100-150 µg glucocorticoid/kg patient weight per dose.

Also disclosed are improved means of delivering the molecules or preparations, optionally additionally comprising glucocorticoids.

The invention also relates to a kit of parts suitable for the treatment of interstitial lung diseases comprising a first pharmaceutical composition comprising the active components i) or ii) mentioned above and a second pharmaceutical composition comprising at least one glucocorticoid, each optionally together with a pharmaceutically acceptable carrier and/or excipient.

The variant of the invention can be formulated into pharmaceutical compositions by well-known methods. Suitable formulations are described by Remington's Pharmaceutical Sciences by E. W. Martin and U.S. Pat. No. 5,183,746.

The pharmaceutical composition may be formulated in a variety of forms, including liquid, gel, lyophilized, powder, compressed solid, or any other suitable form. The preferred form will depend upon the particular indication being treated and will be apparent to one of skill in the art. However, the IFNG polypeptide of the invention is preferably formulated as a liquid pharmaceutical composition.

The pharmaceutical composition may be administered orally, subcutaneously, intravenously, intracerebrally, intranasally, transdermally, intraperitoneally, intramuscularly, intrapulmonary, vaginally, rectally, intraocularly, or in any other acceptable manner, e.g. using PowderJect or ProLease technology. The formulations can be administered continuously by infusion, although bolus injection is acceptable, using techniques well known in the art, such as pumps or implantation. In some instances the formulations may be directly applied as a solution or spray. The preferred mode of administration will depend upon the particular indication being treated and will be apparent to one of skill in the art, but usually subcutaneous administration is preferred as this mode of administration can typically be conducted by the patient himself.

The pharmaceutical composition of the invention may be administered in conjunction with other therapeutic agents. These agents may be incorporated as part of the same pharmaceutical composition or may be administered separately from the polypeptide of the invention, either concurrently or in accordance with any other acceptable treatment schedule. In addition, the polypeptide or pharmaceutical composition of the invention may be used as an adjunct to other therapies. In particular, combinations with glucocorticoids as described in EP 0 795 332 are considered.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), PLURONIC® polyols, polyoxyethylene sorbitan monoethers (TWEEN®-20 polysorbate surfactant, TWEEN®-80 polysorbate surfactant, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

In a preferred embodiment of the invention said pharmaceutical composition comprises the i) IFNG variant of the invention, ii) a buffering agent, in particular a salt of an organic acid, capable of maintaining the pH between 4.5-7.5, iii) a stabilizer, in particular an organic sugar or sugar alcohol, iv) a non-ionic surfactant, and v) sterile water. Preferably, the buffering agent is capable of maintaining the pH between 5.0-7.5, more preferably between 5.0-7.0, in particular between 5.0-6.5. More particularly, the buffering agent is selected from the group consisting of acetate, succinate and citrate, the stabilizer is mannitol or sorbitol, the non-ionic surfactant is Tween®-20 or Tween®-80. Preferably, the pharmaceutical composition does not include any preservatives.

In a highly preferred embodiment of the invention, the pharmaceutical composition comprises an sulfoalkyl ether cyclodextrin derivative, such as any of the derivatives described in U.S. Pat. Nos. 5,874,418, 5,376,645 and 5,134,127, the contents of which are incorporated herein by reference. In one embodiment of the invention the sulfoalkyl ether cyclodextrin is a compound of the Formula (I):

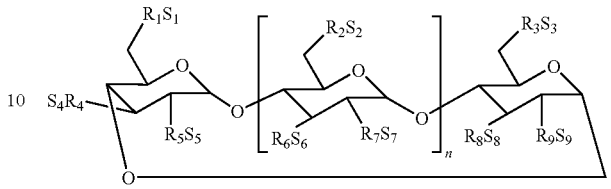

wherein n is 4, 5 or 6, $R_1, R_2, R_3, R_4, R_5, R_6, R_7, R_8$, and $R_9$ are each, independently, —O— or a —O—$(C_2$-$C_6$ alkylene)-$SO_3$— group, wherein at least one of $R_1$ and $R_2$ is independently a —O—$(C_2$-$C_6$ alkylene)-$SO_3$— group, and $S_1, S_2, S_3, S_4, S_5, S_6, S_7, S_8$, and $S_9$ are each, independently, a pharmaceutically acceptable cation.

In a further embodiment n is 5. In a still further embodiment n is 6.

In a further embodiment at least one of $R_1$ and $R_2$ is —O—$(CH_2)_m$—$SO_3$—, and m is 2, 3, 4, 5 or 6. In a further embodiment $R_1$ and $R_2$ is independently selected from —OCH$_2$CH$_2$CH$_2$SO$_3$— or —OCH$_2$CH$_2$CH$_2$CH$_2$SO$_3$—.

In a further embodiment at least one of $R_4$, $R_6$, and $R_8$, is independently, —O—$(C_2$-$C_6$ alkylene)-$SO_3$—; and $R_5$, $R_7$, and $R_9$ are all —O—.

In a further embodiment $S_1, S_2, S_3, S_4, S_5, S_6, S_7, S_8$, and $S_9$ are each, independently, a pharmaceutically acceptable cation selected from $H^+$, alkali metals (e.g. $Li^+$, $Na^+$, $K^+$), alkaline earth metals (e.g., $Ca^{+2}$, $Mg^{+2}$), ammonium ions and amine cations such as the cations of $(C_1$-$C_6)$ alkylamines, piperidine, pyrazine, $(C_1$-$C_6)$ alkanolamine and $(C_4$-$C_8)$cycloalkanolamine.

In a further embodiment $S_1, S_2, S_3, S_4, S_5, S_6, S_7, S_8$, and $S_9$ are independently selected from alkaline metal cation, alkaline earth metal cation, quaternary ammonium cation, tertiary ammonium cation, and secondary ammonium cation.

In a further embodiment at least one of $R_4$, $R_6$, and $R_8$, is independently, —O—$(C_2$-$C_6$ alkylene)-$SO_3$—; and $R_5$, $R_7$, and $R_9$ are all —O—.

The terms "alkylene" and "alkyl," as used herein (e.g., in the —O—$(C_2$-$C_6$-alkylene)$SO_3$— group or in the alkylamines), include linear, cyclic, and branched, saturated and unsaturated (i.e., containing a double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The presently preferred sulfoalkyl ether cyclodextrin derivative is a salt of beta cyclodextrin sulfobutyl ether (in particular the sodium salt thereof also termed SBE7-β-CD which is available as CAPTISOL® cyclodextrin) (Cydex, Overland Park, Kans. 66213, US).

Sustained Release Preparations

Suitable examples of sustained-release preparations include semi-permeable matrices of solid hydrophobic polymers containing the variant, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the PROLEASE® technology or LUPRON DEPOT® (injectable microspheres composed of lactic acid-glycolic acid copolymer and leuprolide acetate), and poly-D-(—)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The variants may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g. as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Topical Administration

Formulations suitable for topical administration include liquid or semi-liquid preparations suitable for penetration through the skin (e.g., liniments, lotions, ointments, creams, or pastes) and drops suitable for administration to the eye, ear, or nose.

Pulmonary Delivery

Formulations suitable for use with a nebulizer, either jet or ultrasonic, will typically comprise the polypeptide dissolved in water at a concentration of, e.g., about 0.01 to 25 mg of variant per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. Nos. 5,915,378, 5,960,792, 5,957,124, 5,934,272, 5,915,378, 5,855,564, 5,826,570 and 5,522,385 which are hereby incorporated by reference.

Formulations for use with a metered dose inhaler device will generally comprise a finely divided powder. This powder may be produced by lyophilizing and then milling a liquid variant formulation and may also contain a stabilizer such as human serum albumin (ISA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the variant present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C.

Formulations for powder inhalers will comprise a finely divided dry powder containing variant and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/cm$^2$ having a median diameter less than micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass.

The powders for these devices may be generated and/or delivered by methods disclosed in U.S. Pat. Nos. 5,997,848, 5,993,783, 5,985,248, 5,976574, 5,922,354, 5,785,049 and 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkermes, Cambridge, Mass.; and the AERx pulmonary drug delivery system manufactured by Aradigm Corporation, Hayward, Calif.

The invention provides compositions and methods for treating bacterial and viral infections, cancers or tumors, interstitial pulmonary diseases such as idiopathic pulmonary fibrosis, granulomatous diseases, bone disorders (e.g. a bone metabolism disorder so as malignant osteopetrosis) and autoimmune diseases such rheumatoid arthritis.

In a further aspect the invention relates to a method of treating a mammal having circulating antibodies against huIFNG, which method comprises administering a compound which has the bioactivity of IFNG and which does not react with said antibodies. The compound is preferably a variant as described herein and the mammal is preferably a human being. The mammals to be treated may suffer from any of the diseases listed above for which IFNG is a useful treatment. Furthermore, the invention relates to a method of making a pharmaceutical product for use in treatment of mammals having circulating antibodies against huIFNG, wherein a compound which has the bioactivity of IFNG and which does not react with such is formulated into an injectable or otherwise suitable formulation. The term "circulating antibodies" is intended to indicate autoantibodies formed in a mammal in response to having been treated with any of the commercially available IFNG preparations.

Also contemplated is use of a nucleotide sequence encoding an IFNG polypeptide of the invention in gene therapy applications. In particular, it may be of interest to use a nucleotide sequence encoding an IFNG polypeptide described in the section above entitled "Glycosylated Polypeptides of the Invention modified to incorporate additional glycosylation sites". The glycosylation of the polypeptide is thus achieved during the course of the gene therapy, i.e. after expression of the nucleotide sequence in the human body.

Gene therapy applications contemplated include treatment of those diseases in which the polypeptide is expected to provide an effective therapy.

Local delivery of IFNG using gene therapy may provide the therapeutic agent to the target area while avoiding potential toxicity problems associated with non-specific administration.

Both in vitro and in vivo gene therapy methodologies are contemplated.

Several methods for transferring potentially therapeutic genes to defined cell populations are known. For further reference see, e.g., Mulligan, "The Basic Science Of Gene Therapy", Science, 260, pp. 926-31 (1993). These methods include:

Direct gene transfer, e.g., as disclosed by Wolff et al., "Direct Gene transfer Into Mouse Muscle In vivo", Science 247, pp. 1465-68 (1990);

Liposome-mediated DNA transfer, e.g., as disclosed by Caplen et al., "Uposome-mediated CFFR Gene Transfer to the Nasal Epithelium Of Patients With Cystic Fibrosis" Nature Med., 3, pp. 39-46 (1995); Crystal, "The Gene As A Drug", Nature Med., 1, pp. 15-17 (1995); Gao and Huang, "A Novel Cationic Liposome Reagent For Efficient Transfection of Mammalian Cells", Biochem. Biophys Res. Comm., 179, pp. 280-85 (1991);

Retrovirus-mediated DNA transfer, e.g., as disclosed by Kay et al., "In vivo Gene Therapy of Hemophilia B: Sustained Partial Correction In Factor IX-Deficient Dogs", Science, 262, pp. 117-19 (1993); Anderson, "Human Gene Therapy", Science, 256, pp.808-13(1992);

DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses as Vectors for Gene Therapy", Gene Therapy, 1, pp. 367-84 (1994); U.S. Pat. Nos. 4,797,368, and 5,139,941.

The invention is further described in the following examples. The examples should not, in any manner, be understood as limiting the generality of the present specification and claims.

MATERIALS AND METHODS

Materials

CHO-K1 cells (available from American Type Culture Collection (ATCC #CCL-61)).

HeLa cells (available from American Type Culture Collection (ATCC #CCL-2)).

ISRE-Luc was obtained from Stratagene, La Jolla USA.

pCDNA 3.1/hygro was obtained from Invitrogen, Carlsbad USA.

Restriction enzymes and polymerases were obtained from New England Biolabs Inc., Beverly, USA.

DMEM medium: Dulbecco's Modified Eagle Media (DMEM), 10% fetal bovine serum and Hygromycin B were obtained from Life Technologies A/S, Copenhagen, Denmark.

LucLite substrate was obtained from Packard Bioscience, Groningen, The Netherlands.

TopCount luminometer was obtained from Packard Bioscience, Groningen, The Netherlands.

Biotinylated polyclonal anti-human IFNG antibody, BAF285, was obtained available from R&D Systems Inc., Minneapolis, USA.

Horse Radish Peroxidase-conjugated streptavidin, P0397, was obtained from DAKO, Copenhagen, Denmark.

TMB blotting reagent was obtained from KEM-EN-TEC, Copenhagen, Denmark.

Methods

Interferon Assay Outline

It has previously been published that IFNG interacts with and activates IFNG receptors on HeLa cells. Consequently, transcription is activated at promoters containing an Interferon Stimulated Response Element (ISRE). It is thus possible to screen for agonists of interferon receptors by use of an ISRE coupled luciferase reporter gene (ISRE-luc) placed in HeLa cells.

Primary Assay

HeLa cells are co-transfected with ISRE-Luc and pCDNA 3.1/hygro and foci (cell clones) are created by selection in DMEM media containing Hygromycin B. Cell clones are screened for luciferase activity in the presence or absence of IFNG. Those clones showing the highest ratio of stimulated to unstimulated luciferase activity are used in further assays.

To screen polypeptides, 15,000 cells/well are seeded in 96 well culture plates and incubated overnight in DMEM media. The next day the polypeptides as well as a known standard are added to the cells in various concentrations. The plates are incubated for 6 hours at 37° C. in a 5% $CO_2$ air atmosphere LucLite substrate (Packard Bioscience, Groningen, The Netherlands) is subsequently added to each well. Plates are sealed and luminescence measured on a TopCount luminometer (Packard) in SPC (single photon counting) mode.

Each individual plate contains wells incubated with IFNG as a stimulated control and other wells containing normal media as an unstimulated control. The ratio between stimulated and unstimulated luciferase activity serves as an internal standard for both IFNG activity and experiment-to-experiment variation.

Determination of Increased Degree of Glycosylation

To determine the various degrees of glycosylation of IFNG monomers, a SDS-PAGE gel is run under standard conditions and transferred to a nitrocellulose membrane. Western blotting is done according to standard procedures using a biotinylated polyclonal anti-human IFNG antibody (BAF285 from R & D Systems) as primary antibody and Horse Radish Peroxidase-conjugated streptavidin (P0397from DAKO) as secondary antibody followed by staining with TNB blotting reagent (KEM-EN-TEC, Copenhagen, Denmark). The distribution of IFNG monomers having varying degrees of glycosylation is made by visual inspection of the stained membrane.

Determination of $AUC_{sc}$

The $AUC_{sc}$ is determined by one 200 µl bolus subcutaneous administration of equal amount (on an activity basis) of the IFNG polypeptide of the invention in rats.

For these experiments, female Sprag-Dawley rats, weighing between 220-260 grams, are used. The IFNG polypeptide is formulated in sodium succinate (720 mg/l), mannitol 40 g/l), polysorbat 20 (100 mg/l) at pH 6.0.

Before subcutaneous administration, one blood sample is drawn in the tail-vein to ensure that no background IFNG activity can be detected. After administration, blood samples are withdrawn from the tail vein after 10 min, 20 min, 40 min, 60 min, 120 min, 240 min, 480 min, 720 min, 1440 min, 1620 min, 1920 min and 2880 min (sometimes also 3600 min). Serum is prepared by letting the blood sample coagulate for 20 min at room temperature followed by centrifugation at 5000 g, 20 min at room temperature. The serum is then isolated and stored at −80° C. until determination of IFNG activity using the "Primary Assay" described above.

The amount of units in serum (U/ml) against time (min) is then plotted and the $AUC_{sc}$ is calculated using GraphPad Prism 3.01.

Similar experiments are performed on glycosylated huIFNG, glycosylated [S99T]huIFNG and/or Actimmune® in order to assess the increase in $AUC_{sc}$ of the IFNG polypeptide of the invention as compared to glycosylated huIFNG, glycosylated [S99T]huIFNG and/or Actimmune®.

Functional in Vivo Half-Life

The functional in vivo half-life is determined by one 200 µl bolus intravenous administration of equal amount (on an activity basis) of the IFNG polypeptide of the invention in rats.

For these experiments, female Sprag-Dawley rats, weighing between 220-260 grams, are used. The IFNG polypeptide is formulated in sodium succinate (720 mg/l), mannitol 40 g/l), polysorbat 20 (100 mg/l) at pH 6.0.

Before intravenous administration, one blood sample is drawn in the tail-vein to ensure that no background IFNG activity can be detected. After administration in one tail vein, blood samples are withdrawn from the other tail vein after 5 min, 10 min, 20 min, 40 min, 60 min, 120 min, 240 min, 480 min, 720 min, 1440 min, 1620 min, 1920 min and 2880 min. Serum is prepared by letting the blood sample coagulate for 20 min at room temperature followed by centrifugation at 5000 g, 20 min at room temperature. The serum is then isolated and stored at −80° C. until determination of IFNG activity using the "Primary Assay" described above.

The amount of units in serum (U/ml) against time (min) is then plotted and the functional in vivo half-life is calculated using WinNonLin Pro 3.3.

Similar experiments are performed on glycosylated huIFNG, glycosylated [S99T]huIFNG and/or Actimmune® in order to assess the increase in functional in vivo half-life of the IFNG polypeptide of the invention as compared to glycosylated huIFNG, glycosylated [S99T]huIFNG and/or Actimmune®.

Identification of Surface Exposed Amino Acid Residues

Structures

Experimental 3D structures of huIFNG determined by X-ray crystallography have been reported by: Ealick et al. Science 252:698-702 (1991) reporting on the C-alpha trace of an IFNG homodimer. Walter et. al. Nature 376:230-235 (1995) reporting on the structure of an IFNG homodimer in complex with two molecules of a soluble form of the IFNG receptor. The coordinates of this structure have never been made publicly available. Thiel et. al. Structure 8:927-936 (2000) reporting on the structure of an IFNG homodimer in complex with two molecules of a soluble form of the IFNG receptor having a third molecule of the receptor in the structure not making interactions with the IFNG homodimer.

Accessible Surface Area (ASA)

The computer program Access (B. Lee and F. M. Richards, J. Mol. Biol. 55: 379-400 (1971)) version 2 (Copyright (c) 1983 Yale University) was used to compute the accessible surface area (ASA) of the individual atoms in the structure. This method typically uses a probe-size of 1.4 Å and defines the Accessible Surface Area (ASA) as the area formed by the centre of the probe. Prior to this calculation all water molecules, hydrogen atoms and other atoms not directly related to the protein are removed from the coordinate set.

Fractional ASA of Side Chain

The fractional ASA of the side chain atoms is computed by division of the sum of the ASA of the atoms in the side chain with a value representing the ASA of the side chain atoms of that residue type in an extended ALA-x-ALA tripeptide. See Hubbard, Campbell & Thornton (1991) J. Mol. Biol.: 220, 507-530. For this example the CA atom is regarded as a part of the side chain of Glycine residues but not for the remaining residues. The following table are used as standard 100% ASA for the side chain:

| | | |
|---|---|---|
| Ala | 69.23 | Å² |
| Arg | 200.35 | Å² |
| Asn | 106.25 | Å² |
| Asp | 102.06 | Å² |
| Cys | 96.69 | Å² |
| Gln | 140.58 | Å² |
| Glu | 134.61 | Å² |
| Gly | 32.28 | Å² |
| His | 147.00 | Å² |
| Ile | 137.91 | Å² |
| Leu | 140.76 | Å² |
| Lys | 162.50 | Å² |
| Met | 156.08 | Å² |
| Phe | 163.90 | Å² |
| Pro | 119.65 | Å² |
| Ser | 78.16 | Å² |
| Thr | 101.67 | Å² |
| Trp | 210.89 | Å² |
| Tyr | 176.61 | Å² |
| Val | 114.14 | Å² |

Residues not detected in the structure are defined as having 100% exposure as they are thought to reside in flexible regions.

Determining Distances Between Atoms:

The distance between atoms was determined using molecular graphics software e.g. InsightII v. 98.0, MSI INC.

Determination of Receptor Binding Site:

The receptor-binding site is defined as comprising of all residues having their accessible surface area changed upon receptor binding. This is determined by at least two ASA calculations; one on the isolated ligand(s) in the ligand(s)/receptor(s) complex and one on the complete ligand(s)/receptor(s) complex.

EXAMPLES

Example 1

Determination of Surface-Exposed Amino Acids

The X-ray structure used was of an IFNG homo-dimer in complex with two molecules of a soluble form of the IFNG receptor having a third molecule of the IFNG receptor in the structure not making interactions with the IFNG homodimer reported by Thiel et. al. Structure 8:927-936 (2000). The structure consists of the IFNG homodimer wherein the two molecules are labeled A and B. For construction purposes there is an additional methionine placed before the IFNG sequence labeled MO and the sequence is C-terminally truncated with ten residues (Q133 being the last residue in the constructed molecules). The M0 is removed from the structure in all the calculations of this example. The structure of the two IFNG monomers has very weak electron density after residue 120 and residues were only modeled until residue T126. Therefore, residues S121-T126 were removed from the structure prior to the calculations in this example. The two receptor fragments labeled C and D make direct interactions with the IFNG homodimer and a third receptor molecule labeled E makes no contact with the IFNG homodimer and are not included in these calculations.

Surface Exposure:

Performing fractional ASA calculations on the homodimer of molecules A and B excluding M0 and S121-T126 in both molecules resulted in the following residues having more than 25% of their side chain exposed to the surface in at least one of the monomers: Q1, D2, P3, K6, E9, N10, K12, K13, Y14, N16, G18, H19, S20, D21, A23, D24, N25, G26, T27, G31, K34, N35, K37, E38, E39, S40, K55, K58, N59, K61, D62, D63, Q64, S65, Q67, K68, E71, T72, K74, E75, N78, V79, K80, N83, S84, N85, K86, K87, D90, E93, K94, N97, S99, T101, D102, L103, N104, H11, Q115, A118 and E119.

The following residues had more than 50% of their side chain exposed to the surface in at least one of the monomers: Q1, D2, P3, K6, E9, N10, K13, N16, G18, H19, S20, D21, A23, D24, N25, G26, T27, G31, K34, K37, E38, E39, K55, K58, N59, D62, Q64, S65, K68, E71, E75, N83, S84, K86, K87, K94, N97, S99, T101, D102, L103, N104, Q115, A118, E119.

Performing fractional ASA calculations on the homodimer of molecules A and B excluding M0 and S121-T126 in both molecules and including the receptor molecules C and D resulted in the following residues had more than 25% of their side chain exposed to the surface in at least one of the monomers: Q1, D2, P3, K6, E9, N10, K13, Y14, N16, G18, H19, D21, N25, G26, G31, K34, N35, K37, E38, E39, S40, K55, K58, N59, K61, D62, D63, Q64, S65, Q67, K68, E71, T72, K74, E75, N78, V79, K80, N83, S84, N85, K86, K87, D90, E93, K94, N97, S99, T101, D102, L103, N104, E119.

The following residues had more than 50% of their side chain exposed to the surface in at least one of the monomers: P3, K6, N10, K13, N16, D21, N25, G26, G31, K34, K37, E38, E39, K55, K58, N59, D62, Q64, S65, K68, E71, E75, N83, S84, K86, K87, K94, N97, S99, T101, D102, L103 and N104.

All of the above positions are targets for modification in accordance with the present invention.

Comparing the two lists, results in K12, S20, A23, D24, T27, H111, Q115 and A118 being removed from the more than 25% side chain ASA list upon receptor binding, and Q1, D2, E9, G18, H19, S20, A23, D24, T27, Q 115, A118 and E119 being removed from the more than 50% side chain ASA list upon receptor binding.

Residues not determined in the structure are treated as fully surface exposed, i.e. residues S121, P122, A123, A124, K125, T126, G127, K128, R129, K130, R131, S132, Q133, M134, L135, F136, R137, G138, R139, R140, A141, S142, Q143. These residues also constitute separate targets for introduction of attachment groups in accordance with the present invention (or may be viewed as belonging to the group of surface exposed amino acid residues, e.g. having more than 25% or more than 50% exposed side chains).

Example 2

Determination of Receptor Binding Site

Performing ASA calculations as described above results in the following residues of the IFNG molecule having reduced ASA in at least one of the monomers in the complex as compared to the calculation on the isolated dimer: Q1, D2, Y4, V5, E9, K12, G18, H19, S20, D21, V22, A23, D24, N25, G26, T27, L30, K34, K37, K108, H111, E112, I114, Q115, A118, E119.

Example 3

Design of an Expression Cassette for Expression of IFNG with Codon Usage Optimised for CHO Cells The DNA sequence, GenBank accession number X13274, encompassing a full length cDNA encoding mature huIFNG with its native signal peptide, was modified in order to facilitate high expression in CHO cells. Codons of the huIFNG nucleotide sequence were modified by making a bias in the codon usage towards the codons frequently used in *homo sapiens*. Subsequently, certain nucleotides in the sequence were substituted with others in order to introduce recognition sites for DNA restriction endonucleases. Primers were designed such that the gene could be synthesised.

The primers were assembled to the synthetic gene by one step PCR using Platinum Pfx-polymerase kit (Life Technologies) and standard three-step PCR cycling parameters. The assembled gene was amplified by PCR using the same conditions and has the sequence shown in SEQ ID NO:4. The synthesised gene was cloned into pcDNA3.1/hygro (InVitrogen) between the BamHI at the 5' end and the XbaI at the 3' end, resulting in pIGY-22.

Example 4

Site Directed Mutagenesis

Generation of N-glycosylation Variants

To introduce mutations/optimise N-glycosylation sites in IFNG, oligonucleotides were designed in such a way that PCR generated changes could be introduced in the expression plasmid (pIGY-22) by classical two-step PCR followed by subcloning the PCR fragment using BamHI and XbaI.

Two vector primers were designed to be used with specific mutation primers: ADJ013: 5'-GATGGCTGGCAACTA-GAAG-3' (SEQ ID NO: 5) (antisense downstream vector primer); and ADJ014: 5'-TGTACGGTGGGAGGTCTAT-3' (SEQ ID NO: 6) (sense upstream vector primer)

To optimize the native N-glycosylation site at position 97 and in order to introduce an additional N-glycosylation site at position 38, the following primers were designed:

```
S99T:
                                          (SEQ ID NO: 7)
ADJ093 5'-GTTCAGGTCTGTCACGGTGTAATTGGTCAGCTT-3'

(SEQ ID NO: 8)
ADJ094 5'-AAGCTGACCAATTACACCGTGACAGACCTGAAC-3;

E38N + S40T:
                                          (SEQ ID NO: 9)
ADJ091 5'-CATGATCTTCCGATCGGTCTCGTTCTTCCAATT-3'

(SEQ ID NO: 10)
ADJ092 5'-AATTGGAAGAACGAGACCGATCGGAAGATCATG-3'
```

The S99T variant was generated by classical two-step PCR as described above, using ADJ013 and ADJ014 as vector primers, ADJ093 and ADJ094 as mutation primers, and pIGY-22 as template. The 447 bp PCR fragment was subcloned into pcDNA3.1/Hygro (InVitrogen) using BamHI and XbaI, leading to plasmid pIGY48.

The E38N+S40T+S99T variant was generated by classical two-step PCR as described above, using ADJ013 and ADJ014 as vector primers, ADJ091 and ADJ092 as mutation primers, and pIGY-48 as template. The 447 bp PCR fragment was subcloned into pcDNA3.l/Hygro (InVitrogen) using BamHI and XbaI, leading to plasmid pIGY-54.

Generation of the C-Terminally Modified IFNG Variants

C-terminally modified IFNG variants were generated by one-step PCR using pIGY-54 as template (i.e. including the E38N+S40T+S99T mutations). An 'upstream' oligonucleotide containing the start codon (preceded by a BamHI site for cloning and the sequence GCCGCCACC (SEQ ID NO: 13) in order to optimise mRNA translation) and a 'downstream' oligonucleotide containing the desired mutation(s) and a XbaI site were used as primers.

In order to optimize protein production, a pcDNA3.1(+)/Hygro(InVitrogen)-derivative plasmid containing an intron from pCI-Neo (Stratagene) was used as expression vector. This vector, termed PF033, was constructed by PCR amplification of the intron from pCI-Neo using 5'-CCGTCA-GATCCTAGGCTAGCTTATTGCGGTAGTTTATCAC-3' (SEQ ID NO: 11) and 5'-GAGCTCGGTACCAAGCTTT-TAAGAGCTGTAAT-3' (SEQ ID NO: 12) as primers, followed by subcloning of the PCR product into pcDNA3.1(+)/Hygro using NheI and HindIII. The mutated IFNG PCR products were subcloned into PF033 using BamHI and XbaI.

Using this approach the following variants were prepared:
E38N+S40T+S99T+R137P (reference)
E38N+S40T+S99T+R139P (reference)
E38N+S40T+S99T+R140P (reference)
E38N+S40T+S99T+S142P (reference)
E38N+S40T+S99T+R137P+R139P+Q143P (reference)
E38N+S40T+S99T+R137P+R139P+S142P
E38N+S40T+S99T+R137P+S142P
E38N+S40T+S99T+S132P+R137P+R140P
E38N+S40T+S99T+S132P+R140P
E38N+S40T+S99T+R140P (reference)
E38N+S40T+S99T+R137P+R140P Example 5

Expression of IFNG Polypeptides in Mammalian Cells

For transient expression of the IFNG polypeptide, cells were grown to 95% confluency in serum-containing media (Dulbecco's MEM/Nut.-mix F-12 (Ham) L-glutamine, 15 mM Hepes, pyridoxine-HCl (Life Technologies Cat # 31330-038)) containing 1:10 FBS (BioWhittaker Cat # 02-701F) and 1:100 penicillin and streptomycin (BioWhittaker Cat # 17-602E). IFNG-encoding plasmids were transfected into the cells using Lipofectamine 2000 Wife Technologies) according to the manufacturer's specifications. 24 hrs after transfection, culture media were collected and assayed for IFNG activity. Furthermore, in order to quantify the relative number of glycosylation sites utilized, Western blotting is performed using harvested culture medium.

Stable clones expressing the IFNG polypeptide are generated by transfection of CHO K1 cells with IFNG-encoding plasmids followed by incubation of the cells in media containing 0.36 mg/ml hygromycin. Stably transfected cells are isolated and sub-cloned by limited dilution. Clones producing high levels of IFNG are identified by ELISA.

Example 6

Large-Scale Production

Stable cell lines expressing the IFNG polypeptide are grown in Dulbecco's MEM/Nut.-mix F-12 (Ham) L-glutamine, 15 mM Hepes, pyridoxine-HCl (Life Technologies Cat # 31330-038), 1:10 FBS (BioWhittaker Cat # 02-701F), 1:100 penicillin and streptomycin (BioWhittaker Cat # 17-602E) in 1700 cm2 roller bottles (Corning, # 431200) until confluence. The media is then changed to 300 ml UltraCHO with L-glutamine (BioWhittaker Cat # 12-724Q) with the addition of 1:500 EX-CYTE VLE (Serological Proteins Inc. # 81-129) and 1:100 penicillin and streptomycin (BioWhittaker Cat # 17-602E). After 48 hours of growth, the media is replaced with fresh UltraCHO with the same additives. After another 48 hours of growth, the media is replaced with Dulbecco's MEM/Nut.-mix F-12 (Ham) L-glutamine, pyridoxine-HCl (Life Technologies Cat # 21041-025) with the addition of 1:500 ITS-A (Gibco/BRL# 51300-044), 1:500 EX-CYTE VIE (Serological Proteins Inc. # 81-129) and 1:100 penicillin and streptomycin (BioWhittaker Cat # 17-602E). Subsequently, every 24 h, culture media are harvested and replaced with 300 ml of the same serum-free media. The collected media are filtered through 0.22 µm filters to remove cells.

Example 7

Purification

The filtrate was microfiltrated (0.22 µm) before ultrafiltration to approximately 1/20 volume using a Millipore Liz system. On the same system the concentrate was diafiltrated using 10 mM Tris, pH 7.6. Ammonium sulphate was added to a concentration of 2.1 M and after stirring the precipitate was removed by centrifugation at 8000 rpm for 25 minutes in a Sorvall centrifuge using a GS3 rotor.

The supernatant was applied onto an Ether 650M (Toyoperl, Tosohaas) column previously equilibrated in 10 mM Tris, 2.1 M ammonium sulphate, pH 7.6. The flow-through fraction containing the IFNG variant was loaded directly onto a butyl-sepharose FF (Amersham Biosciences) column pre-equilibrated with, 2.1 M ammonium sulphate, pH 7.6. The column was washed with 2 column volumes of 10 mM Tris, 2.1 M ammonium sulphate, pH 7.6 after application and the bound IFNG variant was then eluted in a linear gradient over 20 column volumes to 100% 10 mM Tris, pH 7.6. Fractions enriched in the IFNG variant were pooled and buffer exchanged by diafiltration into 10 mM Tris, pH 8.8, using a Vivaflow200 system (VivaScience) with a molecular weight cut-off of 10,000 Da.

The IFNG variant was then applied onto a Q-sepharose FF (Amersham Biosciences) column previously equilibrated in 10 mM Tris, pH 8.8. After application the column was washed with 3 column volumes of 10 mM Tris, pH 8.8 before eluting the bound IFNG variant in a gradient from 0-30% 10 mM Tris-HCl, 1 M NaCl, pH 8.8, over 25 column volumes. Fractions containing the IFNG variant were pooled and buffer exchanged into 5 mM sodium succinate, 4% mannitol, pH 6.0, using a VivaSpin20 column (VivaScience) and Tween 20 was subsequently added to a concentration of 0.01%. The IFNG variant was sterile filtered and stored at −80° C.

Example 8

Analysis of C-Terminal Truncation

The above-mentioned variants were constructed to study the C-terminal truncation in more detail. The variants were purified from serum-free media as described in Example 5, except that stabile clones from pooled clones were used instead of selected high-expressing single clones. In general, 2500 to 5000 ml media was used to purify the individual variants.

The sterile-filtered media (0.22 µm) were concentrated to approx. 1/15 volume and subsequently diafiltered (to a conductivity <2 mS/cm) using 5 mM sodium phosphate, pH 6.2, on a PALL FILTRON system. The concentrated/diafiltered media was filtered (0.22 µm) to clear the sample from any precipitated material prior to further purification. The pH in the filtrate was adjusted to 6.2 before application onto a 2 ml CM-sepharose Fast Flow (Pharmacia) previously equilibrated in 10 mM sodium phosphate, pH 6.2. The column was washed with 10-15 column volumes 10 mM sodium phosphate, pH 6.2, before step-eluting bound variants with 2-3 column volumes 100 mM sodium phosphate, 500 mM NaCl, pH 7.0.

The step-eluted variants were filtered (0.45 µm) before being immunoprecipitated with an IFNG antibody affinity column. The antibody affinity column was prepared according to the manufacture's instructions by coupling 10 mg monoclonal mouse anti-human IFNG antibody (catalog no. MD-2, U-CyTech, Holland) onto approx. 1.3 ml activated CNBr-sepharose (Pharmacia). The filtered sample from the CM-sepharose column was applied onto the antibody affinity column previously equilibrated with phosphate-buffered saline. The column was then washed with 5 column volumes phosphate buffered saline and the variant was subsequently eluted into a vial already containing 0.15 ml 500 mM sodium phosphate, pH 7.2, using 2 column volumes 100 mM glycine, pH 3.5.

Analysis of C-terminal truncation was done by MALDI-TOF mass spectrometry following enzymatic deglycosylation using the following procedure:

N-linked carbohydrate moieties attached to Asn-residues were removed by treatment of 30 µl of the affinity-purified variant with 1 mU PNGase F (Roche) at 37° C. for 16 h. A 1 µl sample aliquot was mixed with 1 µl matrix solution (saturated α-cyano-4-hydroxy cinnamic acid in 50% acetonitril, 0.1% TFA). Half of the mixture was spotted onto a Thin-Layer of α-cyano-4-hydroxy cinnamic acid on the target plate and air-dried. (The Thin-Layer coating was preformed on the target plate by crystallisation of α-cyano-4-hydroxy cinnamic acid from the Thin-Layer matrix solution (saturated α-cyano-4-hydroxy cinnamic acid in 100% acetone)). The sample spot was washed twice with 1 µl HPLC grade water and air-dried. The sample spot was added 0.2 µl matrix solution and air-dried. Following introduction of the target plate into the mass spectrometer, spectra were recorded at threshold laser power.

MALDI-TOF mass spectrometry was carried out in an Applied Biosystems Voyager-DE Pro mass spectrometer in linear mode using positive ionisation. C-terminal truncation was evaluated by comparing recorded spectra with the expected mass of the purified variant.

Figure 2:
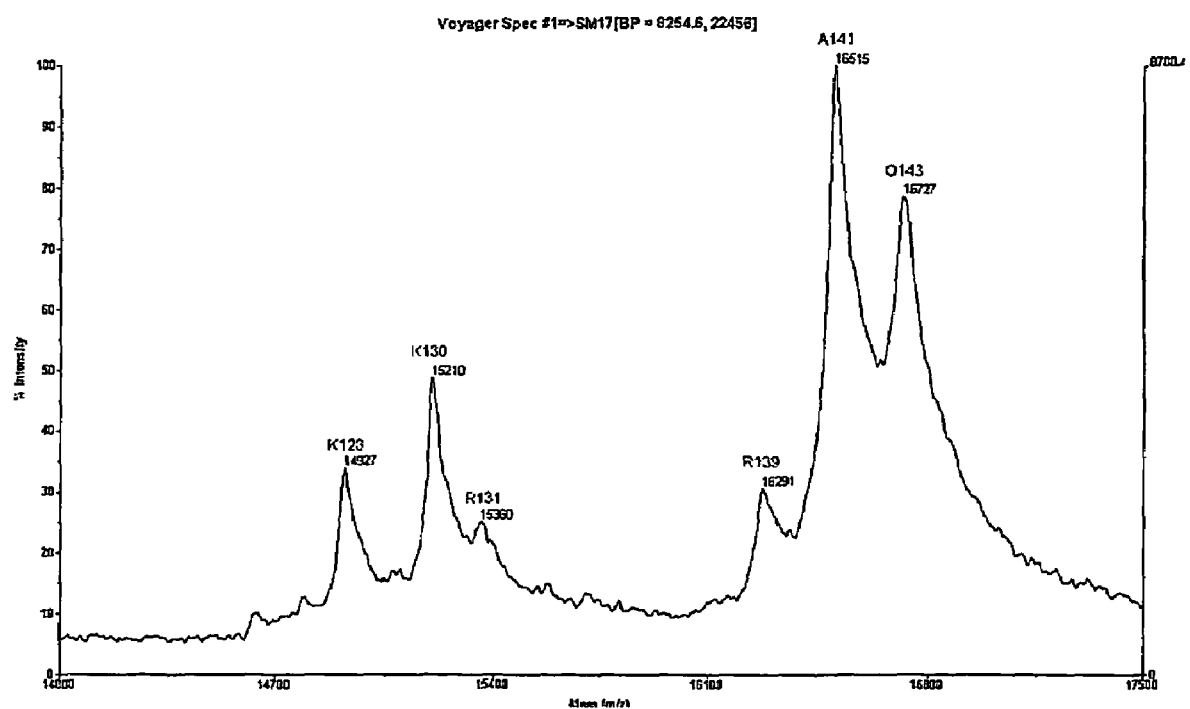
Figure 3:
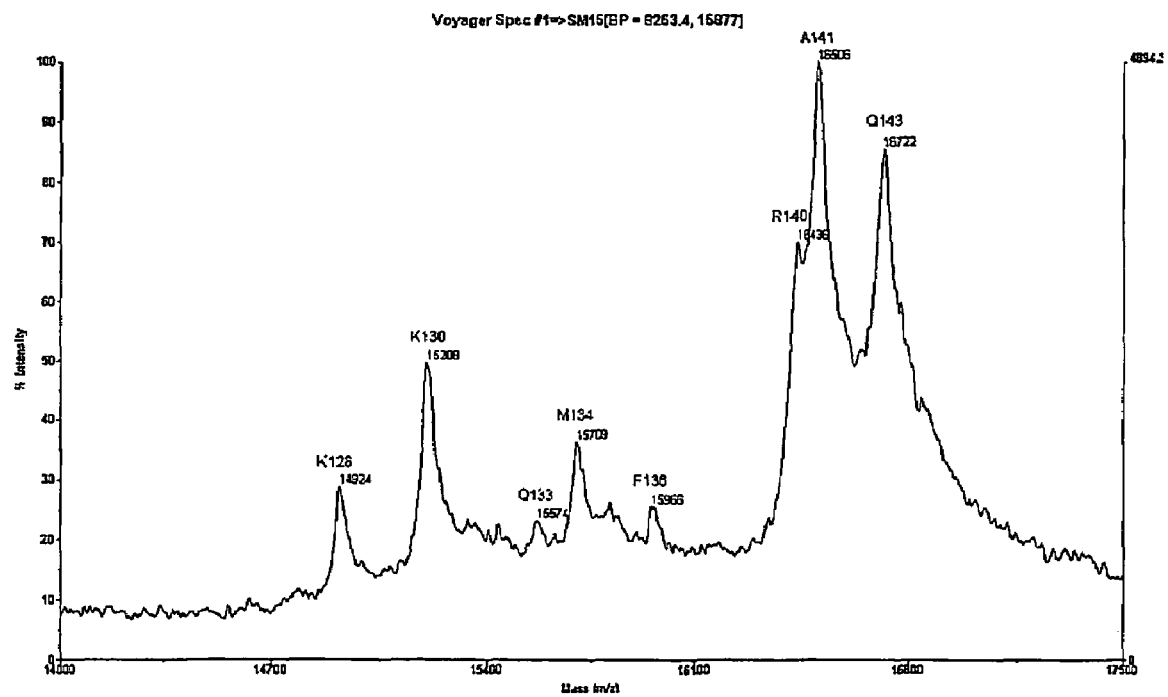
Figure 4:
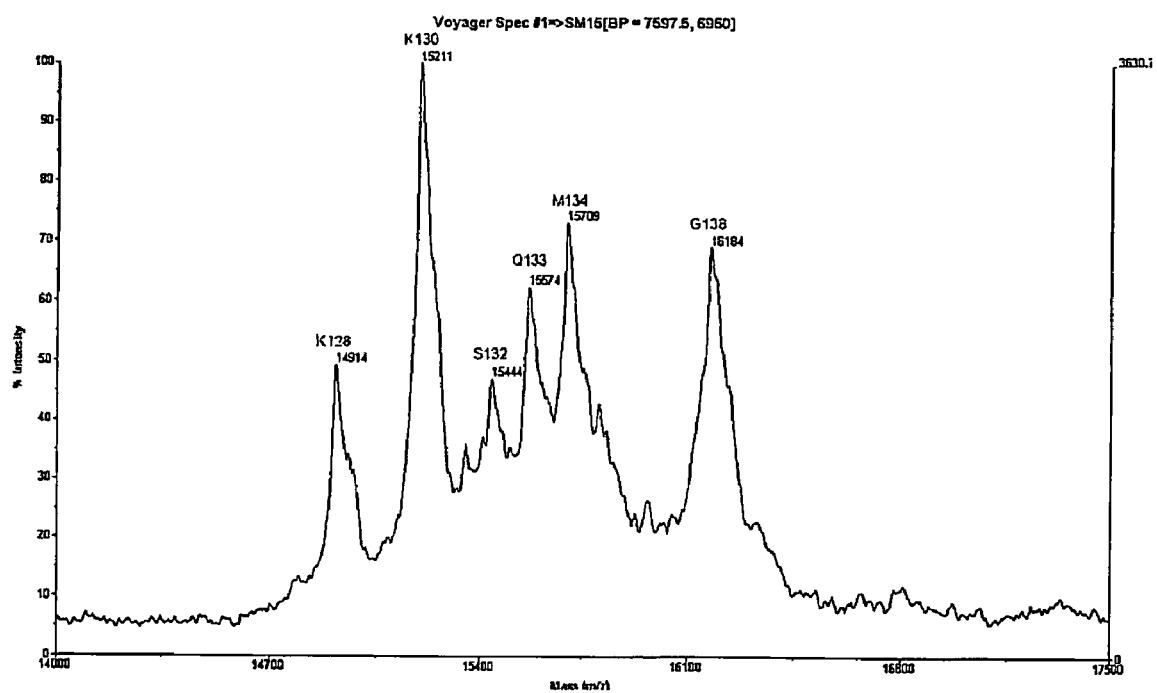
Figure 5:
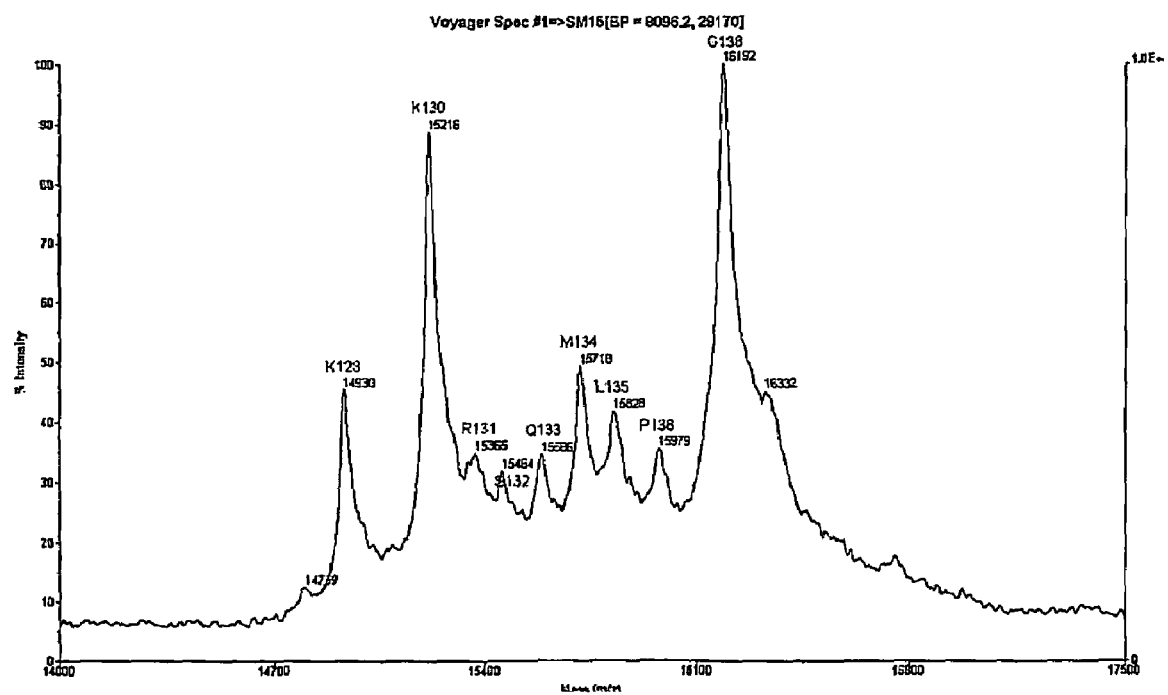
Figure 6:
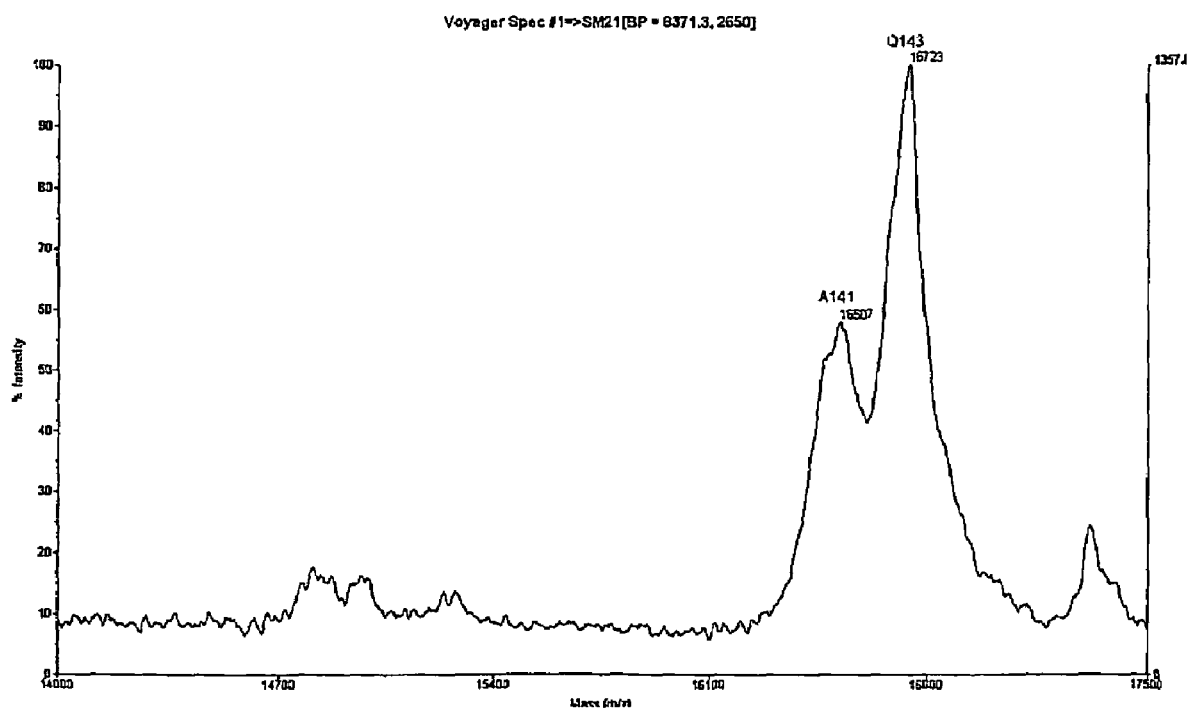
Figure 7:
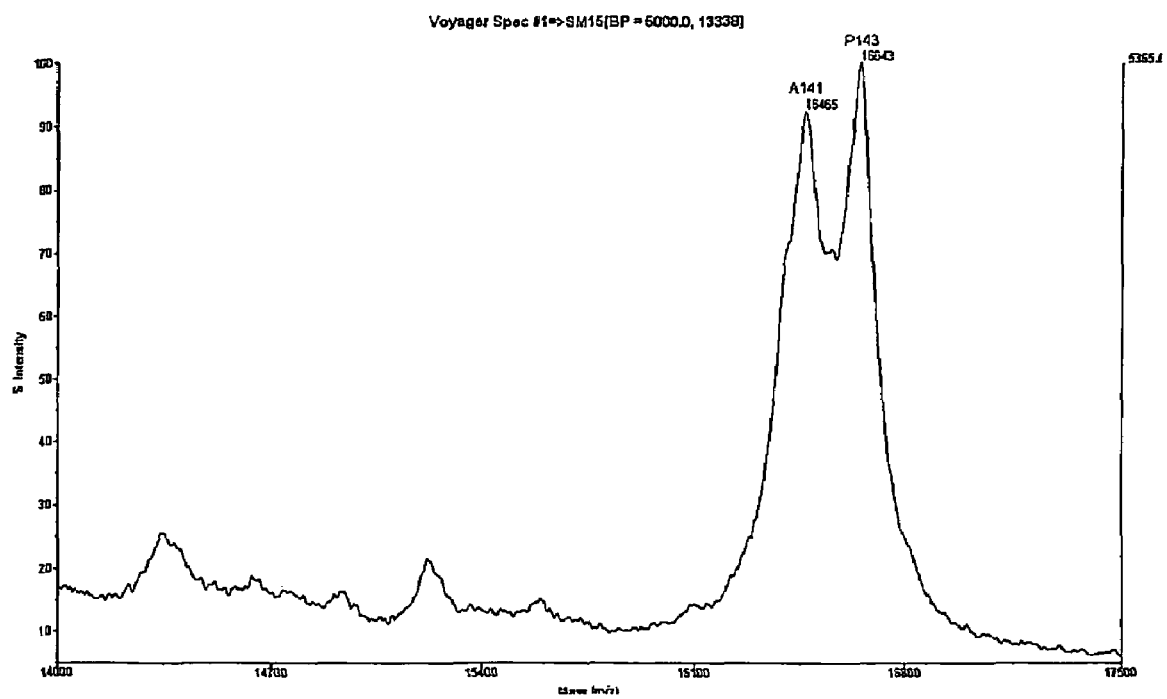
Figure 8:
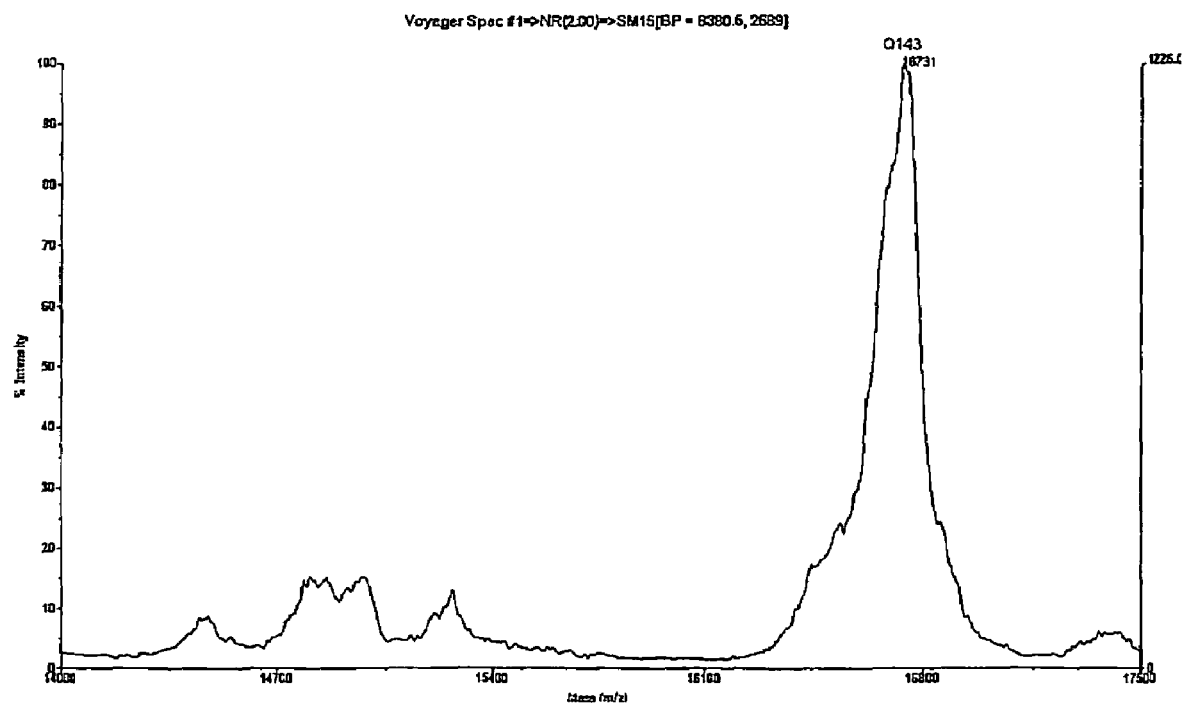
Figure 9:
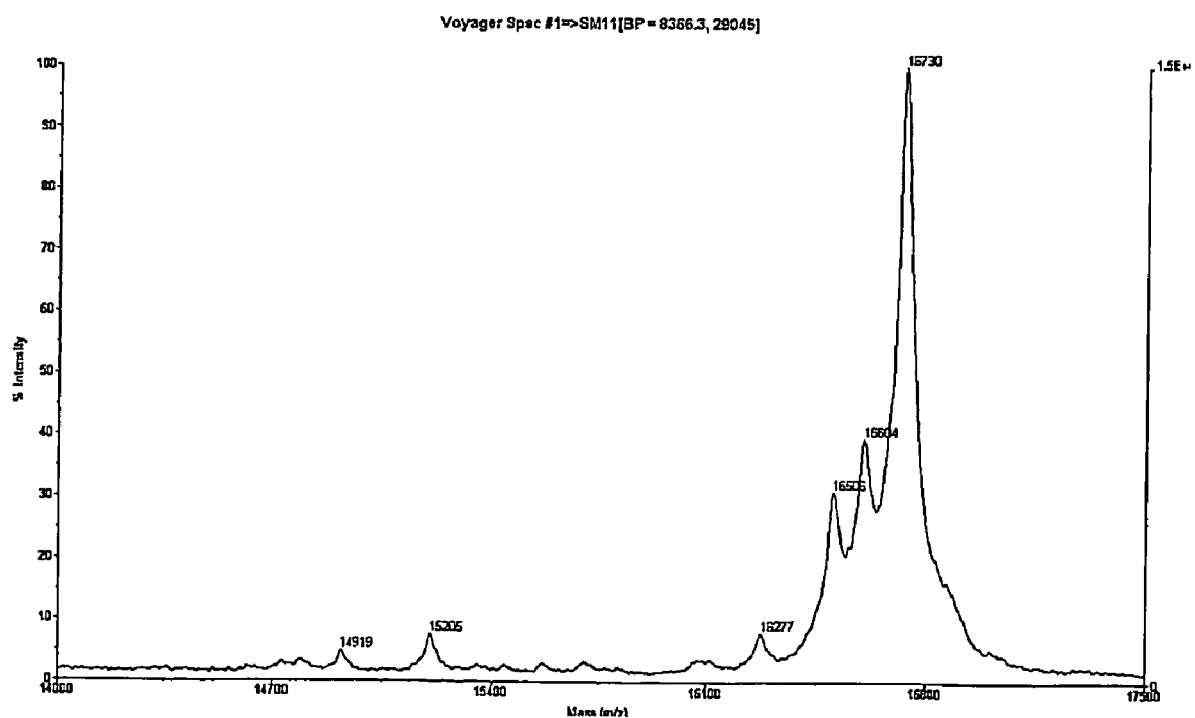
Figure 10:
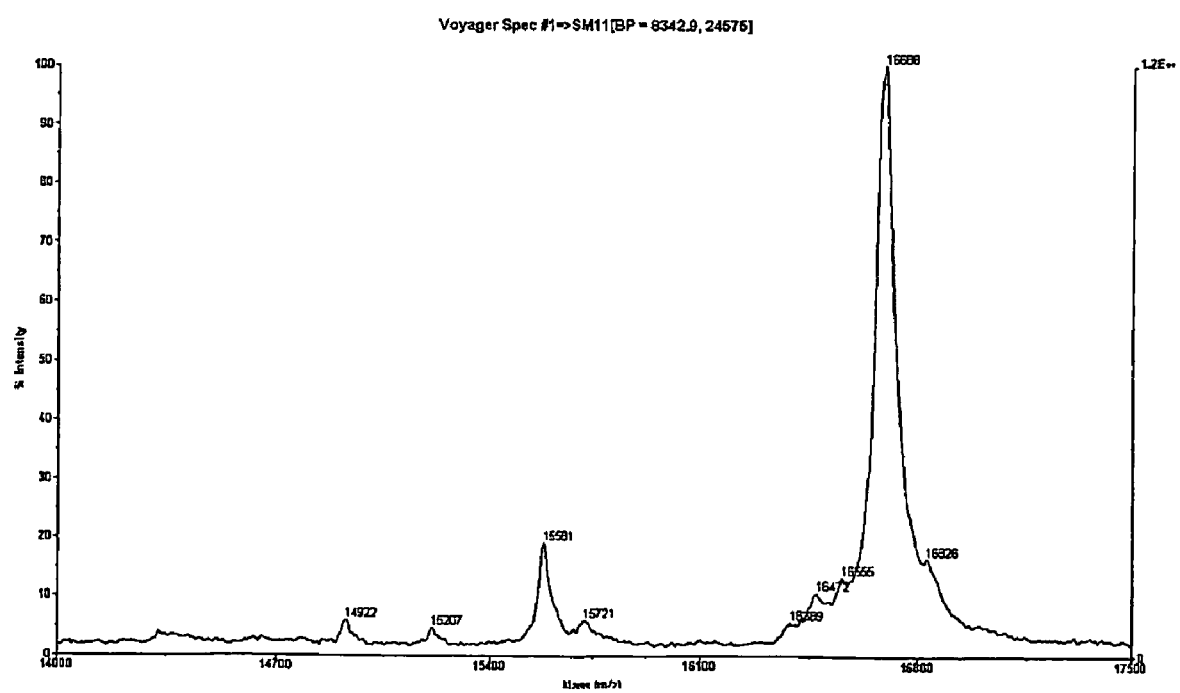
Figure 11:
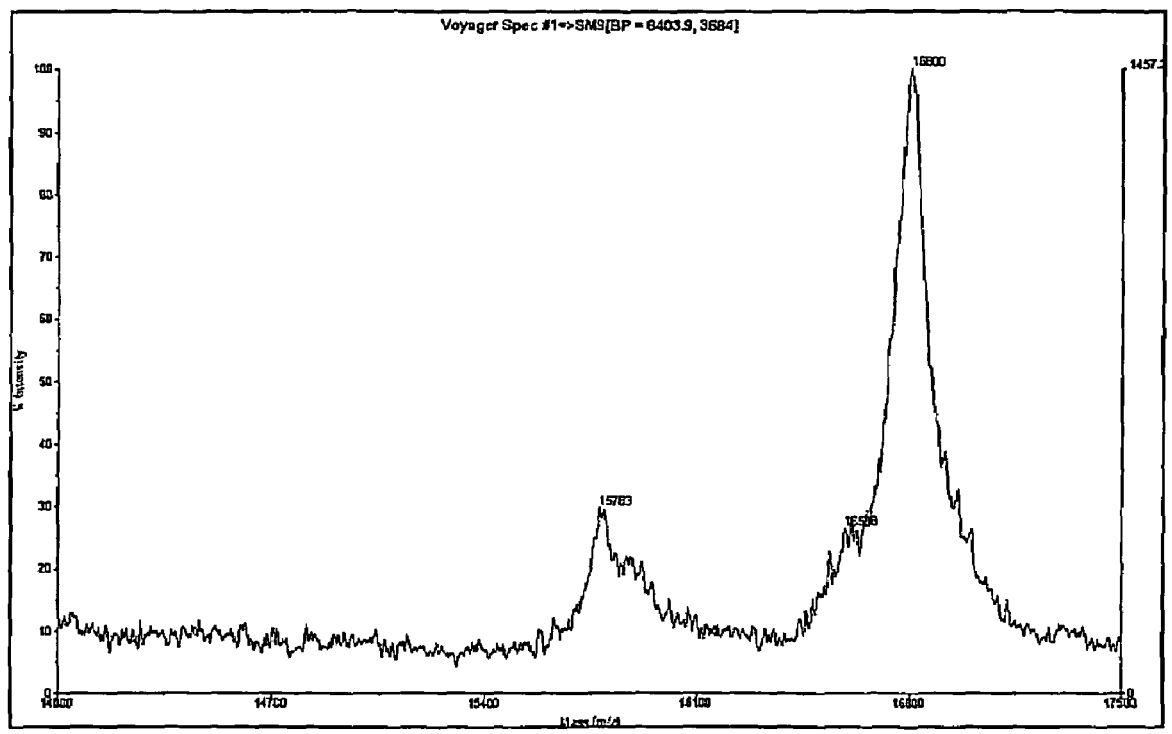
Figure 12:
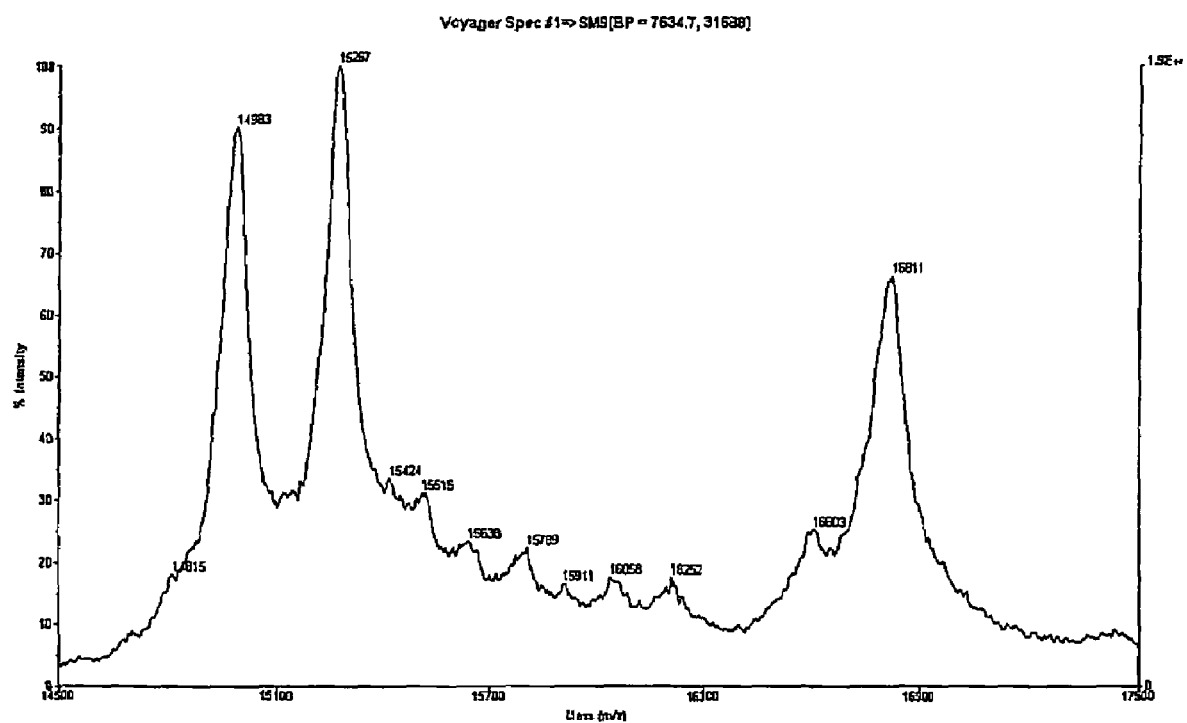
Figure 13:
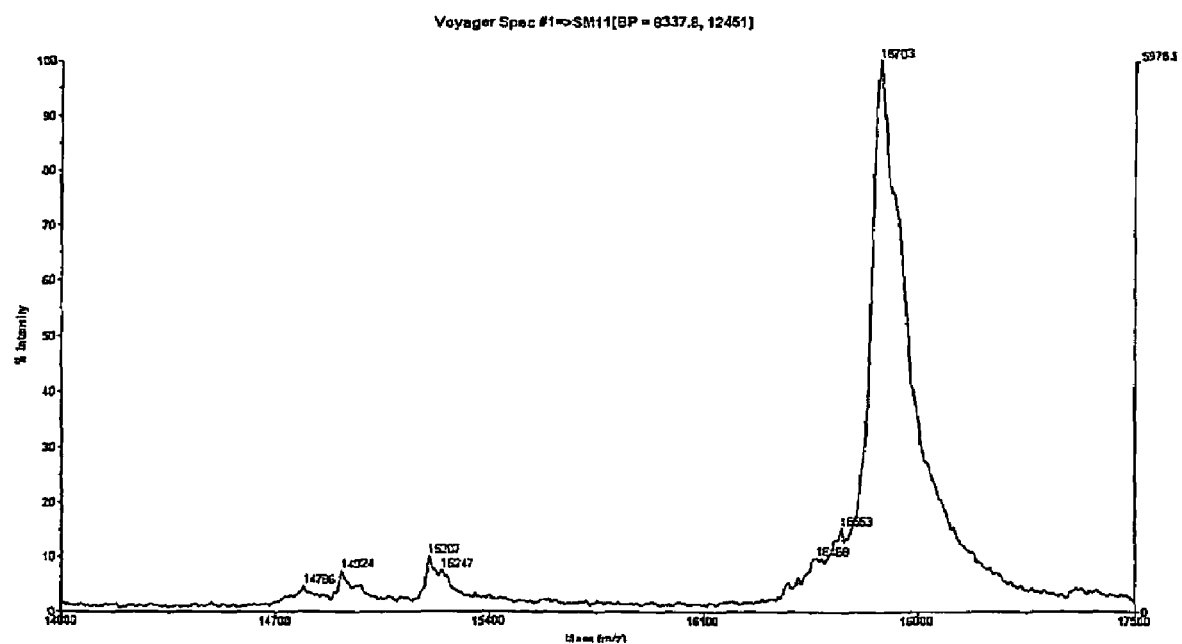

Using the above approach, the following IFNG variants were analysed:

E38N+S40T+S99T (reference)—see FIG. 1
E38N+S40T+S99T+R137P (reference)—see FIG. 2
E38N+S40T+S99T+R139P (reference)—see FIG. 3
E38N+S40T+S99T+S142P (reference)—see FIG. 4
E38N+S40T+S99T+Q143P (reference)—see FIG. 5
E38N+S40T+S99T+R137P+R139P (reference)—see FIG. 6
E38N+S40T+S99T+R137P+R139P+Q143P (reference)—see FIG. 7
E38N+S40T+S99T+R137P+R139P+S142P—see FIG. 8
E38N+S40T+S99T+R137P+S142P—see FIG. 9
E38N+S40T+S99T+S132P+R137P+R140P—see FIG. 10
E38N+S40T+S99T+S132P+R140P—see FIG. 11
E38N+S40T+S99T+R140P (reference)—see FIG. 12
E38N+S40T+S99T+R137P+R140P—see FIG. 13

In FIG. 1 a significant C-terminal processing is clearly seen for the variant [E38N+S40T+S99T]huIFNG.

In FIGS. 2 and 3 it can be seen that the presence of either of the additional substitutions R137P or R139P leads to lesser, but still pronounced, C-terminal processing than seen for [E38N+S40T+S99T]huIFNG.

In FIGS. 4 and 5 it can be seen that the presence of either of the additional substitutions S142P or Q143P leads to unchanged, or even more pronounced, C-terminal processing than seen for [E38N+S40T+S99T]huIFNG.

In FIG. 6 it can be seen that the presence of both of the additional substitutions R137P and R139P leads to lesser and more homogeneous C-terminal processing than seen for [E38N+S40T+S99T]huIFNG and for [E38N+S40T+S99T+R139P]huIFNG. The only C-terminally processed form that can be recognised for [E38N+S40T+S99T+R137P+R139P] huIFNG is the protein having Ala141 as C-terminal amino acid residue.

FIG. 7 shows that further inclusion of the substitution Q143P in [E38N+S40T+S99T+R137P+R139P]huIFNG does not alter the C-terminal processing notably. The only C-terminally processed form that can be recognised for E38N+S40T+S99T+R137P+R139P+Q143P]huIFNG is still the protein having Ala141 as C-terminal amino acid residue.

FIG. 8, however, shows that further inclusion of the substitution S142P in [E38N+S40T+S99T+R137P+R139P] huIFNG alters the C-terminal processing notably as the only protein present in significant amount is the full-length protein having Q143 as the C-terminal amino acid residue.

FIG. 9 clearly shows that inclusion of the substitution S142P in [E38N+S40T+S99T+R137P]huIFNG leads to a significantly smaller degree of C-terminal processing and that the full-length protein having Q143 as the C-terminal amino acid residue is the major species present (compare to FIG. 2).

FIG. 10 evidently shows that the variant [E38N+S40T+S99T+S132P+R137P+R140P] huIFNG is hardly C-terminally processed. Only trace amounts of other species than the full-length protein can be identified.

In a similar way, FIG. 11 shows that the full-length form of the variant [E38N+S40T+S99T+S132P+S140P]huIFNG is the major species.

In FIG. 12 a significant C-terminal processing is clearly seen for the variant [E38N+S40T+S99T+R140P]huIFNG.

FIG. 13, however, shows that further inclusion of the substitution R140P in [E38N+S40T+S99T+R137P]huIFNG alters the C-terminal processing notably as the only protein present in significant amount is the full-length protein having Q143 as the C-terminal amino acid residue.

The invention claimed is:

1. A full-length variant of the interferon gamma (IFNG) polypeptide of SEQ ID NO: 1, said variant exhibiting IFNG receptor binding activity and consisting of up to 10 residue modifications in SEQ ID NO: 1, and wherein up to 10 residue modifications includes:
   (a) at least one amino acid substitution in a position selected from the group consisting of S132 and S142; and
   (b) at least one amino acid substitution in a position selected from the group consisting of R137, R139 and R140.

2. The full-length variant according to claim 1, wherein said amino acid substitution is selected from the group consisting of S132P, S142P and S132P+S142P.

3. The full-length variant according to claim 2, wherein said amino acid substitution is S132P.

4. The full-length variant according to claim 2, wherein said amino acid substitution is S142P.

5. The full-length variant of claim 2, wherein at least one non-positively charged amino acid residue is introduced by substitution in a position selected from the group consisting of R137, R139 and R140.

6. The full-length variant according to claim 5, wherein said non-positively charged amino acid residue is a proline residue.

7. The full-length variant of claim 5, wherein said variant comprises the following substitutions: R137P+R139P+S142P.

8. The full-length variant of claim 5, wherein said variant comprises the following substitutions: R137P+S142P.

9. The full-length variant of claim 5, wherein said variant comprises the following substitutions: S132P+R137P+R140P.

10. The full-length variant of claim 5, wherein said variant comprises the following substitutions: S132P+R140P.

11. A full-length variant of the interferon gamma (IFNG) polypeptide of SEQ ID NO: 1, said variant exhibiting IFNG receptor binding activity and consisting of up to 10 residue modifications in SEQ ID NO: 1, wherein up to 10 residue modifications an amino acid substitution in position R137 and an amino acid substitution in position R140.

12. The full-length variant according to claim 11, wherein said variant comprises the substitutions R137X+R140P, wherein X is any amino acid residue, except arginine and lysine.

13. The full-length variant according to claim 11, wherein said variant comprises the substitutions R137P+R140X, wherein X is any amino acid residue, except arginine.

14. The full-length variant of claim 11, wherein said variant comprises the substitutions R137P+R140P.

15. The full-length variant of claim 11, wherein said variant comprises at least one further modification in the C-terminal part from amino acid residue S132 to amino acid residue Q143.

16. The full-length variant according to claim 15, wherein said further modification comprises introduction of at least one cysteine residue.

17. The full-length variant according to claim 16, wherein said cysteine residue is covalently attached to a polymer molecule.

18. The full-length variant according to claim 17, where said polymer molecule is a linear or branched polyethylene glycol.

19. The full-length variant according to claim 11, wherein said modifications are substitutions.

20. The full-length variant according to claim 19, wherein said variant comprises the substitution S99T.

21. The full-length variant of claim 1, wherein said up to 10 residue modifications comprises at least one introduced and/or at least one removed amino acid residue comprising an attachment group for a non-polypeptide moiety.

22. The full-length variant according to claim 21, wherein said up to 10 residue modifications comprises at least one introduced glycosylation site.

23. The full-length variant according to claim 22, wherein said glycosylation site is an N-glycosylation site.

24. The full-length variant according to claim 23, wherein said N-glycosylation site is introduced in a position comprising an amino acid residue having at least 25% of its side chain exposed to the surface.

25. The full-length variant according to claim 24, wherein said N-glycosylation site is introduced in a position comprising an amino acid residue having at least 50% of its said chain exposed to the surface.

26. The full-length variant of claim 23, wherein said N-glycosylation site is introduced by substitution.

27. The full-length variant according to claim 1, wherein said up to 10 residue modifications is a substitution selected from the group consisting of G18S, G18T, E38N, E38N+S40T, K61S, K61T, S65N+Q67S, S65N+Q67T, N85S, N85T, K94N, Q106S and Q106T.

28. The full-length variant according to claim 27, wherein said substitution is selected from the group consisting of G18T, E38N+S40T, K61T, S65N+Q67T, N85T, K94N and Q106T.

29. The full-length variant according to claim 28, wherein said substitution is selected from the group consisting of G18T, E38N+S40T, K61T, S65N+Q67T and N85T.

30. The full-length variant according to claim 29, wherein said substitution is E38N+S40T.

31. The full-length variant according to claim 21, wherein said up to 10 residue modifications comprises an introduced cysteine residue.

32. The full-length variant according to claim 31, wherein said cysteine residue is introduced in a position comprising an amino acid residue having at least 25% of its side chain exposed to the surface.

33. The full-length variant according to claim 32, wherein said cysteine residue is introduced in a position comprising an amino acid residue having at least 50% of its side chain exposed to the surface.

34. The full-length variant according to claim 31, wherein said cysteine residue is introduced by substitution.

35. The full-length variant according to claim 31, wherein said up to 10 residue modifications is a substitution selected from the group consisting of N10C, N16C, E38C, N59C, N83C, K94C, N104C and A124C.

36. The full-length variant according to claim 35 wherein said substitution is selected from the group consisting of N16C, N59C and N16C+N59C.

37. The full-length variant of claim 31, wherein said cysteine residue is covalently attached to a polymer molecule.

38. The full-length variant according to claim 37, wherein said polymer molecule is a linear or branched polyethylene glycol.

39. The full-length variant according to claim 21, wherein said up to 10 residue modifications comprises at least one introduced N-glycosylation site and at least one introduced cysteine residue.

40. The full-length variant of claim 1, wherein said variant comprises an amino acid sequence, which is identical to the amino acid sequence from residue 1 to residue 131 of huIFNG of SEQ ID NO: 1.

41. The full-length variant according to claim 40, wherein said variant is un-glycosylated.

42. The full-length variant of claim 31, wherein said variant is glycosylated.

43. A nucleotide sequence encoding the full-length variant of claim 1.

44. An expression vector comprising a nucleotide sequence as defined in claim 43.

45. An isolated host cell comprising a nucleotide sequence as defined in claim 43 or an expression vector according to claim 44.

46. A composition comprising a full-length IFNG variant of claim 1 and a carrier.

47. A pharmaceutical composition comprising a full-length variant of claim 1 and a pharmaceutically acceptable diluent, carrier or adjuvant.

48. A method for producing a full-length IFNG polypeptide, said method comprising i) cultivating a host cell as defined in claim 45 under conditions suitable for production of the IFNG polypeptide, and ii) recovering the IFNG polypeptide.

* * * * *

SEQUENCE LISTING

```
<160> NUMBER OF SEQ ID NOS: 13

<210> SEQ ID NO 1
<211> LENGTH: 143
<212> TYPE: PRT
<213> ORGANISM: Homo Sapiens
<220> FEATURE:
<221> NAME/KEY: MISC_FEATURE
<223> OTHER INFORMATION: Wild-type mature human IFN Gamma (without the
      signal peptide)

<400> SEQUENCE: 1

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
```

```
                115                 120                 125
Arg Lys Arg Ser Gln Met Leu Phe Arg Gly Arg Ala Ser Gln
    130                 135                 140

<210> SEQ ID NO 2
<211> LENGTH: 166
<212> TYPE: PRT
<213> ORGANISM: Homo Sapiens
<220> FEATURE:
<221> NAME/KEY: MISC_FEATURE
<223> OTHER INFORMATION: Wild-type human IFN gamma with its 23 residue
      leader sequence

<400> SEQUENCE: 2

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 3
<211> LENGTH: 140
<212> TYPE: PRT
<213> ORGANISM: Artificial Sequence
<220> FEATURE:
<223> OTHER INFORMATION: ACTIMMUNE(r) - a 140 residue form of human IFN
      gamma obtained by fermentation from genetically engineered E. Coli

<400> SEQUENCE: 3

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Lys Arg Asp Asp Phe Glu Lys Leu
                85                  90                  95
```

```
Thr Asn Tyr Ser Val Thr Asp Leu Asn Val Gln Arg Lys Ala Ile His
            100                 105                 110

Glu Leu Ile Gln Val Met Ala Glu Leu Ser Pro Ala Ala Lys Thr Gly
        115                 120                 125

Lys Arg Lys Arg Ser Gln Met Leu Phe Arg Gly Arg
130                 135                 140

<210> SEQ ID NO 4
<211> LENGTH: 498
<212> TYPE: DNA
<213> ORGANISM: Artificial Sequence
<220> FEATURE:
<223> OTHER INFORMATION: Description of Artificial Sequence:  Expression
      cassette optimised for expression of interferon gamma in CHO cells

<400> SEQUENCE: 4
atgaagtaca caagctatat cctggccttt cagctgtgca tcgtgctggg ctccctgggc      60
tgctattgcc aggacccctta cgtgaaggag gccgagaacc tgaagaagta ctttaacgcc     120
ggccacagcg atgtggccga caatggcaca ctgtttctgg catcctgaa gaattggaag      180 gaggagagcg atcggaagat catgcagtcc cagatcgtgt ccttctattt caagctgttt     240
aagaatttca aggacgatca gtccatccag aagtccgtgg agaccatcaa ggaggacatg     300
aacgtgaagt ttttcaatag caataagaag aagagagacg atttcgagaa gctgaccaat     360
tactccgtga cagacctgaa cgtgcagaga aaggccatcc acgagctgat ccaggtgatg     420
gccgagctgt cccccgccgc caagaccggc aagagaaaga aagccagat gctgttcaga      480 ggcagacggg ccagccag                                                   498

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:  Antisense
      downstream vector Primer ADJ 013

<400> SEQUENCE: 5
gatggctggc aactagaag                                                   19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:  sense
      upstream vector Primer ADJ014

<400> SEQUENCE: 6
tgtacggtgg gaggtctat                                                   19

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:  Primer
      ADJ093

<400> SEQUENCE: 7
gttcaggtct gtcacgctgt aattggtcag ctt                                   33

<210> SEQ ID NO 8
```

```
<211> LENGTH: 33
<212> TYPE: DNA
<213> ORGANISM: Artificial Sequence
<220> FEATURE:
<223> OTHER INFORMATION: Description of Artificial Sequence: Primer
      ADJ094

<400> SEQUENCE: 8
aagctgacca attacaccgt gacagacctg aac                                      33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Primer
      ADJ091

<400> SEQUENCE: 9
catgatcttc cgatcggtct cgttcttcca att                                      33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Primer
      ADJ092

<400> SEQUENCE: 10
aattggaaga acgagaccga tcggaagatc atg                                      33

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 11
ccgtcagatc ctaggctagc ttattgcggt agtttatcac                               40

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 12
gagctcggta ccaagctttt aagagctgta at                                       32

<210> SEQ ID NO 13
<211> LENGTH: 9
<212> TYPE: DNA
<213> ORGANISM: Artificial Sequence
<220> FEATURE:
<223> OTHER INFORMATION: Description of Artificial Sequence: upstream
      sequence for optimizing mRNA translation

<400> SEQUENCE: 13 gccgccacc                                                                  9
```